(12) United States Patent
Cheng et al.

(10) Patent No.: US 12,391,660 B2
(45) Date of Patent: Aug. 19, 2025

(54) HETEROAROMATIC ACETAMIDE DERIVATIVE, AND PREPARATION AND USE THEREOF

(71) Applicant: Hangzhou Westan Pharmaceutical Technology Co., Ltd, Zhejiang (CN)

(72) Inventors: Yunfeng Cheng, Zhejiang (CN); Yongzhou Hu, Zhejiang (CN)

(73) Assignee: HANGZHOU WESTAN PHARMACEUTICAL TECHNOLOGY CO., LTD, Zhejiang (CN)

( * ) Notice: Subject to any disclaimer, the term of this patent is extended or adjusted under 35 U.S.C. 154(b) by 869 days.

(21) Appl. No.: 17/615,659

(22) PCT Filed: May 29, 2020

(86) PCT No.: PCT/CN2020/093277
§ 371 (c)(1),
(2) Date: Dec. 1, 2021

(87) PCT Pub. No.: WO2020/244460
PCT Pub. Date: Dec. 10, 2020

(65) Prior Publication Data
US 2022/0315549 A1 Oct. 6, 2022

(30) Foreign Application Priority Data
Jun. 3, 2019 (CN) .......... 201910477117.1

(51) Int. Cl.
| | | |
|---|---|---|
| *C07D 295/185* | (2006.01) | |
| *A61P 11/06* | (2006.01) | |
| *C07D 211/16* | (2006.01) | |
| *C07D 221/20* | (2006.01) | |
| *C07D 401/04* | (2006.01) | |
| *C07D 401/12* | (2006.01) | |
| *C07D 401/14* | (2006.01) | |
| *C07D 403/04* | (2006.01) | |
| *C07D 403/06* | (2006.01) | |
| *C07D 405/06* | (2006.01) | |
| *C07D 405/14* | (2006.01) | |
| *C07D 409/04* | (2006.01) | |
| *C07D 413/12* | (2006.01) | |
| *C07D 413/14* | (2006.01) | |

(Continued)

(52) U.S. Cl.
CPC .......... *C07D 295/185* (2013.01); *A61P 11/06* (2018.01); *C07D 211/16* (2013.01); *C07D 221/20* (2013.01); *C07D 401/04* (2013.01); *C07D 401/12* (2013.01); *C07D 401/14* (2013.01); *C07D 403/04* (2013.01); *C07D 403/06* (2013.01); *C07D 405/06* (2013.01); *C07D 405/14* (2013.01); *C07D 409/04* (2013.01); *C07D 413/12* (2013.01); *C07D 413/14* (2013.01); *C07D 417/04* (2013.01); *C07D 417/12* (2013.01); *C07D 417/14* (2013.01); *C07D 471/08* (2013.01)

(58) Field of Classification Search
CPC .. C07D 221/20; C07D 221/22; C07D 401/12; C07D 401/14; C07D 403/12; C07D 403/14; C07D 405/14; C07D 413/12; C07D 417/12; C07D 471/08
See application file for complete search history.

(56) References Cited

U.S. PATENT DOCUMENTS

2003/0187020 A1 10/2003 Astles et al.

FOREIGN PATENT DOCUMENTS

| CN | 1230431 C | 12/2005 |
|---|---|---|
| CN | 106458861 A | 2/2017 |

(Continued)

OTHER PUBLICATIONS

Price et al., "From Mechanism to Cure: Renewing the Goal to Eliminate the Disease of Pain", 2018, Pain Medicine, 19, pp. 1525-1549 (Year: 2018).*

(Continued)

*Primary Examiner* — Jeffrey H Murray
*Assistant Examiner* — Madeline E Braun
(74) *Attorney, Agent, or Firm* — Scully, Scott, Murphy & Presser, P.C.

(57) ABSTRACT

Provided in the present invention are a heteroaromatic acetamide derivative and the preparation and the use thereof, wherein the heteroaromatic acetamide derivative is a heteroaromatic acetamide compound as shown in general formula (I), or a pharmaceutically acceptable salt and/or solvate thereof. According to the present invention, experiments have confirmed that the heteroaromatic acetamide derivative of the present invention can specifically bind to transient receptor potential ankyrin 1 (TRPA1) and inhibit or reduce the activity thereof, and can be used for treating diseases mediated by TRPA1. The present invention further provides a method for preparing the heteroaromatic acetamide derivative, and a drug and pharmaceutical composition containing the heteroaromatic acetamide derivative.

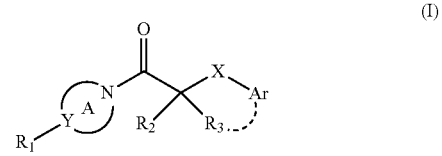

6 Claims, 6 Drawing Sheets

(51) Int. Cl.
    *C07D 417/04*     (2006.01)
    *C07D 417/12*     (2006.01)
    *C07D 417/14*     (2006.01)
    *C07D 471/08*     (2006.01)

(56) References Cited

FOREIGN PATENT DOCUMENTS

| | | | |
|---|---|---|---|
| CN | 110357833 A | 10/2019 | |
| EP | 1736465 A1 | 12/2006 | |
| EP | 2 471 774 B1 | 7/2012 | |
| WO | 2004108671 A1 | 12/2004 | |
| WO | 2006/002350 A1 | 1/2006 | |
| WO | 2006010968 A1 | 2/2006 | |
| WO | 2012020567 A1 | 2/2012 | |
| WO | 2012061926 A1 | 5/2012 | |
| WO | WO-2012173952 A1 * | 12/2012 | ........... A61K 31/496 |

OTHER PUBLICATIONS

Aurora Fine Chemicals, "RN 2310187-42-7", May 17, 2019, Chemcats, 1 page (Year: 2019).*
Aurora Fine Chemicals, "RN 2309729-70-0", May 17, 2019, Chemcats, 1 page (Year: 2019).*
International Preliminary Report on Patentability dated Dec. 16, 2021 received in International Application No. PCT/CN2020/093277, together with an English-language translation.
Supplementary Partial European Search Report & Provisional Opinion dated Jun. 12, 2023 received in European Application No. 20 81 7623.
International Search Report dated Aug. 10, 2020 issued in PCT/CN2020/093277.
Trevisan et al., "Novel Therapeutic Strategy to Prevent Chemotherapy-Induced Persistent Sensory Neuropathy by TRPA1 Blockade", Cancer Res. (May 15, 2013), 73(10), pp. 3120-3131.
Mukhopadhyay et al. "Blocking TRPA1 in Respiratory Disorders: Does It Hold a Promise?", Pharmaceuticals (2016), 9(70), pp. 1-11.
Macpherson et al., "Noxious compounds activate TRPA1 ion channels through covalent modification of cysteines", Nature (Feb. 2007), 445 (7127), pp. 541-545.
Chen et al., "TRPA1 as a drug target-promise and challenges", Naunyn-Schmiedeberg's Arch Pharmacol (2015) 388, pp. 451-463.
Zurborg et al., "Direct activation of the ion channel TRPA1 by Ca2+", Nature Neuroscience (Mar. 2007), vol. 10, No. 3, pp. 277-279.
Bautista et al., "Pungent products from garlic activate the sensory ion channel TRPA1", PNAS (Aug. 23, 2005), 102(34), pp. 12248-12252.
Obata et al., "TRPA1 induced in sensory neurons contributes to cold hyperalgesia after inflammation and nerve Injury", J Clin Invest. (2005), 115(9), pp. 2393-2401.

McNamara et al., "TRPA1 mediates formalin-induced pain", Proc Natl Acad Sci USA (2007), 104 (33), pp. 13525-13530.
Benemei et al., "The TRPA1 channel in migraine mechanism and treatment", British Journal of Pharmacology (2014), 171 (10), pp. 2552-2567.
Yang et al., "Transient Receptor Potential Ankyrin 1 (TRPA1) Channel and Neurogenic Inflammation in Pathogenesis of Asthma", Med Sci Monit (2016), 22, pp. 2917-2923.
Caceres et al., "A sensory neuronal ion channel essential for airway inflammation and hyperreactivity in asthma", Proc Natl Acad Sci USA (2009), 106 (22), pp. 9099-9104.
Andre et al., "Transient receptor potential ankyrin receptor 1 is a novel target for pro-tussive agents", British Journal of Pharmacology (2009), 158, 1621-1628.
Lavinka et al., "Molecular signaling and targets from itch: lessons for cough", Cough (2013), 9:8, pp. 1-13.
Nassini et al., "Transient Receptor Potential Ankyrin 1 Channel Localized to Non-Neuronal Airway Cells Promotes Non-Neurogenic Inflammation", PLoS ONE (Aug. 2012), vol. 7, No. 8, pp. e42454.
Kondo et al., "Role of Transient Receptor Potential A1 in Gastric Nociception", Digestion (Jun. 25, 2010), 82, pp. 150-155.
Cattaruzza et al., "Transient receptor potential ankyrin-1 has a major role in mediating visceral pain in mice", Am J Physiol Gastrointest Liver Physiol (2010), 298, pp. G81-G91.
Wilson et al., "TRPA1 is required for histamine-independent, Mas-related G protein-coupled receptor-mediated itch", Nat Neurosci (2011), 14(5), pp. 595-602.
McGaraughty et al., "TRPA1 modulation of spontaneous and mechanically evoked firing of spinal neurons in uninjured, osteoarthritic, and inflamed rats", Molecular Pain (2010), 6:14, pp. 1-11.
Andersson et al., "The role of the transient receptor potential (TRP) superfamily of cation-selective channels in the management of the overactive bladder", BJU Int. (2010), pp. 1114-1127.
Lee et al. "Thymol and related alkyl phenols activate the hTRPA1 channel", British Journal of Pharmacology (2008) 153, pp. 1739-1749.
Chen et al., "Selective blockade of TRPA1 channel attenuates pathological pain without altering noxious cold sensation or body temperature regulation", Pain 152 (2011), pp. 1165-1172.
Ambrus et al., "Inhibition of TRPC6 by protein kinase C isoforms in cultured human podocytes", J. Cell. Mol. Med. (2015), vol. 19, No. 12, pp. 2771-2779.
Hsieh et al., "H4 receptor antagonism exhibits anti-nociceptive effects in inflammatory and neuropathic pain models in rats", Pharmacology, Biochemistry and Behavior (2010), 95, pp. 41-50.
Liang et al., "Development and Research Progress of Drug Targeting TRPA1 Channel", Progess in Modern Biomedicine (Mar. 2019), vol. 19, No. 5, pp. 996-1000.

* cited by examiner

HETEROAROMATIC ACETAMIDE DERIVATIVE, AND PREPARATION AND USE THEREOF

TECHNICAL FIELD

The present invention belongs to the field of medicine and relates to a heteroaromatic acetamide derivative as a transient receptor potential ankyrin 1 (TRPA1) channel inhibitor, and a method for preparing the same, as well as use thereof in preparation of a medicament for treating diseases mediated by TRPA1.

BACKGROUND OF THE INVENTION

The transient receptor potential ankyrin 1 (TRPA1) channel, initially also known as ANKTM1 or P120, is a non-selective cation channel belonging to the superfamily of transient receptor potential (TRP) channel. TRPA1 is mainly expressed on sensory neurons (C fibers), but it is also expressed on non-neural cells. As an irritant sensor for exogenous stimulants and endogenous proinflammatory mediators, it plays an important role in maintaining the functions including the perception/nociception and inflammatory response of organs and tissues such as the respiratory system, digestive system, and urinary system (Chen and Hackos, Naunyn-Schmiedebergs Arch Pharmacol 2015, 388:451-463). Therefore, blocking the TRPA1 channel may be useful to treat neuropathic pain and inflammatory pain, respiratory diseases such as asthma, allergic chronic cough, chronic obstructive pulmonary disease (COPD) and allergic rhinitis, etc., diseases of digestive tract such as functional gastrointestinal disorders, irritable bowel syndrome, enteritis and pancreatitis, etc., diseases of the urinary and reproductive tract such as cystitis, overactive bladder and dysmenorrhea, etc. In addition, blocking the TRPA1 channel can also treat pruritus and other skin diseases, including allergic dermatitis and burns, as well as osteoarthritis, etc., which are associated with the channel (Mukhopadhyay et al. Pharmaceuticals 2015, 9 (70):1-11).

TRPA1, like the other TRP channel families, comprises a tetramer consisted of 4 subunits, wherein the ion-transferring hole is located in the center of the tetramer. Each subunit contains 6 transmembrane segments (S1-S6) and intracellular N- and C-terminuses. The N-terminal region contains ankyrin repeats unique to TRPA1. TRPA1 is a ligand-dependent ion channel that undergoes structural changes upon binding to a ligand. As a result, the channel is opened, and cations such as calcium ions and sodium ions flow into the cells to regulate the membrane potential of the cells. Irritating natural substances (for example, allyl isothiocyanate (AITC), cinnamaldehyde, etc.), environmental stimulants (for example, formaldehyde, acrolein, etc.), endogenous substances (for example, 4-hydroxynonenal, etc.) and so on are well known as ligands for TRPA1. Many ligands such as AITC and cinnamaldehyde form covalent bonds with the cysteine residues and lysine residues at the N-terminus in the cytoplasm to activate the channel (Macpherson et al. Nature 2007, 445 (7127): 541-5). In addition, TRPA1 can also be activated by cold stimulation and intracellular $Ca^{2+}$ upregulation (Chen and Hackos, Naunyn-Schmiedebergs Arch Pharmacol 2015, 388:451-463). It is known that intracellular $Ca^{2+}$ binds to the N-terminal EF-hand domain to open the channel (Zurborg et al. Nat Neurosci. 2007, 10 (3): 277-9). It has been reported that TRPA1 is highly expressed in sensory nerves such as spinal nerve, vagus nerve, and trigeminal nerve, and it is said that TRPA1 is co-expressed with perception/nociception-related markers such as TRPV1, calcitonin gene-related peptide (CGRP) and substance P (Bautista et al. Proc Natl Acad Sci USA 2005, 102 (34): 12248-52). Therefore, it can be considered that when TRPA1, which exists in the sensory nerves, is activated by various irritants, the channel opens and the cell membrane is depolarized, which causes the nerve endings to release neuropeptides and the like substances (CGRP, substance P), thereby transmitting pain and other sensations. It has been reported that in a pain model, TRPA1 gene knockdown by the gene specific antisense method can improve hyperalgesia induced by inflammation and nerve damage (Obata et al. J Clin Invest. 2005, 115 (9): 2393-401). Also, it has been reported that a pain behavior induced by formalin disappears in TRPA1 gene knockout mouse (McNamara et al. Proc Natl Acad Sci USA 2007, 104 (33): 13525-30). From the above, TRPA1 is considered to play an important role in the nociceptive transmission. There are reports suggesting that TRPA1 is involved in migraine and diabetic neuropathy (Benemei et al. Br J Pharmacol 2014, 171 (10): 2552-67). Thus, TRPA1 is expected as a treatment target in pain-associated diseases such as nociceptive pain, neuropathic pain and the like.

TRPA1, as a sensor for endogenous and exogenous chemical stimulants, is expressed in the primary sensory neurons of the respiratory system. Various stimulants induce neuropathic inflammation of the respiratory tract to release neuropeptides, pro-inflammatory factors and chemokines via the sensor effect of TRPA1. These substances further mediate inflammatory responses including hemangiectasis, white blood cell extravasation, high mucus secretion, and respiratory tract constriction, etc., which cause asthma, chronic obstructive pulmonary disease (COPD), allergic chronic cough, allergic rhinitis and other respiratory diseases (Yang and Li, Med Sci Monit 2016, 22: 2917-2923). On the other hand, these respiratory diseases can persistently activate TRPA1 via various stimulants released thereby, further aggravating the disease (Chen and Hackos, Naunyn-Schmiedebergs Arch Pharmacol 2015, 388:451-463).

It is also reported that, TRPA1 gene knockout can inhibit airway inflammation in an ovalbumine-induced mouse asthma model (Caceres et al. Proc Natl Acad Sci USA. 2009, 106 (22): 9099-104). Also in this model, a TRPA1 antagonist, HC-030031, can reduce the release of pro-inflammatory factors and neuropeptides. Another TRPA1 antagonist, GRC17536, can reduce acidophilic leukocytes and inhibit mucus secretion and airway hyperreactivity in a mouse asthma model. Likewise, the TRPA1 antagonist CB-625 can effectively reduce the late-stage asthma response and antigen-induced airway response (Mukhopadhyay et al. Pharmaceuticals 2015, 9 (70): 1-11). Therefore, blocking TRPA1 is an effective means to treat asthma.

Many studies have also shown that TRPA1 activation plays an important role in driving the cough reflex. For example, acrolein in cigarette smoke and crotonaldehyde and cinnamaldehyde contained in polluted air are all TRPA1 activators and are now recognized as cough inducing substances. These substances can induce a strong and long-lasting cough response in guinea pigs, and taking the TRPA1 antagonist HC-030031 can significantly attenuate this response (Andre et al. Br J Pharmacol 2009, 158: 1621-1628).

The cough response mediated by TRPA1 is also related to endogenous biochemical substances. Many cough-related diseases generate these substances, such as prostaglandin E2 (PGE2) and bradykinin. Therefore, TRPA1 may play a central driving role in chronic cough, a common symptom produced under a variety of pathological conditions (Lavinka et al. Cough 2013, 9 (1):8).

In addition, there are sufficient evidences suggesting that TRPA1, as a sensor of various pollutants, oxides, and cigarette smoke components (CS), is also involved in the pathological mechanism of chronic obstructive pulmonary disease (COPD). For example, in a mouse model of COPD, CS and acrolein can induce keratinocytes to release chemokines (humanized mouse IL-8), and TRPA1 gene knockout significantly decreases the release of chemokines. Pretreatment of mice with HC-030031 shows that it has a protective effect on the plasma protein extravasation induced by CS (Nassini et al. PLoS ONE 2012, 7: e42454).

Also, TRPA1 is known to show high expression in the afferent sensory nerve projected on the gastrointestinal tract such as esophagus, stomach, large intestine and the like. It has been reported that TRPA1 knockdown decreases nociceptive reaction due to extension of stomach (Kondo et al. Digestion 2010, 82 (3): 150-5), and large intestine hyperalgesia induced by AITC and 2,4,6-trinitrobenzenesulfonic acid (TNBS) is normalized in TRPA1 gene knockout mouse (Cattaruzza et al. Am J Physiol Gastrointest Liver Physiol 2010, 298 (1): G81-91). From the above, TRPA1 is suggested to play an important role in the perception/nociception transmission in the gastrointestinal tract, and is expected to be effective for the treatment of disease of digestive system such as functional gastrointestinal disorder, irritable bowel syndrome, reflux esophagitis, inflammatory bowel disease (Crohn's disease, ulcerative colitis), pancreatitis and the like. As other diseases involving TRPA1, dermatic diseases such as pruritus, allergic dermatitis including atopic dermatitis, burn and the like (Wilson et al. Nat Neurosci 2011, 14 (5): 595-602), inflammatory diseases such as burn, osteoarthritis and the like (McGaraughty et al. Mol Pain 2010, 6:14), bladder diseases such as overactive bladder, abnormal urination, cystitis and the like (Andersson et al. BJU Int. 2010,106 (8):1114-27), neurological diseases such as anticancer agent-induced neuropathy and the like (Trevisan et al. Cancer Res. 2013, 73 (10): 3120-31) and the like are known. Thus, TRPA1 antagonists have attracted much attention and expectations as a new therapeutic drug for pain diseases, digestive system diseases, lung diseases, dermatic diseases, inflammatory diseases, bladder diseases and neurological diseases in human.

SUMMARY OF THE INVENTION

An object of the present invention is to provide a heteroaromatic acetamide derivative, which is an aromatic heteroacetamide compound represented by formula (I) or a pharmaceutically acceptable salt or solvate thereof,

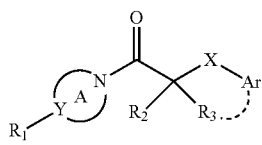

(I)

wherein:
ring A is selected from 6-membered aliphatic heterocyclic group or aliphatic bridged cyclic group containing 1-2 nitrogen atoms, preferably the following nitrogen-containing 6-membered aliphatic heterocyclic group or nitrogen-containing bridged cyclic group:

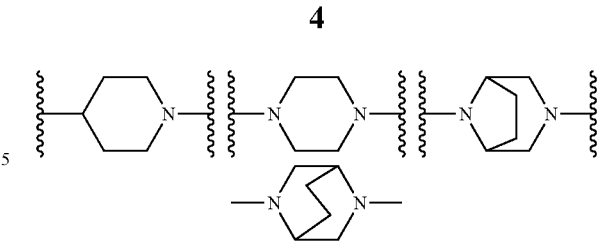

Ar is selected from substituted or unsubstituted phenyl, and substituted or unsubstituted 5- or 6-membered heteroaromatic cyclic group containing 1-2 atoms selected from O, N and S, wherein Ar is preferably selected from substituted phenyl, 5-membered or 6-membered heteroaromatic cyclic group as follows:

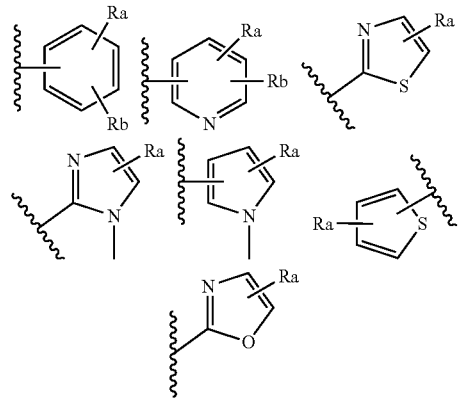

Ra and Rb are the same or different or absent, each of which is independently selected from H, halo, nitro, cyano, methyl, trifluoromethyl, trifluoromethoxy, methoxy, C1-3 alkoxy;

$R_1$ is selected from substituted or unsubstituted phenyl, substituted or unsubstituted 5- or 6-membered heteroaromatic cyclic group containing 1-2 atoms selected from O, N and S, 5- or 6-membered aliphatic cyclic group, C1-5 straight or branched alkyl;

$R_2$ and $R_3$ are the same or different, which are respectively independently selected from H, C1-5 straight or branched alkyl, phenyl; or $R_2$ and $R_3$ form a 3-membered to 6-membered aliphatic cyclic group or aliphatic heterocyclic group; or $R_2$ is H, $R_3$ and Ar are connected to form indolyl, indolinyl, benzofuranyl, 2,3-dihydrobenzofuranyl;

X is selected from NH, O, S;

Y is selected from N or —CH—;

Unless otherwise stated, the optionally substituted elements as described herein can be substituted at any chemically possible position.

More specifically, in the structure of the formula (I) compound of the present invention, when ring A is substituted piperidinyl or piperazinyl, and Ar is substituted phenyl, 5- or 6-membered heteroaromatic cyclic group, preferred compounds therein may be selected from:

4-((1-(4-(4-(trifluoromethyl)phenyl)piperazine-1-carbonyl)cyclopentyl)amino)benzo nitrile;
4-((1-(4-(3-(trifluoromethyl)phenyl)piperazine-1-carbonyl)cyclopentyl)amino)benzo nitrile;
4-((1-(4-(2-(trifluoromethyl)phenyl)piperazine-1-carbonyl)cyclopentyl)amino)benzo nitrile;
4-((1-(4-(2-(trifluoromethoxy)phenyl)piperazine-1-carbonyl)cyclopentyl)amino)benzonitrile;

4-((1-(4-(4-(trifluoromethoxy)phenyl)piperazine-1-carbonyl)cyclopentyl)amino)benzonitrile;
4-((1-(4-(4-chloro-2-methoxyphenyl)piperazine-1-carbonyl)cyclopentyl)amino)benzonitrile;
4-((1-(4-(3-methyl)phenyl)piperazine-1-carbonyl)cyclopentyl)amino)benzonitrile;
4-((3-(4-(3-trifluoromethyl)phenyl)piperazine-1-carbonyl)pentan-3-yl)amino)benzonitrile;
4-((3-(4-(3-trifluoromethyl)phenyl)piperazine-1-carbonyl)propan-2-yl)amino)benzonitrile;
4-((1-(4-(5-(trifluoromethyl)pyridin-2-yl)piperazine-1-carbonyl)cyclopentyl)amino)benzonitrile;
4-((1-(4-(6-(trifluoromethyl)pyridin-2-yl)piperazine-1-carbonyl)cyclopentyl)amino)benzonitrile;
4-((1-(4-(6-(trifluoromethyl)pyridin-2-yl)piperazine-1-carbonyl)cyclopropyl)amino)benzonitrile;
4-((1-(4-(6-(trifluoromethyl)pyridin-2-yl)piperazine-1-carbonyl)cyclobutyl)amino)benzonitrile;
4-((3,3-dimethyl-1-oxo-1-(4-(6-trifluoromethyl)pyridin-2-yl)piperazine-1-yl)butan-2-yl)amino)benzonitrile;
4-((1-(4-(6-methylpyridin-2-yl)piperazine-1-carbonyl)cyclopentyl)amino)benzonitrile  6-(4-(1((4-cyanophenyl)amino)cyclopentane-1-carbonyl)piperazine-1-yl)N, N-dimethylnicotinamide;
4-((1-(4-(5-(trifluoromethyl)pyrimidin-2-yl)piperazine-1-carbonyl)cyclopentyl)amino)benzonitrile;
4-((1-(4-(4-(trifluoromethyl)pyrimidin-2-yl)piperazine-1-carbonyl)cyclopentyl)amino)benzonitrile;
4-((1-(4-(6-(trifluoromethyl)pyridazin-3-yl)piperazine-1-carbonyl)cyclopentyl)amino)benzonitrile;
4-((1-(4-(6-(trifluoromethyl)pyridazin-3-yl)piperazine-1-carbonyl)cyclopentyl)amino) chlorobenzene;
4-((1-(4-(6-(trifluoromethyl)pyridazin-3-yl)piperazine-1-carbonyl)cyclopentyl)amino) nitrobenzene;
2-chloro-4-((1-(4-(6-(trifluoromethyl)pyridazin-3-yl)piperazine-1-carbonyl)cyclopentyl)amino)benzonitrile;
2-chloro-4-((1-(4-(6-(trifluoromethyl)pyridazin-3-yl)piperazine-1-carbonyl)phenyl)amino)benzonitrile;
4-((1-(4-(5-(trifluoromethyl)thien-2-yl)piperazine-1-carbonyl)cyclopentyl)amino)benzonitrile;
4-((1-(4-(5-(trifluoromethyl)thiazol-2-yl)piperazine-1-carbonyl)cyclopentyl)amino)benzonitrile;
4-((1-(4-(1-methyl-1H-pyrazol-3-yl)piperazine-1-carbonyl)cyclopentyl)amino)benzo nitrile;
4-((1-(4-(6-(trifluoromethyl)pyridin-2-yl)piperazine-1-carbonyl)cyclopentyl)amino)phenylacetylene;
4-((1-(4-(cyclopentanemethyl)piperazine-1-carbonyl)cyclopentyl)amino)benzonitrile
4-((1-(4-(tert-butyl)piperidine-1-carbonyl)cyclopentyl)amino)benzonitrile;
4-((1-(4-(isobutyl)piperidine-1-carbonyl)cyclopentyl)amino)benzonitrile;
4-((1-(4-(cyclopentyl)piperidine-1-carbonyl)cyclopentyl)amino)benzonitrile;
4-((1-(8-aza-spiro[4.5]decane-8-carbonyl)cyclopentyl)amino)benzonitrile;
4-((1-(4-(cyclohexyl)piperidine-1-carbonyl)cyclopentyl)amino)benzonitrile;
4-((1-(4-(tert-butyl)piperidine-1-carbonyl)cyclopentyl)amino)phenylacetylene;
4-((1-(4-(tert-butyl)piperidine-1-carbonyl)cyclobutyl)amino)benzonitrile;
4-((1-(4-(tert-butyl)piperidine-1-carbonyl)cyclopropyl)amino)benzonitrile;
2-((1-(4-(tert-butyl)piperidine-1-carbonyl)cyclopentyl)amino)thiazole-4-carbonitrile;
2-((1-(4-(tert-butyl)piperidine-1-carbonyl)cyclopentyl)amino)thiazole-5-carbonitrile;
2-((1-(4-(tert-butyl)piperidine-1-carbonyl)cyclopentyl)amino)oxazole-4-carbonitrile; 4-((1-(4-(tert-butyl)piperidine-1-carbonyl)cyclopentyl)amino)-1-methyl-1H-imidazole-2-carbonitrile;
4-((1-(4-(tert-butyl)piperidine-1-carbonyl)tert-butyl)amino)benzonitrile;
4-((1-(4-(tert-butyl)piperidine-1-carbonyl)cyclopentyl)methylamino)benzonitrile;
4-((1-(4-(tert-butyl)piperidine-1-carbonyl)cyclopentyl)methylamino)trifluoromethylbenzene;
4-((1-(4-(tert-butyl)piperidine-1-carbonyl)cyclopentyl)amino)chlorobenzene;
4-((1-(4-(6-(trifluoromethyl)pyridin-2-yl)piperazine-1-carbonyl)cyclopentyl)oxy)benzonitrile;
4-((1-(4-(m-methylphenyl)piperazine-1-carbonyl)cyclopentyl)oxy)benzonitrile;
4-((1-(4-(trifluoromethyl)phenyl)piperazine-1-carbonyl)cyclopentyl)oxy)benzonitrile;
4-((1-(4-(4-(trifluoromethyl)pyrimidin-2-yl)piperazine-1-carbonyl)cyclopentyl)oxy)benzonitrile;
4-((1-(4-(4-(trifluoromethyl)pyrimidin-2-yl)piperazine-1-carbonyl)tert-butyl)oxy)benzonitrile;
4-((1-(4-(6-(trifluoromethyl)pyridazin-3-yl)piperazine-1-carbonyl)cyclopentyl)oxy)benzonitrile;
4-((1-(4-(6-(trifluoromethyl)pyridazin-3-yl)piperazine-1-carbonyl)cyclopentyl)oxy)nitrobenzene;
4-((1-(4-(tert-butyl)piperidine-1-carbonyl)cyclopentyl)oxy)benzonitrile;
4-((1-(4-(tert-butyl)piperazine-1-carbonyl)cyclopentyl)oxy)benzonitrile;
4-((1-(4-(6-(trifluoromethyl)pyridin-2-yl)piperazine-1-carbonyl)cyclobutyl)oxy)benzo nitrile;
4-((1-(4-(4-(trifluoromethyl)pyrimidin-2-yl)piperazine-1-carbonyl)cyclopentyl)oxy)oxazole-4-carbonitrile;
2-chloro-4-((1-(4-(6-(trifluoromethyl)pyridazin-3-yl)piperazine-1-carbonyl)cyclopentyl)oxy)benzonitrile;
1-methyl-4-((1-(4-(5-(trifluoromethyl)pyridin-2-yl)piperazine-1-carbonyl)cyclopentyl)oxy)-1H-imidazole-2-carbonitrile;
2-((1-(4-(5-(trifluoromethyl)pyridin-2-yl)piperazine-1-carbonyl)cyclopentyl)oxy)thiazole-5-carbonitrile;
4-(1-phenyl-2-(4-6-(trifluoromethyl)pyridazin-3-yl)piperazine-1-yl)ethoxy)benzonitrile;
4-((1-(4-(tert-butyl)piperazine-1-carbonyl)cyclopentyl)oxy)trifluoromethylbenzene;
5-((1-(4-(tert-butyl)piperidine-1-carbonyl)cyclopentyl)oxy)-1-methyl-1H-pyrrole-3-carbonitrile;
4-((1-(4-(tert-butyl)piperazine-1-carbonyl)cyclopentyl)sulfanyl)benzonitrile;
5-((1-(4-(tert-butyl)piperidine-1-carbonyl)cyclopentyl)sulfanyl)-1-methyl-1H-indole.

Further, in the structure of the formula (I) compound of the present invention, when ring A is substituted nitrogen-containing bridged cyclic group, and Ar is substituted phenyl, 5- or 6-membered heteroaromatic cyclic group, preferred compounds thereof are selected from:
4-((1-(8-(6-(trifluoromethyl)pyridin-2-yl)-3,8-diazabicyclo[3.2.1]octane-3-carbonyl)cyclopentyl)amino)benzonitrile;
4-((1-(5-(6-(trifluoromethyl)pyridin-2-yl)-2,5-diazabicyclo[2.2.2]octane-2-carbonyl)cyclopentyl)amino)benzonitrile;
4-((1-(8-(6-(trifluoromethyl)pyridin-2-yl)-3,8-diazabicyclo[3.2.1]octane-3-carbonyl)cyclopentyl)amino)benzonitrile;

4-((1-(5-(6-(trifluoromethyl)pyridin-2-yl)-2,5-diazabicyclo [2.2.2]octane-2-carbonyl)cyclopentyl)oxy)benzonitrile.

Still further, in the structure of the formula (I) compound of the present invention, when ring A is substituted piperidyl or piperazinyl, $R_2$ is H or absent, and $R_3$ and Ar are connected to form indolyl, indolinyl, benzofuranyl, 2,3-dihydrobenzofuranyl, preferred compounds thereof are selected from:
2-(4-(6-(trifluoromethyl)pyridin-2-yl)piperazine-1-carbonyl)-5-cyanoindoline;
2-(4-(4-(trifluoromethyl)pyrimidin-2-yl)piperazine-1-carbonyl)-5-cyanoindoline;
2-(4-(3-(trifluoromethyl)phenyl)piperazine-1-carbonyl)-5-cyanoindoline;
2-(4-(6-(trifluoromethyl)pyridin-2-yl)piperazine-1-carbonyl)-1H-5-cyanoindole;
2-(4-(5-(trifluoromethyl)pyridin-2-yl)piperazine-1-carbonyl)-1H-5-cyanoindole;
2-(4-(6-(trifluoromethyl)pyridin-2-yl)piperazine-1-carbonyl)-2,3-2H-5-cyanobenzofuran;
2-(4-(6-(trifluoromethyl)pyridin-2-yl)piperazine-1-carbonyl)-2,3-2H-5-chlorobenzofuran;
2-(4-(6-methyl)pyridin-2-yl)piperazine-1-carbonyl)-2,3-2H-5-cyanobenzofuran;
2-(4-(5-(trifluoromethyl)pyridin-2-yl)piperazine-1-carbonyl)-5-cyanobenzofuran;
2-(4-(tert-butyl)piperazine-1-carbonyl)-5-cyanoindoline;
2-(4-(tert-butyl)piperidine-1-carbonyl)-5-cyanoindoline;
2-(4-(tert-butyl)piperidine-1-carbonyl)-2,3-2H-5-cyanobenzofuran;
2-(4-(tert-butyl)piperazine-1-carbonyl)-2,3-2H-5-cyanobenzofuran;
2-(4-(6-(trifluoromethyl)pyridin-2-yl)piperazine-1-carbonyl)-5-cyanoindoline;
2-(4-(4-(trifluoromethyl)pyrimidin-2-yl)piperazine-1-carbonyl)-5-cyanoindoline;
2-(4-(3-(trifluoromethyl)phenyl)piperazine-1-carbonyl)-5-cyanoindoline;
2-(4-(6-(trifluoromethyl)pyridin-2-yl)piperazine-1-carbonyl)-1H-5-cyanoindole;
2-(4-(5-(trifluoromethyl)pyridin-2-yl)piperazine-1-carbonyl)-1H-5-cyanoindole;
2-(4-(6-(trifluoromethyl)pyridin-2-yl)piperazine-1-carbonyl)-2,3-2H-5-cyanobenzofuran;
2-(4-(6-(trifluoromethyl)pyridin-2-yl)piperazine-1-carbonyl)-2,3-2H-5-chlorobenzofuran;
2-(4-(6-methyl)pyridin-2-yl)piperazine-1-carbonyl)-2,3-2H-5-cyanobenzofuran;
2-(4-(5-(trifluoromethyl)pyridin-2-yl)piperazine-1-carbonyl)-5-cyanobenzofuran;
2-(4-(tert-butyl)piperazine-1-carbonyl)-5-cyanoindoline;
2-(4-(tert-butyl)piperidine-1-carbonyl)-5-cyanoindoline;
2-(4-(tert-butyl)piperidine-1-carbonyl)-2,3-2H-5-cyanobenzofuran;
2-(4-(tert-butyl)piperazine-1-carbonyl)-2,3-2H-5-cyanobenzofuran.

Methods well known to those skilled in the art may be adopted in the present invention to prepare salts of compounds having basic groups in the heteroaromatic acetamide derivatives as described in the present invention. The salts may be salts of inorganic acids, organic acids, etc. The salts of inorganic acids include, but are not limited to, the corresponding salts formed with hydrohalic acid (such as hydrofluoric acid, hydrobromic acid, hydroiodic acid, hydrochloric acid), nitric acid, sulfuric acid, phosphoric acid, etc.; the salts of organic acids include, but are not limited to, the corresponding salts formed with a malic acid, L-malic acid, D-malic acid, citric acid, fumaric acid, oxalic acid, lactic acid, camphorsulfonic acid, L-camphorsulfonic acid, D-camphorsulfonic acid, p-toluenesulfonic acid, methanesulfonic acid, benzoic acid, etc.

Another object of the present invention is to provide use of the heteroaromatic acetamide derivatives in preparation of transient receptor potential ankyrin 1 (TRPA1) channel inhibitors.

The inhibitor comprises at least one active component and one or more pharmaceutically acceptable carriers or excipients, wherein the active component may be any one or more of the heteroaromatic acetamide compounds of the present invention, the pharmaceutically acceptable salts thereof, and the solvates of the compounds.

The carriers or excipients comprise conventional fillers, diluents, wetting agents, lubricants, binders, disintegrating agents, absorption promoters, surfactants, adsorption carriers and the like in the pharmaceutical field, and flavoring agents, sweeteners and the like can also be added if necessary. The medicaments of the present invention may be prepared into various forms such as tablets, capsules, inhalants, patches, emulsions, suspensions, gels, powders, granules, oral liquids and injections, and medicaments in the above dosage forms may be prepared in accordance with conventional methods in the pharmaceutical field.

The present invention also provides the use of the compounds of formula (I), pharmaceutically acceptable salts thereof or solvates thereof, alone and/or in combination with other drugs, in preparation of TRPA1 inhibitors, especially in preparation of medicaments for treating diseases mediated by TRPA1. The diseases mediated by TRPA1 comprise neuropathic pain and inflammatory pain, respiratory diseases such as asthma, allergic chronic cough, chronic obstructive pulmonary disease (COPD) and allergic rhinitis, etc., diseases of digestive tract such as functional gastrointestinal disorders, irritable bowel syndrome, enteritis and pancreatitis, etc., diseases of the urinary and reproductive tract such as cystitis, overactive bladder and dysmenorrhea, etc., pruritus and other skin diseases comprising allergic dermatitis and burns, as well as osteoarthritis, etc.

Another object of the present invention is to provide a method for preparing the compound of formula (I), which can be achieved by the following steps:

Method I: when Y in ring A is N or C and meanwhile X is N in the compound of formula (I), the target molecule can be prepared by coupling a substituted amino acid with halogenated aromatic ring or halogenated heteroaromatic ring in the presence of cuprous iodide to prepare N-aromatic ring or N-heteroaromatic ring amino acid, which is further condensated with corresponding monosubstituted piperazine or 4-substituted piperidine.

wherein:

Preparation of the intermediate N-aromatic ring or N-heteroaromatic ring amino acid may also be achieved by preparing N-aromatic ring or N-heteroaromatic ring aminonitrile under the presence of acetic acid using the corresponding ketone, substituted aromatic amine or heteroaromatic amine, and trimethylsilyl cyanide as the raw materials, and then subjecting the same to basic hydrolysis;

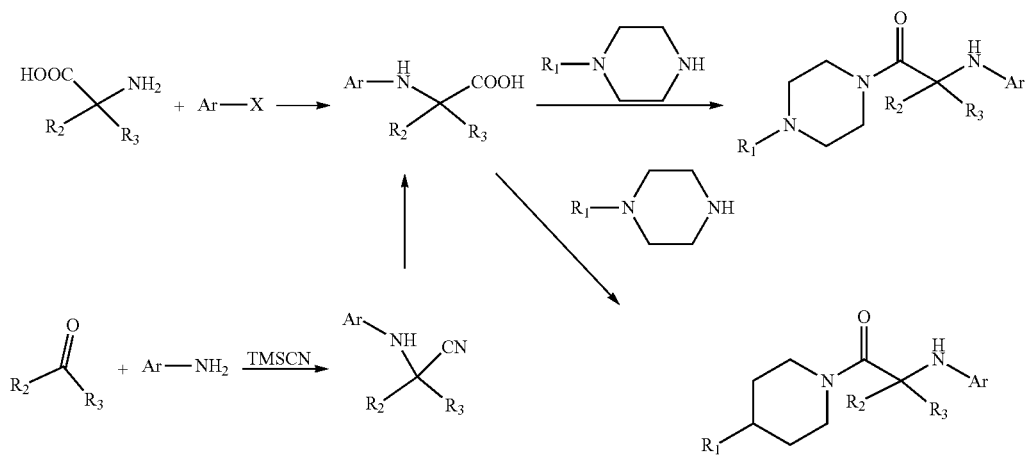

Preparation of the intermediate monosubstituted piperazine may be achieved by reacting bis-(2-chloroethyl)amine hydrochloride with corresponding aromatic amine; and may also be achieved by condensation between piperazine protected with $N^1$-Boc or piperazine and corresponding halide, and removing the Boc protecting group;

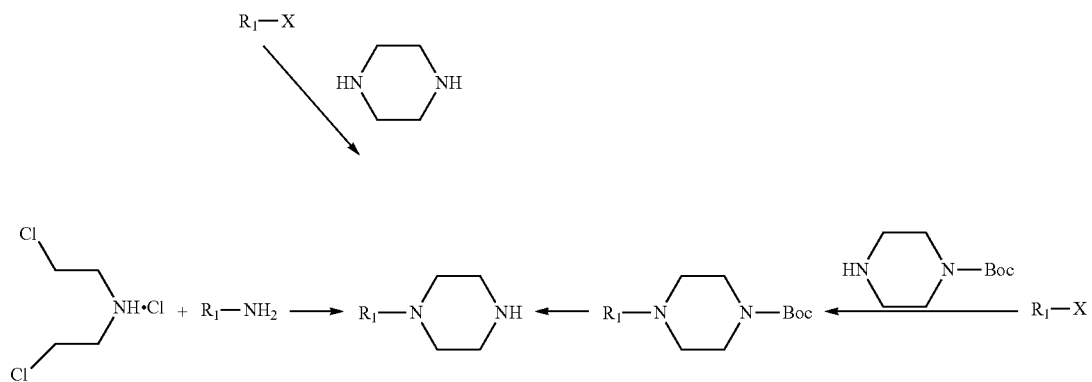

The above target molecule may also be prepared via similar methods when ring A is a nitrogen-containing bridged cyclic group for the target molecule.

Method II: when Y in ring A is N or C and meanwhile X is O or S in the compound of formula (I), the target molecule can be prepared by reacting α-halocarboxylic acid with phenol or thiophenol to prepare the corresponding aryloxy- or arylthio-acetic acid, and further condensing the same with corresponding monosubstituted piperazine or 4-substituted piperidine

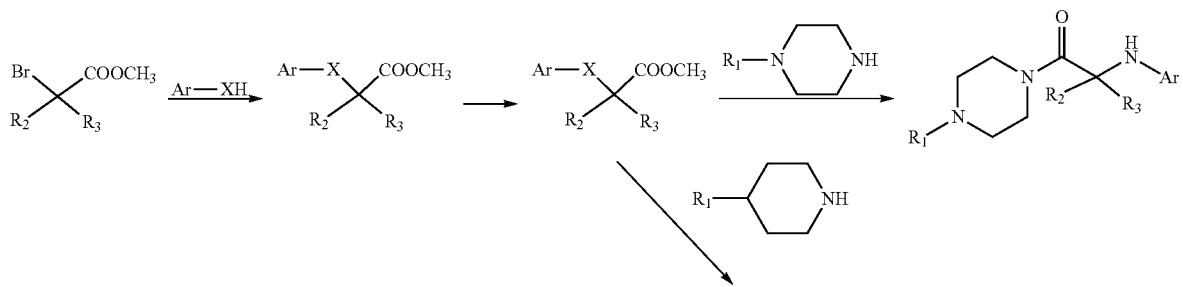

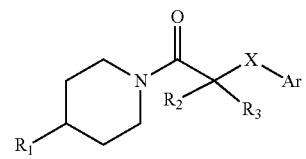

X = O, S

The above target molecule may also be prepared via similar methods when ring A is a nitrogen-containing bridged cyclic group for the target molecule.

The target molecule may be prepared according to method I or method II using indole-2-carboxylic acid, indoline-2-carboxylic acid, benzofuran-2-carboxylic acid, 2,3-dihydrobenzofuran-2-carboxylic acid and corresponding mono-substituted piperazine or 4-substituted piperidine as the raw materials, when $R_2$ is H or absent, $R_3$ and Ar are connected to form indolyl, indolinyl, benzofuranyl, 2,3-dihydrobenzofuranyl in the compound of formula (I).

The present invention further provides a medicament for treating diseases mediated by TRPA1, the medicament comprising the heteroaromatic acetamide compound shown in formula (I) or a pharmaceutically acceptable salt or a solvate thereof as the active component.

The present invention further provides a method for treating diseases mediated by TRPA1, comprising administering the heteroaromatic acetamide compound shown in formula (I) or a pharmaceutically acceptable salt or a solvate thereof in an effective amount to the subject in need of treatment for diseases mediated by TRPA1.

The present invention has experimentally confirmed that, the heteroaromatic acetamide compound of the present invention can selectively inhibit TRPA1 channel activity, and can be used to treat diseases mediated by TRPA1. The present invention further provides a medicament or a pharmaceutical composition comprising the compound.

DETAILED DESCRIPTION OF THE INVENTION

Figure 1:
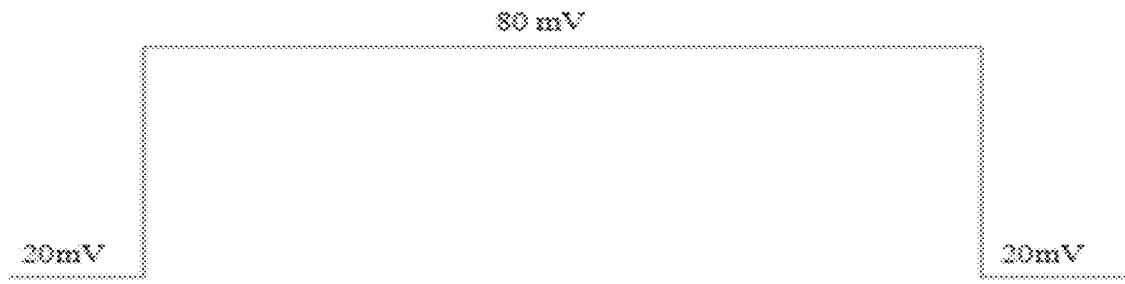
FIG. 1 is a diagram of TRPA1 testing voltage procedure.

The present invention will be further described in conjunction with the following examples, which only serve to specifically illustrate the present invention without limiting the present invention in any way. In addition, with regard to the apparatuses, intermediates, reagents, and so on as used in the examples, they are prepared according to methods commonly implemented in the art or can be purchased commercially unless there is specifically described.

I. Methods for Preparation of the Main Intermediates

1. Synthesis of the intermediate 1-(4-trifluoromethylphenyl)piperazine (A-1)

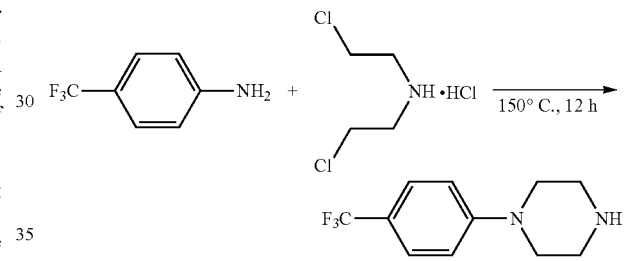

4-trifluoromethylaniline (9.37 g, 60 mmol) and bis(2-chloroethyl)amine hydrochloride (10.70 g, 60 mmol) were dissolved in 15 mL diethylene glycol monomethyl ether, heated to 150° C. under stirring and reacted for 12 hours. The reaction liquid was cooled to room temperature, adjusted to pH 8 with 15% $Na_2CO_3$ aqueous solution, and extracted with ethyl acetate (30 mL×2). The organic layers were combined, washed with saturated saline solution, dried over anhydrous sodium sulfate, filtered, and concentrated under reduced pressure to give A (111.88 g) with a yield of 86%, ESI-MS: m/z=231 $[M+1]^+$.

The intermediates A-2~A-7 listed in Table 1.1 were synthesized using corresponding halogenated heteroaromatic rings as the raw materials according to the same method as for preparation of A-1.

2. Synthesis of the intermediate 1-(5-(trifluoromethyl)pyridin-2-yl)piperazine (A-8)

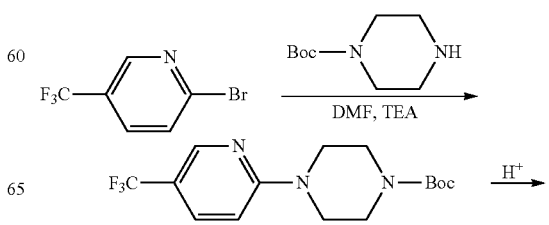

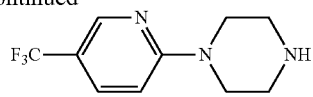

Step 1. Synthesis of tert-butyl 4-(5-(trifluoromethyl)pyridin-2-yl)piperazine-1-formate 2-bromo-5-trifluoromethylpyridine (11.25 g, 50.0 mmol) was dissolved in 100 mL dry DMF, followed by addition of triethylamine (10.1 mL, 100.0 mmol) and 1-Boc piperazine (11.2 mg, 60 mmol). The mixture was stirred at 80° C. to react for 12 hours, and the solvent was removed by evaporation under reduced pressure. The residue was dissolved in 140 mL DCM, washed sequentially with 80 mL water and 50 mL saturated saline solution, and dried over anhydrous Na$_2$SO$_4$. DCM was recovered from the resultant to obtain an off-white solid (13.74 g) with a yield of 83%, ESI-MS: m/z=332 [M+1]+.

Step 2. Synthesis of 1-(5-(trifluoromethyl)pyridin-2-yl)piperazine (A-8)

1-(5-(trifluoromethyl)pyridin-2-yl)piperazine (13.3 g, 40.0 mmol) was added into 150 mL 4N hydrochloric acid-dioxane solution and stirred under room temperature to react for 3 h, and the solvent was removed by evaporation under reduced pressure. The residue was adjusted to pH 8-9 with 15% Na$_2$CO$_3$ solution, and extracted twice with ethyl acetate. The organic layers were combined, washed sequentially with water and saturated NaCl aqueous solution, and dried over anhydrous Na$_2$SO$_4$ to obtain A-8 (8.42 g) with a yield of 91%, ESI-MS: m/z=232 [M+1]$^+$.

Intermediates A-9-A-20 listed in Table 1.1 were synthesized using corresponding halogenated heteroaromatic rings or halohydrocarbons as the raw materials according to the same method as for preparation of A-8.

TABLE 1.1

Structure and mass spectrometry data of intermediates A-2~A-7, A-9~A-20

| No. | Structure | MS(ESI) [M + 1]$^+$ |
|---|---|---|
| A-2 | 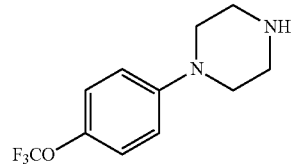 | 231 |
| A-3 | 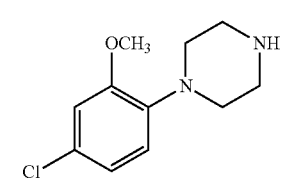 | 231 |
| A-4 | 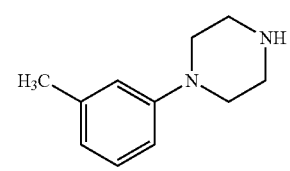 [SMILES: FC(F)(F)c1cccc(N2CCNCC2)c1] | 247 |
| A-5 | 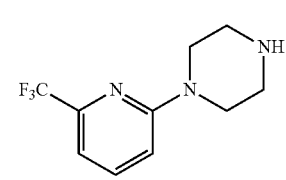 [SMILES: FC(F)(F)c1cccc(N2CCNCC2)n1] | 247 |
| A-6 | 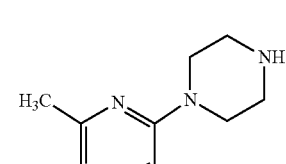 | 227 |
| A-7 | 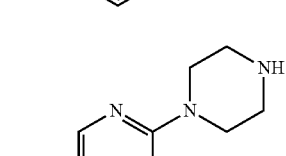 | 177 |
| A-9 | 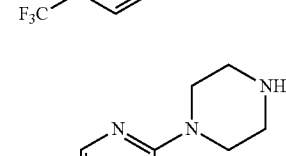 | 232 |
| A-10 | 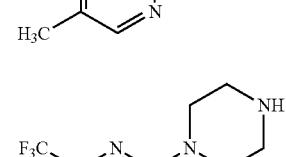 | 178 |
| A-11 | 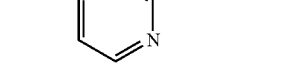 | 233 |
| A-12 | 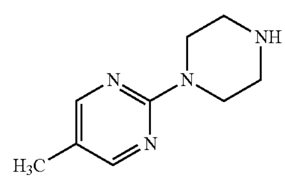 | 179 |
| A-13 | 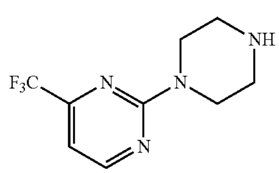 [SMILES: FC(F)(F)c1ccnc(N2CCNCC2)n1] | 233 |

TABLE 1.1-continued

Structure and mass spectrometry data of intermediates A-2~A-7, A-9~A-20

| No. | Structure | MS(ESI) [M + 1]⁺ |
|---|---|---|
| A-14 | 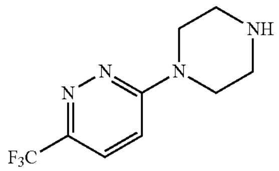 [SMILES: FC(F)(F)c1ccc(N2CCNCC2)nn1] | 233 |
| A-15 | 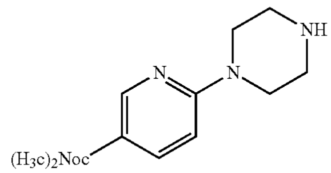 | 235 |
| A-16 | 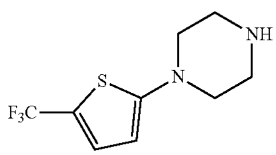 [SMILES: FC(F)(F)c1ccc(N2CCNCC2)s1] | 237 |
| A-17 | 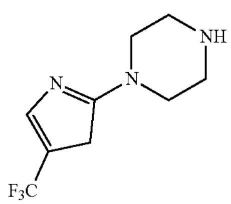 | 238 |
| A-18 | 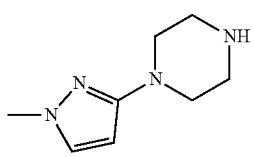 | 167 |
| A-19 | 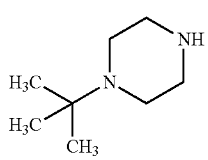 | 143 |
| A-20 | 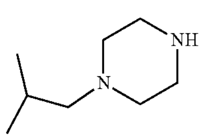 | 143 |

3. Synthesis of intermediate 1-((4-cyanophenyl)amino)cyclopentyl-1-formic acid (B-1)

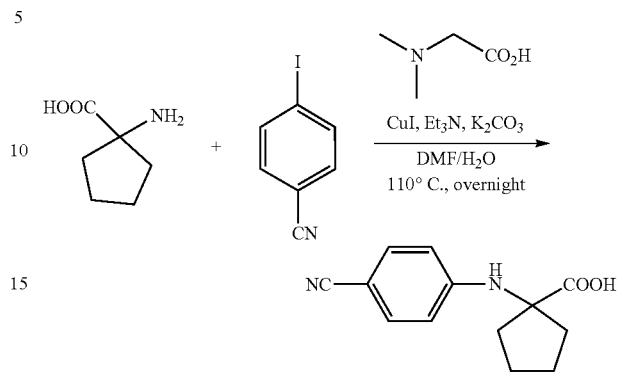

Synthesis steps: 1-aminocyclopentane-1-carboxylic acid (5.0 g, 32.9 mmol) and 4-iodobenzonitrile (11.33 g, 49.5 mmol) were dissolved in DMF/H$_2$O (60 mL, v/v=5/1) solution, and K$_2$CO$_3$ (13.6 g, 98.4 mmol), Et$_3$N (0.33 g, 3.29 mmol), CuI (1.25 g, 6.56 mmol) and N,N-dimethylglycine (6.56 mmol) were added thereto. The mixture was heated at 110° C. overnight, and cooled to room temperature. The reaction mixture was diluted with H$_2$O (500 mL), and adjusted to pH about 4.0 with 1.0N HCl aqueous solution. The resultant was extracted with EtOAc (150 mL×2), and the combined organic layers were washed with saturated saline solution (100 mL), dried over anhydrous sodium sulfate, filtered and concentrated. The obtained concentrate was separated by silica gel column chromatography (PE:EA:CH$_3$COOH=1.0:1.0:0.01) to obtain solid B-1 with a yield of 57.5%; ESI-MS: m/z=231 [M+H]⁺.

Intermediates B-2-B-18 in Table 1.2 were synthesized using corresponding α-amino acid and halogenated aromatic rings or halogenated heteroaromatic rings as raw materials according to the same method as for preparation of B-1.

TABLE 1.2

Structure and mass spectrometry data of intermediates B-2~B-18

| No. | Structure | MS(ESI) [M + 1]⁺ |
|---|---|---|
| B-2 | 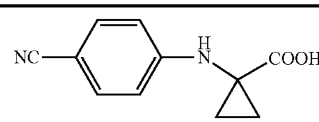 | 203 |
| B-3 | 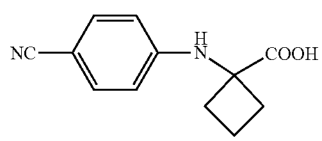 [SMILES: N#Cc1ccc(NC2(C(=O)O)CCC2)cc1] | 217 |
| B-4 | 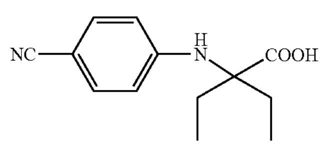 [SMILES: CCC(CC)(Nc1ccc(C#N)cc1)C(=O)O] | 233 |
| B-5 | 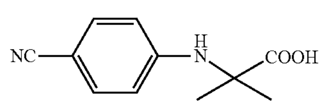 | 205 |

TABLE 1.2-continued

Structure and mass spectrometry data of intermediates B-2~B-18

| No. | Structure | MS(ESI) [M + 1]+ |
|---|---|---|
| B-6 | NC-, Cl-phenyl-NH-cyclopentane-COOH | 265 |
| B-7 | Cl-phenyl-NH-cyclopentane-COOH | 240 |
| B-8 | O$_2$N-phenyl-NH-cyclopentane-COOH | 251 |
| B-9 | NC-phenyl-NH-CH(tBu)-COOH (±) | 233 |
| B-10 | NC-phenyl-N(CH$_3$)-cyclopentane-COOH | 245 |
| B-11 | NC-thiazole-NH-cyclopentane-COOH | 238 |
| B-12 | NC-thiophene-NH-cyclopentane-COOH | 237 |
| B-13 | N-methylindole-NH-cyclopentane-COOH | 259 |
| B-14 | F$_3$C-phenyl-NH-cyclopentane-COOH | 274 |
| B-15 | NC-oxazole-NH-cyclopentane-COOH | 222 |
| B-16 | NC-N-methylimidazole-NH-cyclopentane-COOH | 235 |
| B-17 | NC-N-methylpyrrole-NH-cyclopentane-COOH | 234 |
| B-18 | NC-phenyl-NH-CH(Ph)-COOH (±) | 253 |

4. Synthesis of intermediate 1-(4-cyanophenoxy)cyclopentane-1-carboxylic acid (C-1)

[Reaction scheme: Methyl 1-bromocyclopentanecarboxylate + 4-cyanophenol → Cs$_2$CO$_3$, CH$_3$CN → Methyl 1-(4-cyanophenoxy)cyclopentane-1-carboxylate → 1) MeOH, NaOH; 2) HCl → 1-(4-cyanophenoxy)cyclopentane-1-carboxylic acid]

Step 1. Synthesis of Methyl 1-(4-cyanophenoxy)cyclopentane-1-carboxylate

Methyl 1-bromocyclopentanecarboxylate (10.0 g, 48.1 mmol), 0.61 g 4-cyanophenol (5.12 mmol), 3.84 g cesium carbonate (11.79 mmol) and 20 mL acetonitrile were added into a reaction flask to react under reflux for 6 h. After completion of the reaction, the solution was recovered under reduced pressure, and the residue was diluted with ethyl acetate (100 mL) and water (100 mL). The organic layer was separated and the aqueous layer was extracted with ethyl acetate (100 mL×2). The organic layers were combined, washed with saturated saline solution, dried over anhydrous sodium sulfate, filtered and concentrated under reduced pressure. The residue was purified by silica gel column chromatography (EA:PE=1:20) to obtain an oily substance (4.8 g) with a yield of 41.0%, ESI-MS: m/z=246 [M+H]$^+$.

Step 2. Synthesis of 1-(4-cyanophenoxy)cyclopentane-1-carboxylic acid (C-1)

Methyl 1-(4-cyanophenoxy)cyclopentane-1-carboxylate (4.8 g, 19.5 mmol) was dissolved in 100 mL methanol, followed by addition of 30 mL 15% $Na_2CO_3$ aqueous solution. The reaction mixture was stirred at room temperature for 6 hours, concentrated under reduced pressure, and the residual liquid was adjusted to pH=2 with 10% hydrochloric acid. The precipitate was filtered, washed with a small amount of water, and dried in vacuo to obtain powdered solid C-1 (3.8 g) with a yield of 85.0%, ESI-MS: m/z=232 [M+H]$^+$.

Intermediate C-2~C-13 in Table 1.3 were synthesized using the corresponding α-halogenated carboxylic acid and phenol or thiophenol as raw materials according to the same method as for preparation of C-1.

TABLE 1.3

Structure and mass spectrometry data of intermediate C-2~C-13

| No. | Structure | MS(ESI) [M + 1]$^+$ |
|---|---|---|
| C-2 | 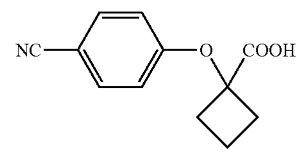 [SMILES: N#Cc1ccc(OC2(C(=O)O)CCC2)cc1] | 218 |
| C-3 | 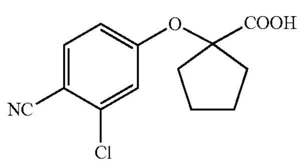 [SMILES: N#Cc1ccc(OC2(C(=O)O)CCCC2)cc1Cl] | 265 |
| C-4 | 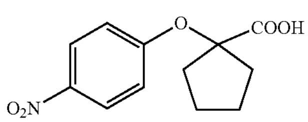 [SMILES: O=C(O)C1(Oc2ccc([N+](=O)[O-])cc2)CCCC1] | 251 |
| C-5 | 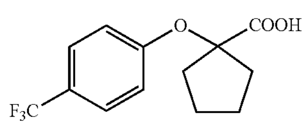 [SMILES: O=C(O)C1(Oc2ccc(C(F)(F)F)cc2)CCCC1] | 274 |
| C-6 | 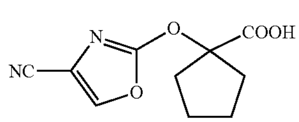 [SMILES: N#Cc1coc(OC2(C(=O)O)CCCC2)n1] | 222 |
| C-7 | 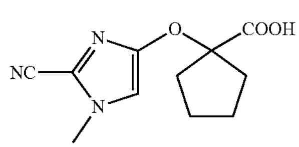 [SMILES: Cn1cc(OC2(C(=O)O)CCCC2)nc1C#N] | 235 |
| C-8 | 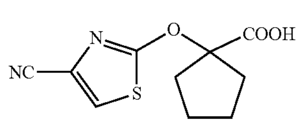 | 238 |
| C-9 | | 233 |
| C-10 | | 253 |
| C-11 | | 234 |
| C-12 | | 248 |
| C-13 | | 276 |

II. Preparation Examples of Target Compounds

Preparation Example 1. Synthesis of 4-((1-(4-(4-(trifluoromethyl)phenyl)piperazine-1-carbonyl)cyclopentyl)amino)benzonitrile (Compound 1)

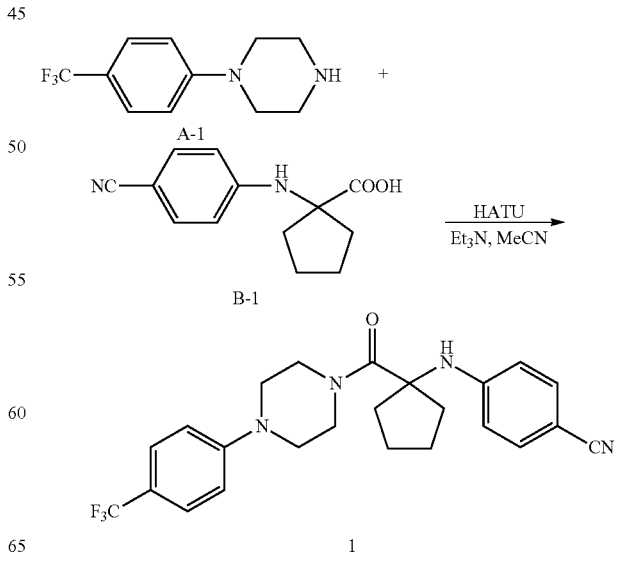

Synthetic steps: 1-(4-(trifluoromethyl)phenyl)piperazine (A-1, 43.7 mg, 0.19 mmol), 1-((4-cyanophenyl)amino)cyclopentyl-1-formic acid (B-1, 40.0 mg, 0.17 mmol), and anhydrous triethylamine (35.4 mg, 0.35 mmol) were dissolved in 5 mL anhydrous acetonitrile and 1 mL anhydrous DMF, followed by addition of 2-(7-oxybenzotriazole)-N,N,N',N'-tetramethylurea hexafluorophosphate (HATU) (68.4 mg, 0.18 mmol), and reaction was conducted at room temperature for 30 min. The mixture after completion of reaction was diluted with water, extracted with ethyl acetate, and washed sequentially with dilute hydrochloric acid, sodium bicarbonate solution, and saturated saline solution. The organic layer was dried over anhydrous sodium sulfate, filtered, and concentrated. The concentrate was separated via silica gel column chromatography (PE:EA=2:1, v/v) to obtain solid 1 with a yield of 95.5%; $^1$H NMR (500 MHz, CDCl$_3$) δ 7.47 (d, J=8.6 Hz, 2H), 7.40 (d, J=8.8 Hz, 2H), 6.84 (d, J=8.7 Hz, 2H), 6.60 (d, J=8.8 Hz, 2H), 4.38 (s, 1H), 4.04-3.72 (m, 4H), 3.24-2.96 (m, 4H), 2.56-2.59 (m, 2H), 1.94-1.89 (m, 2H), 1.84-1.75 (m, 4H); ESI-MS: m/z=443 [M+H]$^+$.

Compounds 2-9 in Table 2.1 were synthesized using the corresponding intermediate A and intermediate B as raw materials according to the same method as for preparation of Compound 1.

TABLE 2.1

NMR and mass spectrometry data of Compounds 2~9

| Compound No. of preparation examples | Name and structure of Compound | NMR and mass spectrometry data |
|---|---|---|
| Compound 2 | 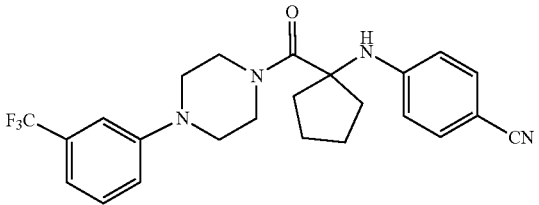 [SMILES: N#Cc1ccc(NC2(C(=O)N3CCN(c4cccc(C(F)(F)F)c4)CC3)CCCC2)cc1]<br>4-((1-(4-(3-(trifluoromethyl)phenyl)piperazine-1-carbonyl)cyclopentyl)amino)benzonitrile | $^1$HNMR (500 MHz, CDCl$_3$): δ7.46 (d, J = 8.7 Hz, 2H), 7.44 (dd, J = 8.6, 1H), 7.25 (d, J = 8.6 Hz, 1H),7.20 (s, 1H), 7.04 (d, J = 8.6 Hz, 1H), 6.85 (d, J = 8.7 Hz, 2H),4.36 (s, 1H), 4.02-3.70 (m, 4H), 3.29-3.18 (m, 4H), 2.62-2.59 (m, 2H), 1.95-1.90 (m, 2H), 1 83-1.76 (m, 4H); ESI-MS: m/z = 443 [M + H]$^+$. |
| Compound 3 | 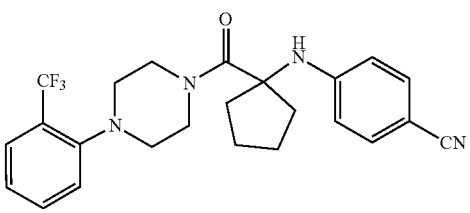 [SMILES: N#Cc1ccc(NC2(C(=O)N3CCN(c4ccccc4C(F)(F)F)CC3)CCCC2)cc1]<br>4-((1-(4-(2-(trifluoromethyl)phenyl)piperazine-1-carbonyl)cyclopentyl)amino)benzonitrile | $^1$HNMR (500 MHz, CDCl$_3$): δ7.47 (m, 3H), 7.21 (dd, J = 8.6, 1H), 6.98 (m, 1H), 6.85 (d, J = 8.7 Hz, 2H),6.55 (d, J = 8.6 Hz, 1H), 4.33 (s, 1H), 4.03-3.69 (m, 4H), 3.27-3.16 (m, 4H), 2.60-2.53(m, 2H), 1.95-1.84 (m, 2H), 1.82-1.73 (m, 4H); ESI-MS: m/z = 443 [M + H]$^+$. |
| Compound 4 | 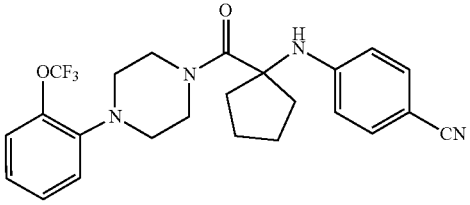 [SMILES: N#Cc1ccc(NC2(C(=O)N3CCN(c4ccccc4OC(F)(F)F)CC3)CCCC2)cc1]<br>4-((1-(4-(2-(trifluoromethoxy)phenyl)piperazine-1-carbonyl)cyclopentyl)amino)benzonitrile | $^1$HNMR (500 MHz, CDCl$_3$): δ7.46 (d, J = 8.7 Hz, 2H), 6.80-6.85 (m, 4H), 6.73 (d, J = 8.6 Hz, 1H), 6.70 (dd, J = 8.6 Hz, 1H), 4.35 (s, 1H), 3.82 (t, 4H), 3.20 (t, 4H), 2.63-2.59 (m, 2H), 1.94-1.90 (m, 2H), 1.82-1.77 (m, 4H); ESI-MS: m/z = 459 [M + H]$^+$. |

TABLE 2.1-continued

NMR and mass spectrometry data of Compounds 2~9

| Compound No. of preparation examples | Name and structure of Compound | NMR and mass spectrometry data |
|---|---|---|
| Compound 5 | 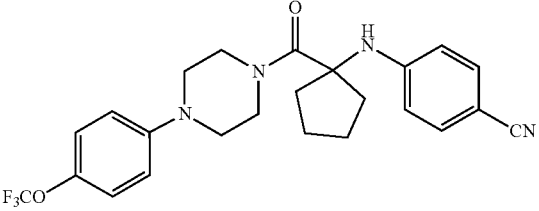 [SMILES: N#Cc1ccc(NC2(C(=O)N3CCN(c4ccc(OC(F)(F)F)cc4)CC3)CCCC2)cc1]<br>4-((1-(4-(4-(trifluoromethyl)phenyl)piperazine-1-carbonyl)cyclopentyl)amino)benzonitrile | $^1$HNMR (500 MHz, CDCl$_3$): δ7.47 (d, J = 8.6 Hz, 2H), 6.85 (d, J = 8.6 Hz, 2H), 6.73 (d, J = 8.7 Hz, 2H), 6.65 (d, J = 8.7 Hz, 2H), 4.45 (s, 1H), 3.94 (t, 4H), 3.18 (t, 4H), 2.63-2.60 (m, 2H), 1.94-1.90 (m, 2H), 1.82-1.75 (m, 4H); ESI-MS: m/z = 459 [M + H]$^+$. |
| Compound 6 | 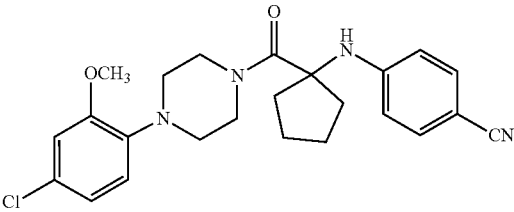 [SMILES: COc1cc(Cl)ccc1N1CCN(C(=O)C2(Nc3ccc(C#N)cc3)CCCC2)CC1]<br>4-((1-(4-(4-chloro-2-methoxyphenyl)piperazine-1-carbonyl)cyclopentyl)amino)benzonitrile | $^1$HNMR (500 MHz, CDCl$_3$): δ7.46 (d, J = 8.6 Hz, 2H), δ7.12 (s, 1H), 6.85 (d, J = 8.6 Hz, 2H), 6.80 (d, J = 8.7 Hz, 2H), 6.67 (d, J = 8.7 Hz, 2H), 4.37 (s, 1H), 4.00 (t, 4H), 3.86 (s, 3H), 3.29 (t, 4H), 2.63-2.60 (m, 2H), 1.95-1.90 (m, 2H), 1.84-1.77 (m, 4H); ESI-MS: m/z = 439 [M + H]$^+$. |
| Compound 7 | 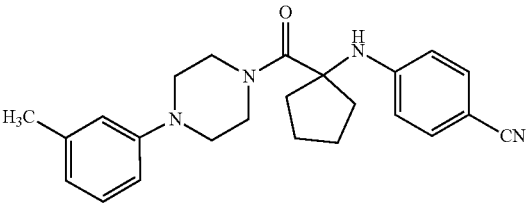 [SMILES: Cc1cccc(N2CCN(C(=O)C3(Nc4ccc(C#N)cc4)CCCC3)CC2)c1]<br>4-((1-(4-(3-methyl)phenyl)piperazine-1-carbonyl)cyclopentyl)amino)benzonitrile | $^1$HNMR (500 MHz, CDCl$_3$): δ7.47 (d, J = 8.7 Hz, 2H), δ7.15 (d, J = 8.6 Hz, 1H), 7.02 (dd, J = 8.6 Hz, 1H), 6.85 (d, J = 8.7 Hz, 2H), 6.80 (s, 1H), 6.47 (d, J = 8.6 Hz, 1H), 4.36 (s, 1H), 4.00 (t, 4H), 3.28 (t, 4H), 2 60-2.56 (m 2H) 2.27 (s 3H) 1 91-1 87 (m 2H) 1.83-1.77 (m, 4H); ESI-MS: m/z = 389 [M + H]$^+$. |
| Compound 8 | 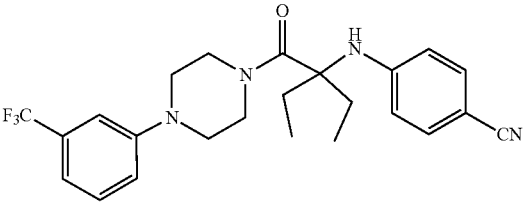 [SMILES: CCC(CC)(Nc1ccc(C#N)cc1)C(=O)N1CCN(c2cccc(C(F)(F)F)c2)CC1]<br>4-((3-(4-(3-trifluoromethyl)phenyl)piperazine-1-carbonyl)pentane-3-yl)amino)benzonitrile | $^1$HNMR (500 MHz, CDCl$_3$): δ7.47 (m, 3H), δ7.25 (d, J = 8.7 Hz, 1H), 7.20 (s, 1H), 7.07 (d, J = 8.7 Hz, 1H), 6.84 (d, J = 8.5 Hz, 2H), 4.40 (s, 1H), 3.91 (t, 4H), 3.29 (t, 4H), 1.75 (q, 4H), 0.90 (t, 6H); ESI-MS: m/z = 445 [M + H]$^+$. |

TABLE 2.1-continued

NMR and mass spectrometry data of Compounds 2~9

| Compound No. of preparation examples | Name and structure of Compound | NMR and mass spectrometry data |
|---|---|---|
| Compound 9 | 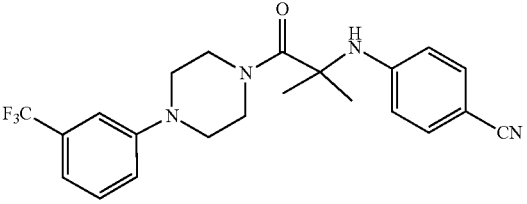<br>4-((3-(4-(3-trifluoromethyl)phenyl)piperazine-1-carbonyl)propane-2-yl)amino)benzonitrile | 1HNMR (500 MHz, CDCl$_3$): δ7.47 (m, 3H), δ7.25 (d, J = 8.7 Hz, 1H), 7.20 (s, 1H), 7.07 (d, J = 8.7 Hz, 1H), 6.84 (d, J = 8.5 Hz, 2H), 4.40 (s, 1H), 3.90 (t, 4H), 3.29 (t, 4H), 1.75 (q, 4H), 0.90 (t, 6H); ESI-MS: m/z = 445 [M + H]$^+$. |

Preparation Example 2. Synthesis of 4-((1-(4-(5-(trifluoromethyl)pyridin-2-yl) piperazine-1-carbonyl)cyclopentyl)amino)benzonitrile (Compound 10)

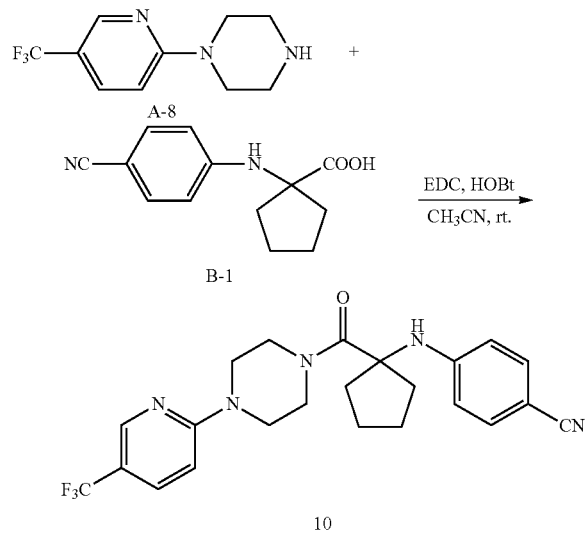

Synthetic steps: the intermediate B-1 (0.46 g, 2.0 mmol), EDC (0.28 g, 2.2 mmol) and HOBt (0.26 g, 2.0 mmol) were sequentially added into 20 nL anhydrous acetonitrile, and the mixture was stirred under room temperature for 30 min. Then, the intermediate A-8 was added and stirring was continued at room temperature for 12 hr. The solvent was removed under reduced pressure and the residue was dissolved with 40 mL ethyl acetate. The resultant was washed sequentially with saturated saline solution (2×10 mL), 10% citric acid (2×10 mL), saturated NaHCO$_3$ (2×10 mL) and water (2×10 mL). The organic layer was dried over anhydrous Na$_2$SO$_4$, filtered, concentrated, and the concentrate was separated by silica gel column chromatography (PE: EA=1.5:1, v/v) to obtain Compound 10 with a yield of 75%; $^1$H NMR (500 MHz, CDCl$_3$) δ8.52 (s, 1H), 8.04 (d, J=8.7 Hz, 1H), 7.42 (d, J=8.6 Hz, 2H), 6.86 (d, J=8.6 Hz, 2H), 6.63 (d, J=8.7 Hz, 1H), 4.39 (s, 1H), 3.89 (t, 4H), 3.64 (t, 4H), 2.60-2.57 (m, 2H), 1.95-1.90 (m, 2H), 1.84-1.77 (m, 4H); ESI-MS: rn/z=444 [M+H]$^+$.

Compounds 11-23 in Table 2.2 were synthesized using the corresponding intermediate A and intermediate B as raw materials according to the same method as for preparation of Compound 10.

TABLE 2.2

NMR and mass spectrometry data of Compounds 11~23

| Compound No. of preparation examples | Name of Compound | NMR and mass spectrometry data |
|---|---|---|
| Compound 11 | 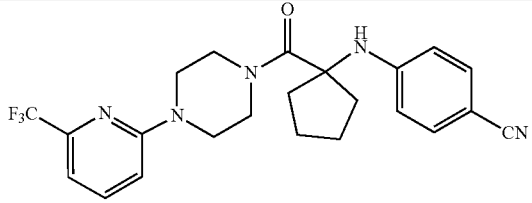 [SMILES: N#Cc1ccc(NC2(C(=O)N3CCN(c4cccc(C(F)(F)F)n4)CC3)CCCC2)cc1]<br>4-((1-(4-(6-(trifluoromethyl)pyridin-2-yl)piperazine-1-carbonyl)cyclopentyl)amino)benzonitrile | 1HNMR (500 MHz, CDCl$_3$): δ7.45 (m, 3H), 6.85 (d, J = 8.7 Hz, 2H),6.63 (d, J = 8.6 Hz, 1H),6.48 (d, J = 8.6 Hz, 1H),4.38 (s, 1H), 3.92 (t, 4H), 3.63 (t, 4H), 2.61-2.58 (m, 2H), 1.94-1.90 (m, 2H), 1.83-1.77 (m, ESI-MS: m/z = 444 [M + H]$^+$. |

TABLE 2.2-continued

NMR and mass spectrometry data of Compounds 11~23

| Compound No. of preparation examples | Name of Compound | NMR and mass spectrometry data |
|---|---|---|
| Compound 12 | 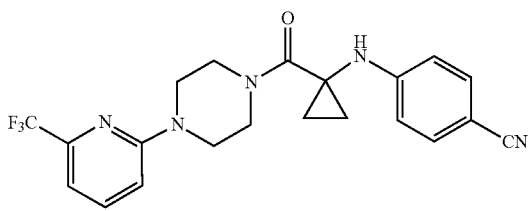 [SMILES: N#Cc1ccc(NC2(C(=O)N3CCN(c4cccc(C(F)(F)F)n4)CC3)CC2)cc1]<br>4-((1-(4-(6-(trifluoromethyl)pyridin-2-yl)piperazine-1-carbonyl)cyclopropyl)amino)benzonitrile | $^1$HNMR (500 MHz, CDCl$_3$): δ7.46 (m, 3H), 6.85 (d, J = 8.7 Hz, 2H), 6.62 (d, J = 8.6 Hz, 1H), 6.47 (d, J = 8.6 Hz, 1H), 4.37 (s, 1H), 3.93 (t, 4H), 3.63 (t, 4H), 1.05 (m, 2H), 0.78 (m, 2H);<br>ESI-MS: m/z = 416 [M + H]$^+$. |
| Compound 13 | 4-((1-(4-(6-(trifluoromethyl)pyridin-2-yl)piperazine-1-carbonyl)cyclobutyl)amino)benzonitrile | $^1$HNMR (500 MHz, CDCl$_3$): δ7.46 (m, 3H), 6.84 (d, J = 8.7 Hz, 2H), 6.63 (d, J = 8.6 Hz, 1H), 6.48 (d, J = 8.6 Hz, 1H), 4.38 (s, 1H), 3.95 (t, 4H), 3.61 (t, 4H), 2.2 (m, 4H), 1.68 (m, 2H);<br>ESI-MS: m/z = 430 [M + H]$^+$. |
| Compound 14 | 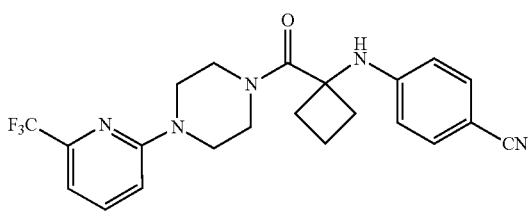 [SMILES: N#Cc1ccc(NC2(C(=O)N3CCN(c4cccc(C(F)(F)F)n4)CC3)CCC2)cc1]<br>(±)<br>4-((3,3-dimethyl-1-oxo-1-(4-(6-trifluoromethyl)pyridin-2-yl)piperazine-1-yl)butan-2-yl)amino)benzonitrile | $^1$HNMR (500 MHz, CDCl$_3$): δ7.45 (m, 3H), 6.84 (d, J = 8.6 Hz, 2H), 6.62 (d, J = 8.6 Hz, 1H), 6.48 (d, J = 8.6 Hz, 1H), 4.38 (s, 1H), 3.92 (t, 4H), 3.43 (t, 4H), 3.27 (s, 1H), 0.94 (s, 9H);<br>ESI-MS: m/z = 446 [M + H]$^+$. |
| Compound 15 | 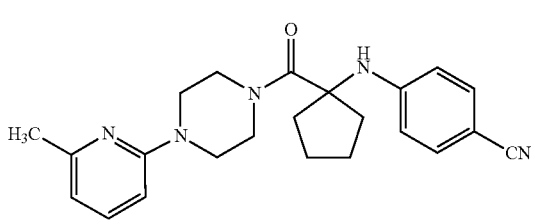 [SMILES: Cc1cccc(N2CCN(C(=O)C3(Nc4ccc(C#N)cc4)CCCC3)CC2)n1]<br>4-((1-(4-(6-methylpyridin-2-yl)piperazine-1-carbonyl)cyclopentyl)amino)benzonitrile | $^1$HNMR (500 MHz, CDCl$_3$): δ7.43 (m, 3H), 6.85 (d, J = 8.6 Hz, 2H), 6.47 (d, J = 8.6 Hz, 1H), 6.30 (d, J = 8.7 Hz, 1H), 4.39 (s, 1H), 3.91 (t, 4H), 3.64 (t, 4H), 2.62-2.59 (m, 2H), 2.46 (s, 3H), 1.95-1.90 (m, 2H), 1.83-1.76 (m, 4H);<br>ESI-MS: m/z = 390 [M + H]$^+$ |

TABLE 2.2-continued

NMR and mass spectrometry data of Compounds 11~23

| Compound No. of preparation examples | Name of Compound | NMR and mass spectrometry data |
|---|---|---|
| Compound 16 | 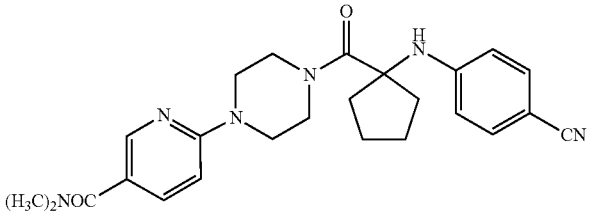 6-(4-(1-((4-cyano-phenyl)amino)cyclopentane-1-carbonyl)piperazine-1-yl)N,N-dimethylnicotinamide | $^1$HNMR (500 MHz, CDCl$_3$): δ8.32 (s, 1H), 7.87 (d, J = 8.7 Hz, 1H),7.45 (d, J = 8.6 Hz, 2H),6.85 (m, 3H), 4.37 (s, 1H), 3.93 (t, 4H), 3.56 (t, 4H), 2.93 (s, 6H), 2.61-2.58 (m, 2H), 1.94-1.90 (m, 2H), 1.83-1.77 (m, 4H); ESI-MS: m/z = 447 [M + H]$^+$ |
| Compound 17 | 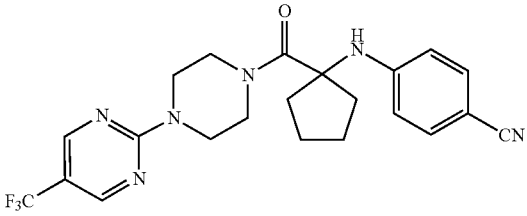 [SMILES: N#Cc1ccc(NC2(C(=O)N3CCN(c4ncc(C(F)(F)F)cn4)CC3)CCCC2)cc1] 4-((1-(4-(5-(trifluoromethyl)pyrimidin-2-yl)piperazine-1-carbonyl)cyclopentyl)amino)benzonitrile | $^1$HNMR (500 MHz, CDCl$_3$): δ8.57 (s, 2H), 7.45 (d, J = 8.6 Hz, 2H),6.85 (d, J = 8.6 Hz, 2H), 4.38 (s, 1H), 3.92 (t, 4H), 3.57 (t, 4H), 2.60-2.57 (m, 2H),1.93-1.90 (m, 2H), 1.82-1.77 (m, 4H); ESI-MS: m/z = 445 [M + H]$^+$ |
| Compound 18 | 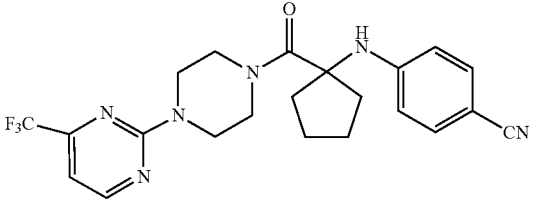 [SMILES: N#Cc1ccc(NC2(C(=O)N3CCN(c4nccc(C(F)(F)F)n4)CC3)CCCC2)cc1] 4-((1-(4-(4-(trifluoromethyl)pyrimidin-2-yl)piperazine-1-carbonyl)cyclopentyl)amino)benzonitrile | $^1$HNMR (500 MHz, CDCl$_3$): δ8.29 (d, J = 8.8 Hz, 1H), 7.45 (d, J = 8.6 Hz, 2H),6.86 (d, J = 8.6 Hz, 2H),6.92 (d, J = 8.8 Hz, 1H),4.38 (s, 1H), 3.96 (t, 4H), 3.62 (t, 4H), 2.61-2.58 (m, 2H),1.92-1.89 (m, 2H), 1.83-1.77 (m, 4H); ESI-MS: m/z = 445 [M + H]$^+$ |
| Compound 19 | 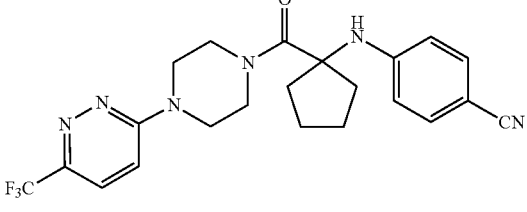 4-((1-(4-(6-(trifluoromethyl)pyridazin-3-yl)piperazine-1-carbonyl)cyclopentyl)amino)benzonitrile | $^1$HNMR (500 MHz, CDCl$_3$): δ7.45 (d, J = 8.6 Hz, 2H),7.04 (d, J = 8.8 Hz, 1H),6.86 (d, J = 8.6 Hz, 2H),6.70 (d, J = 8.8 Hz, 1H), 4.39 (s, 1H), 3.97 (t, 4H), 3.64 (t, 4H), 2.60-2.57 (m, 2H),1.93-1.90 (m, 2H), 1.83-1.77 (m, 4H); ESI-MS: m/z = 445 [M + H]$^+$ |

TABLE 2.2-continued

NMR and mass spectrometry data of Compounds 11~23

| Compound No. of preparation examples | Name of Compound | | NMR and mass spectrometry data |
|---|---|---|---|
| Compound 20 | 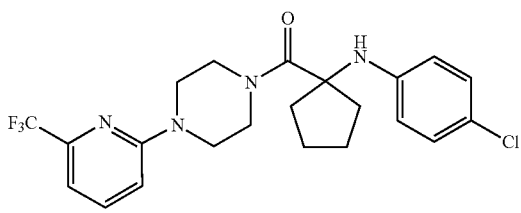 [SMILES: O=C(N1CCN(c2cccc(C(F)(F)F)n2)CC1)C1(Nc2ccc(Cl)cc2)CCCC1] 4-((1-(4-(6-(trifluoromethyl)pyridazin-3-yl)piperazine-1-carbonyl)cyclopentyl)amino)chlorobenzene | | $^1$HNMR (500 MHz, CDCl$_3$): δ7.43 (m, 1H), 7.03 (d, J = 8.7 Hz, 2H),6.60 (m, 3H), 6.47 (d, J = 8.6 Hz, 1H),4.37 (s, 1H), 3.87 (t, 4H), 3.58 (t, 4H), 2.61-2.58 (m, 2H),1.95-1.90 (m, 2H), 1.84-1.78 (m, 4H); ESI-MS: m/z = 453 [M + H]$^+$ |
| Compound 21 | 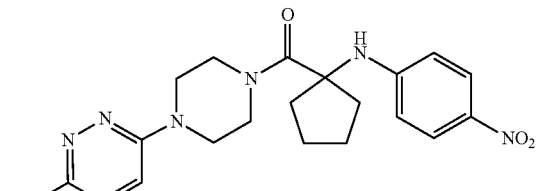 4-((1-(4-(6-(trifluoromethyl)pyridazin-3-yl)piperazine-1-carbonyl)cyclopentyl)amino)nitrobenzene | | $^1$HNMR (500 MHz, CDCl$_3$): δ8.00 (d, J = 8.7 Hz, 2H), 7.04 (d, J = 8.8 Hz, 1H),6.70 (m, 3H), 4.39 (s, 1H), 3.97 (t, 4H), 3.64 (t, 4H), 2.60-2.57 (m, 2H),1.93-1.90 (m, 2H), 1.83-1.77 (m, 4H); ESI-MS: m/z = 453 [M + H]$^+$ |
| Compound 22 | 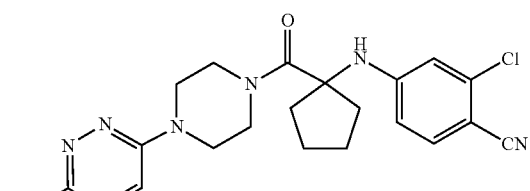 2-chloro-4-((1-(4-(6-(trifluoromethyl)pyridazin-3-yl)piperazine-1-carbonyl)cyclopentyl)amino)benzonitrile | | $^1$HNMR (500 MHz, CDCl$_3$): δ7.44 (s, 1H), 7.04 (m, 2H),6.73 (m, 2H), 4.40 (s, 1H), 3.96 (t, 4H), 3.60 (t, 4H), 2.61-2.58 (m, 2H),1.93-1.90 (m, 2H), 1.82-1.76 (m, 4H); ESI-MS: m/z = 479 [M + H]$^+$ |
| Compound 23 | 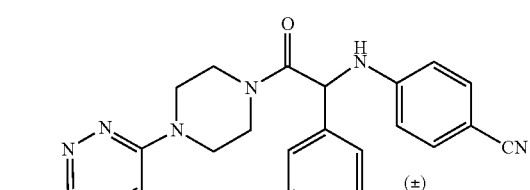 2-chloro-4-((1-(4-(6-(trifluoromethyl)pyridazin-3-yl)piperazine-1-carbonyl)phenyl)amino)benzonitrile | | $^1$HNMR (500 MHz, CDCl$_3$): δ7.42(d, J = 8.7Hz, 2H), 7.31-7.27 (m, 5H),7.04 (d, J = 8.6 Hz, 1H), 6.85 (d, J = 8.7 Hz, 2H),6.70 (d, J = 8.6 Hz, 1H), 4.84 (s, 1H), 4.39 (s, 1H), 3.97 (t, 4H), 3.61 (t, 4H), 2.60-2.57 (m, 2H),1.92-1.89 (m, 2H), 1.81-1.75 (m, 4H); ESI-MS: m/z = 467 [M + H]$^+$ |

Preparation Example 3. Synthesis of 4-((1-(4-(5-(trifluoromethyl)thien-2-yl) piperazine-1-carbonyl)cyclopentyl)amino)benzonitrile (Compound 24)

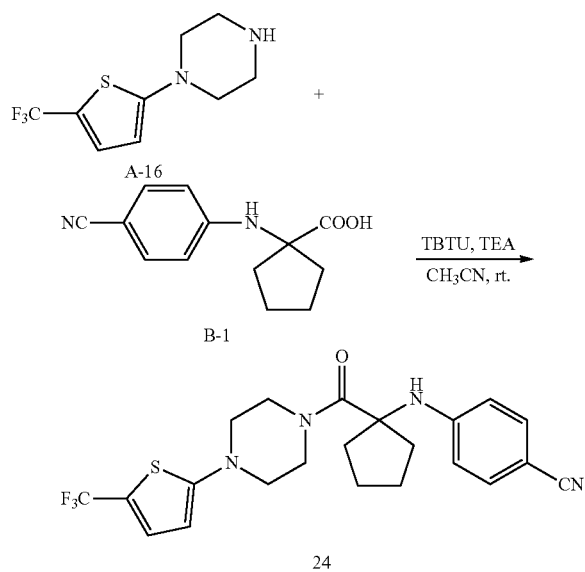

Synthetic steps: the intermediate B-1 (0.46 g, 2.0 mmol), TEA (0.29 g, 4.0 mmol) and TBTU (0.71 g, 2.2 mmol) were added respectively into 30 nL anhydrous acetonitrile, and the mixture was stirred under room temperature for 30 min. Then, the intermediate A-16 (0.47 g, 2.0 mmol) was added and stirring was continued at room temperature for 0.5 hr. The solvent was removed under reduced pressure and the residue was dissolved with ethyl acetate (40 mL). The resultant was washed sequentially with water (2×10 mL) and saturated saline solution (2×10 mL). The organic layer was dried over anhydrous $Na_2SO_4$, filtered, concentrated, and the concentrate was separated by silica gel column chromatography (PE:EA=2:3 v/v) to obtain Compound 24 (0.77 g) with a yield of 86%; $^1$H NMR (500 MHz, $CDCl_3$): δ7.42 (d, J=8.6 Hz, 2H), 6.86 (d, J=8.6 Hz, 2H), 6.63 (d, 1H), 5.80 (d, 1H), 4.39 (s, 1H), 3.56 (t, 4H), 3.32 (t, 4H), 2.62-2.59 (m, 2H), 1.95-1.91 (m, 2H), 1.85-1.78 (m, 4H); ESI-MS: m/z=449 [M+H]$^+$.

Preparation Example 4. Synthesis of 4-((1-(4-(5-(trifluoromethyl)thiazol-2-yl)piperazine-1-carbonyl)cyclopentyl)amino)benzonitrile (Compound 25)

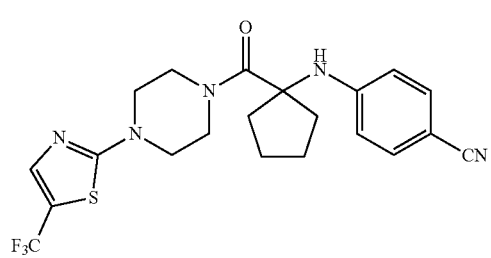

Example 3 was referred to for the synthetic steps for preparation of Compound 25 except that the intermediate A-17 and the intermediate B-1 were used as raw materials, and the yield was 83%; $^1$HNMR (500 MHz, $CDCl_3$): δ7.43 (d, J=8.6 Hz, 2H), 6.87 (d, J=8.6 Hz, 2H), 6.78 (s, 1H), 4.40 (s, 1H), 3.60 (t, 4H), 3.33 (t, 4H), 2.63-2.60 (m, 2H), 1.94-1.90 (m, 2H), 1.84-1.77 (m, 4H); ESI-MS: m/z=450 [M+H]$^+$.

Preparation Example 5. Synthesis of 4-((1-(4-(1-methyl-1H-pyrazol-3-yl)piperazine-1-carbonyl)cyclopentyl)amino)benzonitrile (Compound 26)

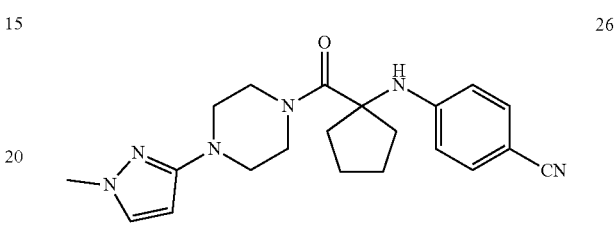

Example 3 was referred to for the synthetic steps for preparation of Compound 26 except that the intermediate A-18 and the intermediate B-1 were used as raw materials, and the yield was 76%; $^1$HNMR (500 MHz, $CDCl_3$): δ7.81 (d, J=7.8 Hz, 1H), 7.43 (d, J=8.7 Hz, 2H), 6.85 (d, J=8.7 Hz, 2H), 6.66 (d, J=7.8 Hz, 1H), 4.40 (s, 1H), 3.95 (s, 3H), 3.78 (t, 4H), 3.56 (t, 4H), 2.61-2.58 (m, 2H), 1.94-1.91 (m, 2H), 1.856-1.78 (m, 4H); ESI-MS: m/z=379 [M+H]$^+$.

Preparation Example 6. Synthesis of 4-((1-(4-(6-(trifluoromethyl)pyridin-2-yl)piperazine-1-carbonyl)cyclopentyl)amino)phenylacetylene (Compound 27)

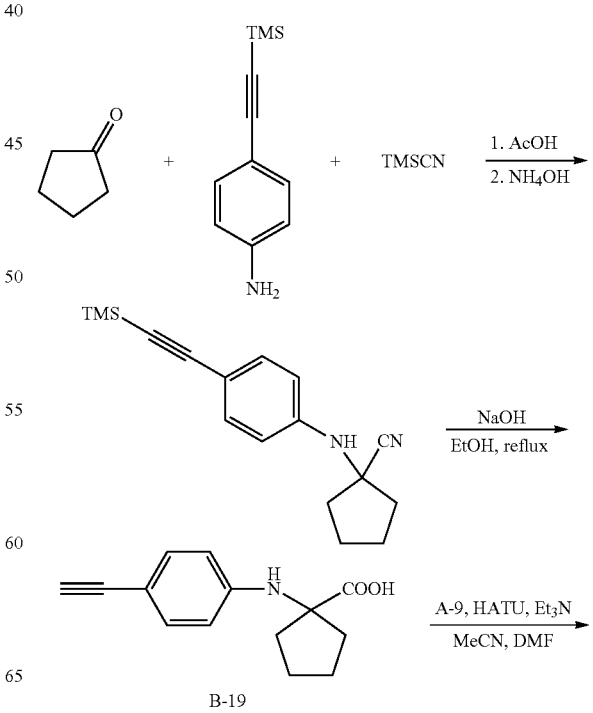

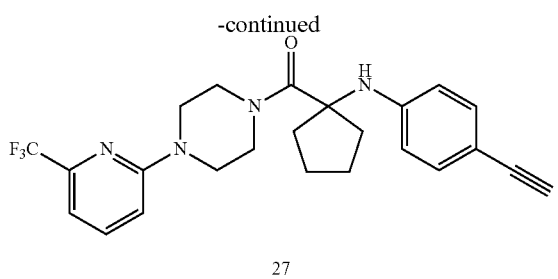

27

Step 1. Synthesis of 1-((4-((trimethylsilyl)ethynyl) phenyl)amino)cyclopentane-1-carbonitrile Cyclopentanone (2.5 g, 30.0 mmol) was added into 30 ml acetic acid solution, and the mixture was cooled to 0° C. in an ice bath followed by addition of 4-trimethylsilanylethynyl-phenylamine (6.06 g, 32.0 mmol). The mixture was stirred for 15 minutes and then added with trimethylsilyl cyanide (2.98 g, 30 mmol) and stirred overnight at room temperature. Then, the reaction solution was poured slowly into crushed ice-ammonium hydroxide solution, stirred for 20 minutes, and extracted with $CH_2Cl_2$ (50 mL×2). The organic layers were combined, washed with saturated saline solution, dried over anhydrous $Na_2SO_4$, filtered, and concentrated, and the concentrate was separated by silica gel column chromatography (PE:EA=4:1 v/v) to obtain an oily substance (7.54 g) with a yield of 89%, ESI-MS:m/z=283 $[M+1]^+$.

Step 2. Synthesis of 1-((4-ethynyl)phenyl)amino) cyclopentane-1-carboxylic acid (B-19)

1-(4-trimethylsilanylethynylphenyl)aminocyclopentan-ecarbonitrile (7.06 g, 25.0 mmol) was added into 4N sodium hydroxide in 30 mL ethanol solution, and the mixture was heated to reflux overnight under a nitrogen atmosphere. Then, the mixture was poured into ice slowly, adjusted to pH 3-4 with hydrochloric acid, and extracted with ethyl acetate. The ethyl acetate phases were combined, washed with water and saturated saline solution, dried over anhydrous $Na_2SO_4$, filtered, and concentrated. A small amount of dichloromethane was added thereto to allow precipitation of crystals and filtration was conducted to collect solids, obtaining 1-(4-ethynylphenyl)aminocyclopentane-1-carboxylic acid (B-19, 4.8 g) with a yield of 85%, ESI-MS:m/z=230$[M+1]^+$.

Step 3. Synthesis of 4-((1-(4-(6-(trifluoromethyl) pyridin-2-yl)piperazine-1-carbonyl)cyclopentyl) amino)phenylacetylene (Compound 27)

Example 3 was referred to for the synthetic steps for preparation of Compound 27 except that the intermediates A-9 and B-19 were used as raw materials, and the yield was 81%; $^1$HNMR (500 MHz, CDCl$_3$): 57.45 (m, 3H), 6.64 (m, 3H), 6.48 (d, J=8.6 Hz, 1H), 4.39 (s, 1H), 3.79 (t, 4H), 3.57 (t, 4H), 2.82 (s, 1H), 2.60-2.57 (m, 2H), 1.95-1.92 (m, 2H), 1.86-1.77 (m, 4H); ESI-MS: m/z=443 $[M+H]^+$.

Preparation Example 7. Synthesis of 4-((1-(8-(6-(trifluoromethyl)pyridin-2-yl)-3,8-diazabicyclo [3.2.1]octane-3-carbonyl)cyclopentyl)amino)benzo-nitrile (Compound 28)

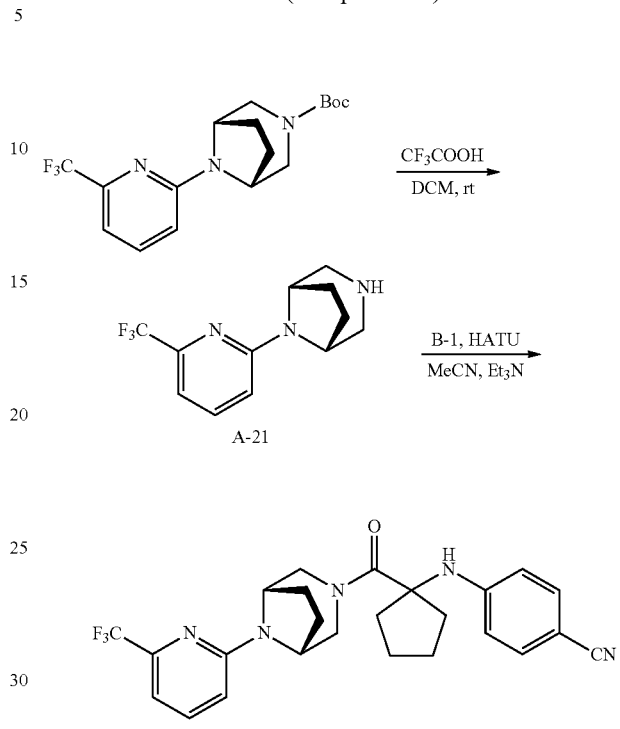

28

Step 1. Synthesis of 8-(6-(trifluoromethyl)pyridin-2-yl)-3,8-diazabicyclo[3.2.1]octane 3-Boc-8-(6-(trifluoromethyl)pyridin-2-yl)-3,8-diazabicy-clo[3.2.1]octane (54.0 mg, 0.15 mmol) was dissolved in 5 mL DCM, and trifluoroacetic acid (1.03 g, 9.0 mmol) was added to allow reaction at room temperature for 1 h. After completion of the reaction, the resultant was neutralized by addition of sodium bicarbonate solution, extracted with ethyl acetate. The organic layer was dried over $Na_2SO_4$, filtered, and concentrated, and the concentrate was purified by silica gel column chromatography (DCM:MeOH=15:1, v/v) to obtain solid A-21 (20.7 mg) with a yield of 53.6%. ESI-MS: m/z=258 $[M+H]^+$.

Step 2. Synthesis of 4-((1-(8-(6-(trifluoromethyl) pyridin-2-yl)-3,8-diazabicyclo[3.2.1]octane-3-carbo-nyl)cyclopentyl)amino)benzonitrile (Compound 28)

Example 3 was referred to for the synthetic steps for preparation of Compound 28 except that the intermediates A-21 and B-1 were used as raw materials, and the yield was 84%; $^1$HNMR (500 MHz, CDCl$_3$): δ 7.62-7.53 (m, 3H), 6.99-6.93 (m, 3H), 6.70 (d, J=8.5 Hz, 1H), 4.64-4.53 (m, 1H), 4.52-4.45 (m, 1H), 4.39 (s, 1H), 4.26-4.16 (m, 2H), 3.34-3.25 (m, 1H), 3.04-2.96 (m, 1H), 2.75-2.64 (m, 1H), 2.34-2.23 (m, 1H), 2.22-2.14 (m, 1H), 2.14-2.04 (m, 1H), 1.93-1.64 (m, 6H), 1.48-1.41 (m, 1H), 1.10-0.99 (m, 1H); ESI-MS: m/z=470 $[M+H]^+$.

Preparation Example 8. Synthesis of 4-((1-(5-(6-(trifluoromethyl)pyridin-2-yl)-2,5-diazabicyclo[2.2.2]octane-2-carbonyl)cyclopentyl)amino)benzonitrile (Compound 29)

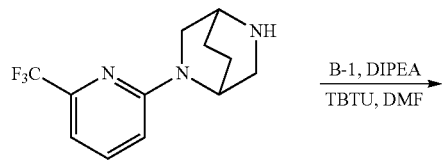

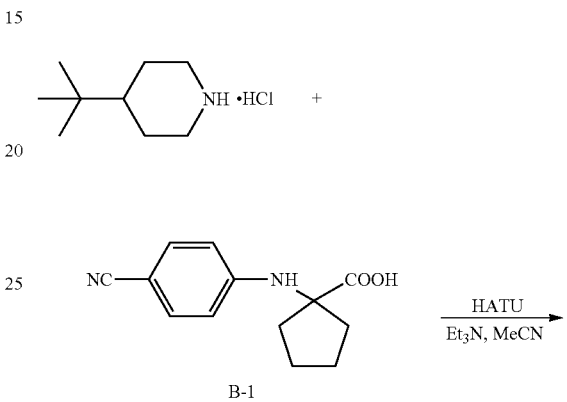

Synthetic steps: the intermediate B-1 (0.46 g, 2.0 mmol), DIPEA (0.78 g, 6.0 mmol) and TBTU (0.71 g, 2.2 mmol) were added respectively into 15 mL anhydrous DMF, stirred at 0° C. for 30 min, and then added with the intermediate 2-(6-(trifluoromethyl)pyridine-2-yl)-2,5-diazabicyclo[2.2.2]octane (0.50 g, 2.0 mmol). Stirring was continued at room temperature for 5 hr. The solvent was removed under reduced pressure, and the residue was dissolved in 40 mL ethyl acetate, washed with water (2×10 mL) and saturated saline solution (2×10 mL) sequentially. The organic layer was dried over anhydrous Na$_2$SO$_4$, filtered, and concentrated, and the concentrate was separated by silica gel column chromatography (PE:EA=2:3 v/v) to obtain Compound 29 (0.7 g) with a yield of 75%; 1H NMR (500 MHz, CDCl$_3$): 57.62-7.58 (m, 3H), 6.98-6.93 (m, 3H), 6.70 (d, J=8.6 Hz, 1H), 4.62-4.58 (m, 2H), 4.53-4.47 (m, 1H), 4.40 (s, 1H), 4.27-4.18 (m, 1H), 3.34-3.02 (m, 2H), 2.76-2.54 (m, 2H), 2.24-2.06 (m, 2H), 1.93-1.66 (m, 6H), 1.38-1.41 (m, 1H), 1.12-0.98 (m, 1H); ESI-MS: m/z=470 [M+H]$^+$.

Preparation Example 9. Synthesis of 4-((1-(4-(cyclopentanemethyl)piperazine-1-carbonyl)cyclopentyl)amino)benzonitrile (Compound 30)

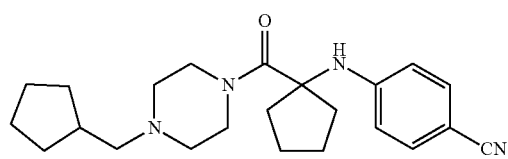

Example 3 was referred to for the synthetic steps for preparation of Compound 30 except that 1-(cyclopentanemethyl)piperazine and the intermediate B-1 were used as raw materials, and the yield was 72%; $^1$HNMR (500 MHz, CDCl$_3$): 57.40 (d, J=8.6 Hz, 2H), 6.60 (d, J=8.6 Hz, 2H), 4.40 (s, 1H), 3.43-3.37 (m, 4H), 2.48-2.42 (m, 4H), 2.55-2.26 (m, 6H), 1.97-1.82 (m, 5H), 1.86-1.60 (m, 8H); ESI-MS: m/z=381 [M+H]$^+$.

Preparation Example 10. Synthesis of 4-((1-(4-(tert-butyl)piperidine-1-carbonyl)cyclopentyl)amino)benzonitrile (Compound 31)

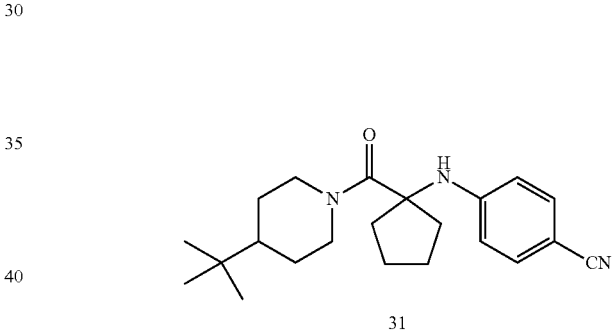

Synthetic steps: 4-(tert-butyl)piperidine hydrochloride (0.65 g, 3.7 mmol), B-1 (0.78 g, 3.4 mmol), and anhydrous triethylamine (1.21 g, 12 mmol) were dissolved in 30 mL anhydrous acetonitrile, and then added with HATU (1.48 g, 3.9 mmol) to react under room temperature for 30 min. After completion of reaction, the resultant was diluted with water, extracted with ethyl acetate, washed with dilute hydrochloric acid, sodium bicarbonate solution and saturated saline solution. The organic layer was dried over anhydrous Na$_2$SO$_4$, filtered, and concentrated, and the concentrate was purified by silica gel column chromatography (PE:EA=2:1) to obtain solid 31 (1.09 g) with a yield of 90.8%0 $^1$H NMR (500 MHz, CDCl$_3$): δ 7.39 (d, J=8.8 Hz, 2H), 6.58 (d, J=8.9 Hz, 2H), 4.78-4.60 (m, 1H), 4.55-4.41 (m, 1H), 4.38 (s, 1H), 2.96-2.77 (m, 1H), 2.77-2.55 (m, 1H), 2.53-2.28 (m, 2H), 1.97-1.85 (m, 2H), 1.84-1.69 (m, 4H), 1.55-1.40 (m, 2H), 1.19-1.05 (m, 1H), 1.02-0.75 (m, 2H), 0.69 (s, 9H); ESI-MS: m/z=354 [M+H]$^+$.

Compounds 32 to 46 in Table 2.3 were synthesized using the corresponding 4-substituted piperidine or 4-substituted piperazine and the intermediate B as raw materials according to the same method as for preparation of Compound 33.

TABLE 2.3

NMR and mass spectrometry data of Compounds 32~46

| Compound No. of preparation examples | Name of Compound | NMR and mass spectrometry data |
|---|---|---|
| Compound 32 | 4-((1-(4-(isobutyl)piperidine-1-carbonyl)cyclopentyl)amino)benzonitrile | $^1$HNMR (500 MHz, CDCl$_3$): δ7.40 (d, J = 8.8 Hz, 2H), 6.59 (d, J = 8.8 Hz, 2H), 4.74-4.62 (m, 1H), 4.55-4.41 (m, 1H), 4.39 (s, 1H), 2.95-2.78 (m, 1H), 2.72-2.56 (m, 1H), 2.52-2.38 (m, 2H), 1.97-1.88 (m, 2H), 1.80-1.71 (m, 4H), 1.65-1.58 (m, 2H), 1.55-1.44 (m, 1H), 1.19-1.06 (m, 4H), 0.90 (s, 6H); ESI-MS: m/z = 354 [M + H]$^+$. |
| Compound 33 | 4-((1-(4-(cyclopentyl)piperidine-1-carbonyl)cyclopentyl)amino)benzonitrile | $^1$HNMR (500 MHz, CDCl$_3$): δ7.39 (d, J = 8.8 Hz, 2H), 6.56 (d, J = 8.8 Hz, 2H), 4.73-4.64 (m, 1H), 4.56-4.42 (m, 1H), 4.40 (s, 1H), 2.95-2.78 (m, 1H), 2.72-2.56 (m, 1H), 2.52-2.38 (m, 2H), 1.97-1.88 (m, 4H), 1.80-1.71 (m, 4H), 1.65-1.58 (m, 4H), 1.55-1.44 (m, 2H), 1.31-1.25 (m, 2H), 1.19-1.06 (m, 4H); ESI-MS: m/z = 366 [M + H]$^+$. |
| Compound 34 | 4-((1-(8-aza-spiro[4.5]decane-8-carbonyl)cyclopentyl)amino)benzonitrile | $^1$HNMR (500 MHz, CDCl$_3$): δ7.40 (d, J = 8.7 Hz, 2H), 6.57 (d, J = 8.7 Hz, 2H), 4.74-4.65 (m, 1H), 4.57-4.42 (m, 1H), 4.39 (s, 1H), 2.96-2.79 (m, 1H), 2.72-2.56 (m, 1H), 2.52-2.38 (m, 2H), 1.97-1.88 (m, 2H), 1.80-1.71 (m, 4H), 1.58-1.42 (m, 8H), 1.34-1.24 (m, 4H); ESI-MS: m/z = 352 [M + H]$^+$. |
| Compound 35 | 4-((1-(4-(cyclohexyl)piperidine-1-carbonyl)cyclopentyl)amino)benzonitrile | $^1$HNMR (500 MHz, CDCl$_3$): δ7.39 (d, J = 8.8 Hz, 2H), 6.56 (d, J = 8.8 Hz, 2H), 4.72-4.64 (m, 1H), 4.53-4.42 (m, 1H), 4.39 (s, 1H), 2.92-2.78 (m, 1H), 2.73-2.56 (m, 1H), 2.52-2.38 (m, 2H), 1.97-1.88 (m, 2H), 1.80-1.36 (m, 18H), 1.31-1.25 (m, 2H); ESI-MS: m/z = 380 [M + H]$^+$. |
| Compound 36 | 4-((1-(4-(tert-butyl)piperidine-1-carbonyl)cyclopentyl)amino)phenylacetylene | $^1$HNMR (500 MHz, CDCl$_3$): δ7.40 (d, J = 8.8 Hz, 2H), 6.59 (d, J = 8.8 Hz, 2H), 4.77-4.63 (m, 1H), 4.52-4.41 (m, 1H), 4.39 (s, 1H), 2.96-2.87 (m, 2H), 2.78-2.59 (m, 1H), 2.53-2.28 (m, 2H), 1.97-1.85 (m, 2H), 1.84-1.69 (m, 4H), 1.55-1.40 (m, 2H), 1.19-1.07 (m, 1H), 1.03-0.85 (m, 2H), 0.70 (s, 9H); ESI-MS: m/z = 353 [M + H]$^+$. |

TABLE 2.3-continued

NMR and mass spectrometry data of Compounds 32~46

| Compound No. of preparation examples | Name of Compound | | NMR and mass spectrometry data |
|---|---|---|---|
| Compound 37 | 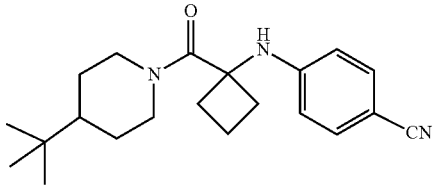 [SMILES: CC(C)(C)C1CCN(C(=O)C2(Nc3ccc(C#N)cc3)CCC2)CC1] 4-((1-(4-(tert-butyl)piperidine-1-carbonyl)cyclobutyl)amino)benzonitrile | | $^1$HNMR (500 MHz, CDCl$_3$): δ7.27 (d, J = 8.8 Hz, 2H), 6.79 (d, J = 8.8 Hz, 2H), 4.78-4.63 (m, 1H), 4.53-4.41 (m, 1H), 4.39 (s, 1H), 2.97-2.89 (m, 2H), 2.75-2.59 (m, 1H), 2.20-1.97 (m, 4H), 1.71-1.65 (m, 2H), 1.55-1.40 (m, 2H), 1.17-1.09 (m, 1H), 1.02-0.89 (m, 2H), 0.72 (s, 9H); ESI-MS: m/z = 340 [M + H]$^+$. |
| Compound 38 | 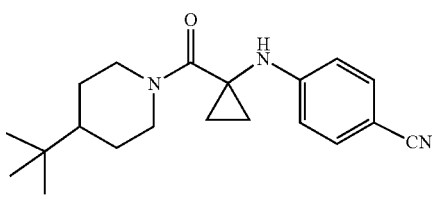 [SMILES: CC(C)(C)C1CCN(C(=O)C2(Nc3ccc(C#N)cc3)CC2)CC1] 4-((1-(4-(tert-butyl)piperidine-1-carbonyl)cyclopropyl)amino)benzonitrile | | $^1$HNMR (500 MHz, CDCl$_3$): δ7.41 (d, J = 8.8 Hz, 2H), 6.68 (d, J = 8.9 Hz, 2H), 4.75-4.60 (m, 1H), 4.52-4.43 (m, 1H), 4.39 (s, 1H), 2.94-2.78 (m, 1H), 2.72-2.56 (m, 1H), 1.54-1.43 (m, 2H), 1.19-1.07 (m, 1H), 1.04-0.78 (m, 6H), 0.69 (s, 9H); ESI-MS: m/z = 326 [M + H]$^+$. |
| Compound 39 | 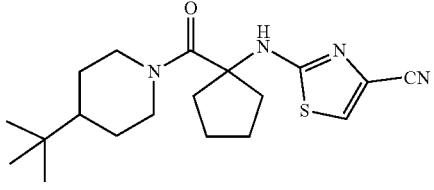 [SMILES: CC(C)(C)C1CCN(C(=O)C2(Nc3nc(C#N)cs3)CCCC2)CC1] 2-((1-(4-(tert-butyl)piperidine-1-carbonyl)cyclopentyl)amino)thiazole-4-carbonitrile | | $^1$HNMR (500 MHz, CDCl$_3$): δ7.25 (s, 1H), 4.79-4.63 (m, 1H), 4.56-4.44 (m, 1H), 4.40 (s, 1H), 2.97-2.79 (m, 1H), 2.78-2.57 (m, 1H), 2.52-2.28 (m, 2H), 1.97-1.87 (m, 2H), 1.85-1.69 (m, 4H), 1.56-1.41 (m, 2H), 1.21-1.07 (m, 1H), 1.03-0.78 (m, 2H), 0.71 (s, 9H); ESI-MS: m/z = 361 [M + H]$^+$. |
| Compound 40 | 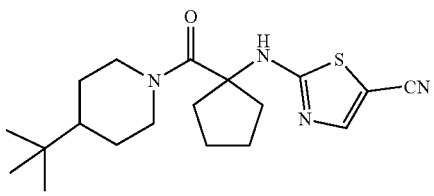 [SMILES: CC(C)(C)C1CCN(C(=O)C2(Nc3ncc(C#N)s3)CCCC2)CC1] 2-((1-(4-(tert-butyl)piperidine-1-carbonyl)cyclopentyl)amino)thiazole-5-carbonitrile | | $^1$HNMR (500 MHz, CDCl$_3$): δ8.10 (s, 1H), 4.78-4.63 (m, 1H), 4.57-4.45 (m, 1H), 4.39 (s, 1H), 2.96-2.81 (m, 1H), 2.78-2.59 (m, 1H), 2.53-2.38 (m, 2H), 1.96-1.85 (m, 2H), 1.84-1.67 (m, 4H), 1.57-1.43 (m, 2H), 1.21-1.08 (m, 1H), 1.04-0.81 (m, 2H), 0.70 (s, 9H); ESI-MS: m/z = 361 [M + H]$^+$. |
| Compound 41 | 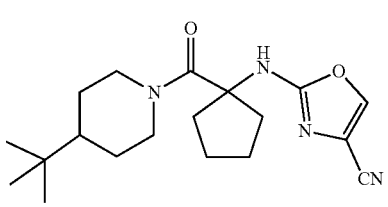 [SMILES: CC(C)(C)C1CCN(C(=O)C2(Nc3nc(C#N)co3)CCCC2)CC1] 2-((1-(4-(tert-butyl)piperidine-1-carbonyl)cyclopentyl)amino)oxazole-4-carbonitrile | | $^1$HNMR (500 MHz, CDCl$_3$): δ7.69(s, 1H), 4.76-4.64 (m, 1H), 4.57-4.47 (m, 1H), 4.39 (s, 1H), 2.96-2.81 (m, 1H), 2.78-2.67 (m, 1H), 2.51-2.28 (m, 2H), 1.97-1.85 (m, 2H), 1.84-1.71(m, 4H), 1.56-1.42 (m, 2H), 1.23-1.08 (m, 1H), 1.02-0.79 (m, 2H), 0.70 (s, 9H); ESI-MS: m/z = 345 [M + H]$^+$. |

TABLE 2.3-continued

NMR and mass spectrometry data of Compounds 32~46

| Compound No. of preparation examples | Name of Compound | NMR and mass spectrometry data |
|---|---|---|
| Compound 42 | 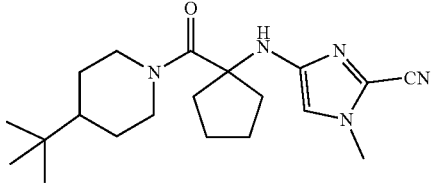 [SMILES: Cn1cc(NC2(C(=O)N3CCC(C(C)(C)C)CC3)CCCC2)nc1C#N]<br>4-((1-(4-(tert-butyl)piperidine-1-carbonyl)cyclopentyl)amino)-1-methyl-1H-imidazole-2-carbonitrile | $^1$HNMR (500 MHz, CDCl$_3$): δ7.44(s, 1H), 4.75-4.64 (m, 1H), 4.58-4.49 (m, 1H), 4.39 (s, 1H), 3.72 (s, 3H), 2.95-2.81 (m, 1H), 2.76-2.68 (m, 1H), 2.50-2.25 (m, 2H), 1.96-1.86 (m, 2H), 1.84-1.70 (m, 4H), 1.57-1.43 (m, 2H), 1.24-1.09 (m, 1H), 1.03-0.78 (m, 2H), 0.70 (s, 9H);<br>ESI-MS: m/z = 358 [M + H]$^+$. |
| Compound 43 | 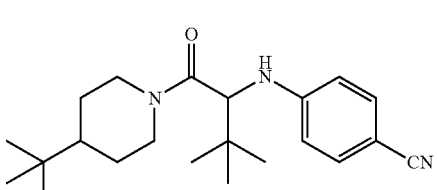<br>4-((1-(4-(tert-butyl)piperidine-1-carbonyl)tert-butyl)amino)benzonitrile | $^1$HNMR (500 MHz, CDCl$_3$): δ7.43 (d, J = 8.6 Hz, 2H), 6.71 (d, J = 8.6 Hz, 2H), 4.75-4.64 (m, 1H), 4.58-4.49 (m, 1H), 4.39 (s, 1H), 2.95-2.81 (m, 1H), 2.76-2.68 (m, 1H), 1.57-1.43 (m, 2H), 1.24-1.09 (m, 1H), 1.03-0.78 (m, 2H), 0.84 (s, 9H), 0.70 (s, 9H);<br>ESI-MS: m/z = 356 [M + H]$^+$. |
| Compound 44 | 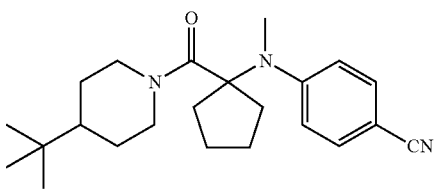 [SMILES: CN(c1ccc(C#N)cc1)C1(C(=O)N2CCC(C(C)(C)C)CC2)CCCC1]<br>4-((1-(4-(tert-butyl)piperidine-1-carbonyl)cyclopentyl)methylamino)benzonitrile | $^1$HNMR (500 MHz, CDCl$_3$): δ7.39 (d, J = 8.8 Hz, 2H), 6.61 (d, J = 8.8 Hz, 2H), 4.77-4.62 (m, 1H), 4.53-4.41 (m, 1H), 3.05 (s, 3H), 2.94-2.77 (m, 1H), 2.75-2.55 (m, 1H), 2.52-2.29 (m, 2H), 1.97-1.87 (m, 2H), 1.83-1.64 (m, 4H), 1.52-1.41 (m, 2H), 1.19-1.07 (m, 1H), 1.03-0.76 (m, 2H), 0.72 (s, 9H);<br>ESI-MS: m/z = 368 [M + H]$^+$. |
| Compound 45 | 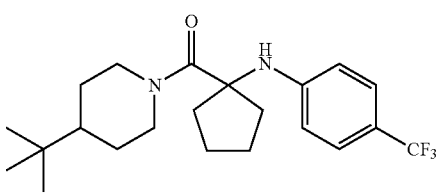 [SMILES: CC(C)(C)C1CCN(C(=O)C2(Nc3ccc(C(F)(F)F)cc3)CCCC2)CC1]<br>4-((1-(4-(tert-butyl)piperidine-1-carbonyl)cyclopentyl)methylamino)trifluoromethylbenzene | $^1$HNMR (500 MHz, CDCl$_3$): δ7.37 (d, J = 8.6 Hz, 2H), 6.46 (d, J = 8.6 Hz, 2H), 4.72-4.63 (m, 1H), 4.56-4.42 (m, 1H), 4.39 (s, 1H), 2.94-2.77 (m, 1H), 2.73-2.55 (m, 1H), 2.51-2.38 (m, 2H), 1.94-1.87 (m, 2H), 1.82-1.66 (m, 4H), 1.54-1.43(m, 2H), 1.17-1.07 (m, 1H), 1.03-0.78 (m, 2H), 0.69 (s, 9H);<br>ESI-MS: m/z = 397 [M + H]$^+$. |
| Compound 46 | 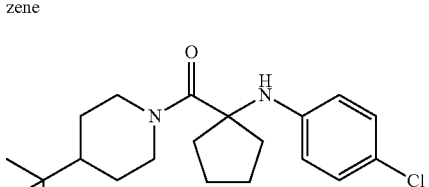<br>4-((1-(4-(tert-butyl)piperidine-1-carbonyl)cyclopentyl)amino)chlorobenzene | $^1$HNMR (500 MHz, CDCl$_3$): δ7.05 (d, J = 8.7 Hz, 2H), 6.59 (d, J = 8.7 Hz, 2H), 4.77-4.65 (m, 1H), 4.52-4.41 (m, 1H), 4.39 (s, 1H), 2.96-2.78 (m, 1H), 2.72-2.58 (m, 1H), 2.52-2.38 (m, 2H), 1.95-1.87 (m, 2H), 1.83-1.79 (m, 4H), 1.56-1.45 (m, 2H), 1.19-1.07 (m, 1H), 1.02-0.78 (m, 2H), 0.71 (s, 9H);<br>ESI-MS: m/z = 363 [M + H]$^+$. |

Preparation Example 11. Synthesis of 4-((1-(4-(6-(trifluoromethyl)pyridin-2-yl) piperazine-1-carbonyl)cyclopentyl)oxy)benzonitrile (Compound 47)

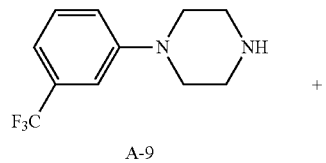

A-9

+

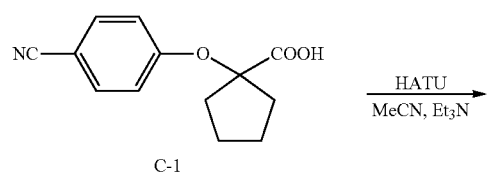

C-1

HATU
MeCN, Et₃N

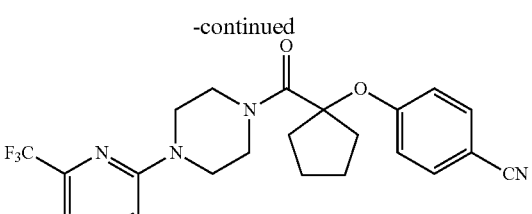

47

Synthetic steps: A-9 (0.33 g, 1.40 mmol), C-1 (0.30 g, 1.30 mmol), and anhydrous triethylamine (0.263 g, 2.60 mmol) were dissolved in 25 mL anhydrous acetonitrile, and then HATU (0.513 g, 1.40 mmol) was added to react under room temperature for 30 min. After completion of the reaction, the resultant was diluted by addition of water, extracted with ethyl acetate, and washed with dilute hydrochloric acid, sodium bicarbonate solution, and saturated saline solution. The organic layer was dried over anhydrous sodium sulfate, filtered, and concentrated, and purified via silica gel column chromatography (PE:EA=2:1, v/v) to obtain Compound 47 (0.385 g) with a yield of 66.6%. $^1$H NMR (500 MHz, CDCl₃) δ 7.59 (t, J=8.0 Hz, 1H), 7.54 (d, J=9.0 Hz, 2H), 6.97 (d, J=7.3 Hz, 1H), 6.94 (d, J=9.0 Hz, 2H), 6.71 (d, J=8.7 Hz, 1H), 3.83 (t, J=5.2 Hz, 2H), 3.71 (t, J=5.0 Hz, 2H), 3.44 (t, J=5.0 Hz, 2H), 3.38 (t, J=5.0 Hz, 2H), 2.61-2.48 (m, 2H), 2.23-2.11 (m, 2H), 1.88-1.72 (m, 4H); ESI-MS: m/z=445 [M+H]⁺.

Compounds 48-67 in Table 2.4 were synthesized using the corresponding 4-substituted piperidine or 4-substituted piperazine and the intermediate C as raw materials according to the same method as for preparation of Compound 47.

TABLE 2.4

NMR and mass spectrometry data of Compounds 48~67

| Compound No. of preparation examples | Name of Compound | NMR and mass spectrometry data |
|---|---|---|
| Compound 48 | 4-((1-(4-(m-methylphenyl)piperazine-1-carbonyl)cyclopentyl)oxy)benzonitrile | $^1$HNMR (500 MHz, CDCl₃): δ7.56 (d, J = 8.1 Hz, 2H), 7.08 (d, J = 8.0 Hz, 1H), 6.92 (d, J = 8.1 Hz, 2H), 6.90 (m, J = 8.0 Hz, 1H), 6.70 (s, 1H), 6.35 (d, J = 8.0Hz, 1H),3.91-3.89 (m, 2H), 3.76-3.74 (m, 2H), 3.11-3.09 (m, 2H), 2.95-2.92 (m, 2H), 2.58-2.53 (m, 2H), 2.19-2.12 (m, 2H), 1.83-1.79 (m, 4H); ESI-MS: m/z = 390 [M + H]⁺ |
| Compound 49 | 4-((1-(4-(trifluoromethyl)phenyl)piperazine-1-carbonyl)cyclopentyl)oxy)benzonitrile | $^1$HNMR (500 MHz, CDCl₃): δ7.56 (d, J = 8.1 Hz, 2H), 7.47 (d, J = 8.0 Hz, 2H),6.93 (d, J = 8.1 Hz, 2H), 6.83 (d, J = 8.0H z, 2H), 3.89-3.87 (m, 2H), 3.77-3.74 (m, 2H), 3.15-3.13 (m, 2H), 2.99-2.97 (m, 2H), 2.57-2.54 (m, 2H), 2.18-2.14 (m, 2H), 1.85-1.77 (m, 4H); ESI-MS: m/z = 444 [M + H]⁺ |

TABLE 2.4-continued

NMR and mass spectrometry data of Compounds 48~67

| Compound No. of preparation examples | Name of Compound | NMR and mass spectrometry data |
|---|---|---|
| Compound 50 | 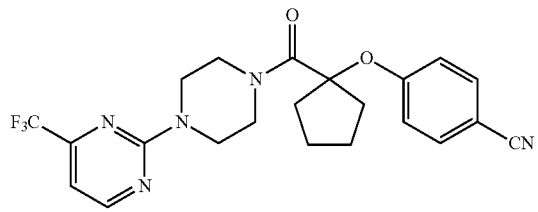 [SMILES: N#Cc1ccc(OC2(C(=O)N3CCN(c4nccc(C(F)(F)F)n4)CC3)CCCC2)cc1]<br>4-((1-(4-(4-(trifluoromethyl)pyrimidin-2-yl)piperazine-1-carbonyl)cyclopentyl)oxy)benzonitrile | $^1$HNMR (500 MHz, CDCl$_3$): δ8.30 (d, J = 8.0 Hz, 1H), 7.54 (d, J = 9.0 Hz, 2H), 7.03 (d, J = 8.0 Hz, 1H), 6.94 (d, J = 9.0 Hz, 2H), 3.84 (t, J = 5.2 Hz, 2H), 3.70 (t, J = 5.0 Hz, 2H), 3.42 (t, J = 5.0 Hz, 2H), 3.39 (t, J = 5.0 Hz, 2H), 2.61-2.49 (m, 2H), 2.23-2.13 (m, 2H), 1.88-1.71 (m, 4H);<br>ESI-MS: m/z = 446 [M + H]$^+$ |
| Compound 51 | 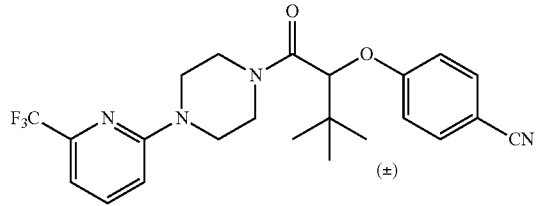 [SMILES: CC(C)(C)C(Oc1ccc(C#N)cc1)C(=O)N1CCN(c2cccc(C(F)(F)F)n2)CC1]<br>4-((1-(4-(4-(trifluoromethyl)pyrimidin-2-yl)piperazine-1-carbonyl)tert-butyl)oxy)benzonitrile | $^1$HNMR (500 MHz, CDCl$_3$): δ7.58 (m, 1H), 7.54 (d, J = 9.0 Hz, 2H), 6.95 (d, J = 9.0 Hz, 2H), 6.92 (d, J = 7.3 Hz, 1H), 6.73 (d, J = 8.7 Hz, 1H), 4.35 (s, 1H), 3.84 (t, J = 5.2 Hz, 2H), 3.73 (t, J = 5.0 Hz, 2H), 3.45 (t, J = 5.0 Hz, 2H), 3.39 (t, J = 5.0 Hz, 2H), 0.89 (s, 9H);<br>ESI-MS: m/z = 447 [M + H]$^+$ |
| Compound 52 | 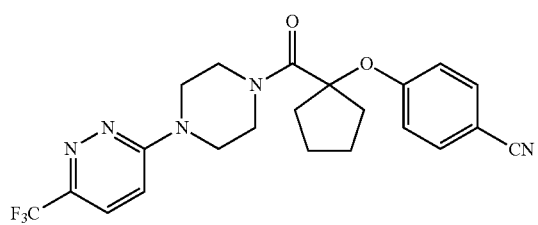 [SMILES: N#Cc1ccc(OC2(C(=O)N3CCN(c4ccc(C(F)(F)F)nn4)CC3)CCCC2)cc1]<br>4-((1-(4-(6-(trifluoromethyl)pyridazin-3-yl)piperazine-1-carbonyl)cyclopentyl)oxy)benzonitrile | $^1$HNMR (500 MHz, CDCl$_3$): δ7.54 (d, J = 9.0 Hz, 2H), 7.14 (d, J = 8.0 Hz, 1H), 6.94 (d, J = 9.0 Hz, 2H), 6.82 (d, J = 8.0 Hz, 1H), 3.85 (t, J = 5.1 Hz, 2H), 3.72 (t, J = 5.0 Hz, 2H), 3.43 (t, J = 5.0 Hz, 2H), 3.38 (t, J = 5.0 Hz, 2H), 2.61-2.51 (m, 2H), 2.23-2.11 (m, 2H), 1.86-1.70 (m, 4H);<br>ESI-MS: m/z = 446 [M + H]$^+$ |
| Compound 53 | 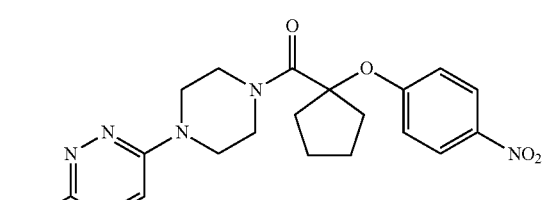<br>4-((1-(4-(6-(trifluoromethyl)pyridazin-3-yl)piperazine-1-carbonyl)cyclopentyl)oxy)nitrobenzene | $^1$HNMR (500 MHz, CDCl$_3$): δ7.54 (d, J = 9.0 Hz, 2H), 7.14 (d, J = 8.0 Hz, 1H), 6.94 (d, J = 9.0 Hz, 2H), 6.82 (d, J = 8.0 Hz, 1H), 3.86 (t, J = 5.0 Hz, 2H), 3.72 (t, J = 5.0 Hz, 2H), 3.44 (t, J = 5.0 Hz, 2H), 3.39 (t, J = 5.0 Hz, 2H), 2.60-2.53 (m, 2H), 2.23-2.12 (m, 2H), 1.86-1.71 (m, 4H);<br>ESI-MS: m/z = 466 [M + H]$^+$ |

TABLE 2.4-continued

NMR and mass spectrometry data of Compounds 48~67

| Compound No. of preparation examples | Name of Compound | NMR and mass spectrometry data |
|---|---|---|
| Compound 54 | 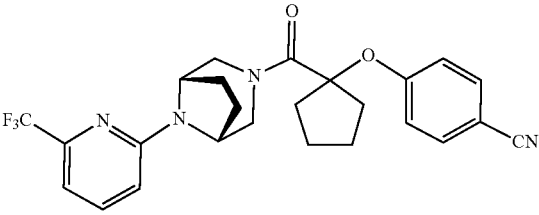<br>4-((1-(8-(6-(trifluoromethyl) pyridin-2-yl)-3,8-diazabicyclo [3.2.1]octane-3-carbonyl)cy clopentyl)amino)benzonitrile | $^1$HNMR (500 MHz, CDCl$_3$): δ7.60-7.54 (m, 3H), 6.97-6.93 (m, 3H), 6.70 (d, J = 8.8 Hz, 1H), 4.57 (m, 1H), 4.49 (m, 1H), 4.22 (m, 2H), 3.31-3.28 (d, 1H), 3.01-2.98 (d, 1H), 2.71-2.68 (d, 1H), 2.27-2.06 (m, 3H), 1.91-1.58 (m, 6H), 1.48-1.42 (m, 1H), 1.05 (m, 1H);<br>ESI-MS: m/z = 471 [M + H]$^+$ |
| Compound 55 | 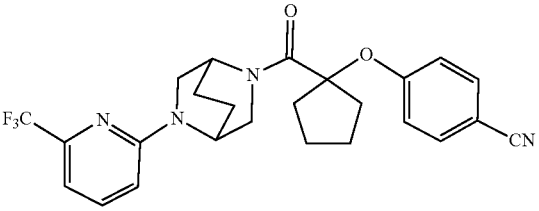 [SMILES: N#Cc1ccc(OC2(C(=O)N3CC4CCC3CN4c3cccc(C(F)(F)F)n3)CCCC2)cc1]<br>4-((1-(5-(6-(trifluoromethyl)p yridin-2-yl)-2,5-diazabicyclo [2.2.2]octane-2-carbonyl)cycl opentyl)oxy)benzonitrile | $^1$HNMR (500 MHz, CDCl$_3$): δ7.62-7.58 (m, 3H), 6.98-6.93 (m, 3H), 6.71 (d, J = 8.6 Hz, 1H), 4.63-4.59 (m, 1H), 4.52-4.49 (m, 1H), 4.26-4.17 (m, 2H), 3.33-3.02 (m, 2H), 2.76-2.54 (m, 2H), 2.24-2.06 (m, 2H), 1.93-1.65 (m, 6H), 1.46-1.39 (m, 1H), 1.12-0.98 (m, 1H);<br>ESI-MS: m/z = 471 [M + H]$^+$ |
| Compound 56 | 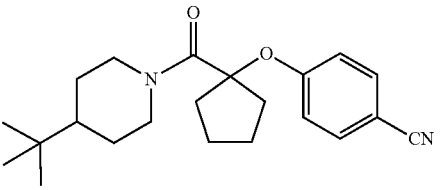 [SMILES: CC(C)(C)C1CCN(C(=O)C2(Oc3ccc(C#N)cc3)CCCC2)CC1]<br>4-((1-(4-(tert-butyl)piperidine-1-carbonyl)cyclopentyl)oxy) benzonitrile | $^1$HNMR (500 MHz, CDCl$_3$): δ7.54 (d, J = 8.8 Hz, 2H), 6.93 (d, J = 8.8 Hz, 2H), 4.68-4.63 (m, 1H), 4.51-4.47 (m, 1H), 2.79-2.73 (m, 1H), 2.65-2.62 (m, 1H), 2.48-2.43 (m, 2H), 2.19-2.15 (m, 1H), 2.10-2.08 (m, 1H), 1.82-1.67 (m, 4H), 1.65-1.60 (m, 2H), 1.54-1.51 (m, 1H), 1.14-1.07 (m, 1H), 0.94-0.89 (m, 1H), 0.66 (s, 9H);<br>ESI-MS: m/z = 355 [M + H]$^+$ |
| Compound 57 | 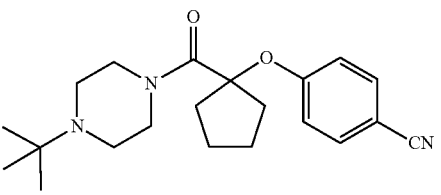<br>4-((1-(4-(tert-butyl)piperazine-1-carbonyl)cyclopentyl)oxy) benzonitrile | $^1$HNMR (500 MHz, CDCl$_3$): δ7.56 (d, J = 8.8 Hz, 2H), 6.92 (d, J = 8.9 Hz, 2H), 3.77 (m, 4H), 3.47 (m, 4H), 2.49-2.13 (m, 4H), 1.83-1.65 (m, 4H), 1.20 (s, 9H);<br>ESI-MS: m/z = 356 [M + H]$^+$ |

TABLE 2.4-continued

NMR and mass spectrometry data of Compounds 48~67

| Compound No. of preparation examples | Name of Compound | | NMR and mass spectrometry data |
|---|---|---|---|
| Compound 58 | 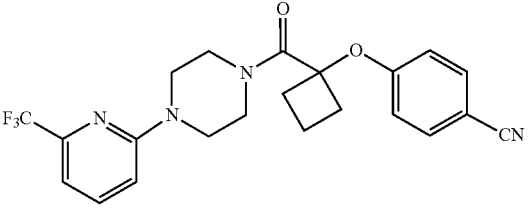 [SMILES: N#Cc1ccc(OC2(C(=O)N3CCN(c4cccc(C(F)(F)F)n4)CC3)CCC2)cc1]<br>4-((1-(4-(6-(trifluoromethyl)pyridin-2-yl)piperazine-1-carbonyl)cyclobutyl)oxy)benzonitrile | | $^1$HNMR (500 MHz, CDCl$_3$): δ7.58 (m, J = 8.0 Hz, 1H), 7.55 (d, J = 9.0 Hz, 2H), 6.96 (d, J = 7.3 Hz, 1H), 6.92 (d, J = 9.0 Hz, 2H), 6.70 (d, J = 8.7 Hz, 1H), 3.84 (m,2H), 3.71 (m, 2H), 3.42 (t, J = 5.0 Hz, 2H), 3.39 (t, J = 5.0 Hz,2H), 2.54 (m, 2H), 2.29 (m, 2H), 1.88-1.72 (m, 2H);<br>ESI-MS: m/z = 431 [M + H]$^+$ |
| Compound 59 | 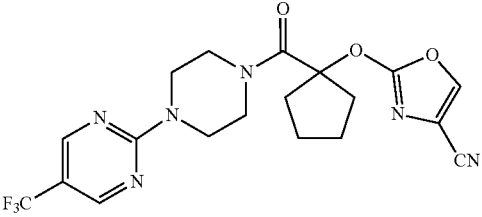 [SMILES: N#Cc1coc(OC2(C(=O)N3CCN(c4ncc(C(F)(F)F)cn4)CC3)CCCC2)n1]<br>4-((1-(4-(4-(trifluoromethyl)pyrimidin-2-yl)piperazine-1-carbonyl)cyclopentyl)oxy)oxazole-4-carbonitrile | | $^1$HNMR (500 MHz, CDCl$_3$): δ8.58 (d, J = 8.0 Hz, 2H), 7.60 (s, 1H), 3.85 (t, J = 5.2 Hz, 2H), 3.71 (t, J = 5.0 Hz, 2H), 3.45 (t, J = 5.0 Hz, 2H), 3.42 (t, J = 5.0 Hz, 2H), 2.60-2.47 (m, 2H), 2.25-2.12 (m, 2H), 1.89-1.70 (m, 4H);<br>ESI-MS: m/z = 437 [M + H]$^+$ |
| Compound 60 | 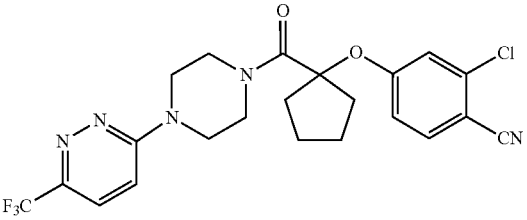 [SMILES: N#Cc1ccc(OC2(C(=O)N3CCN(c4ccc(C(F)(F)F)nn4)CC3)CCCC2)cc1Cl]<br>2-chloro-4-((1-(4-(6-(trifluoromethyl)pyridazin-3-yl)piperazine-1-carbonyl)cyclopentyl)oxy)benzonitrile | | $^1$HNMR (500 MHz, CDCl$_3$): δ7.54 (d, J = 8.7 Hz, 1H), 7.48 (s, 1H), 7.02 (m, 2H) ,6.72 (d, J = 8.8 Hz, 1H), 3.97 (m, 4H), 3.68 (m, 4H), 2.63-2.56 (m, 2H), 1.93-1.88 (m, 2H), 1.83-1.75 (m, 4H);<br>ESI-MS: m/z = 480 [M + H]$^+$ |
| Compound 61 | 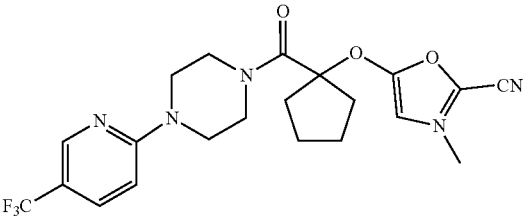<br>1-methyl-4-((1-(4-(5-(trifluoromethyl)pyridin-2-yl)piperazine-1-carbonyl)cyclopentyl)oxy)-1H-imidazole-2-carbonitrile | | $^1$HNMR (500 MHz, CDCl$_3$): δ8.50 (s, 1H), 8.02 (d, J = 8.0 Hz, 1H), 7.48 (s, 1H), 6.53 (d, J = 8.0 Hz, 1H), 3.92-3.87 (m, 2H), 3.78-3.74 (m, 2H), 3.72 (s, 3H),3.16-3.12 (m, 2H), 2.99-2.93 (m, 2H), 2.58-2.52 (m, 2H), 2.18-2.13 (m, 2H), 1.87-1.79 (m, 4H);<br>ESI-MS: m/z = 449 [M + H]$^+$ |

TABLE 2.4-continued

NMR and mass spectrometry data of Compounds 48~67

| Compound No. of preparation examples | Name of Compound | NMR and mass spectrometry data |
|---|---|---|
| Compound 62 | 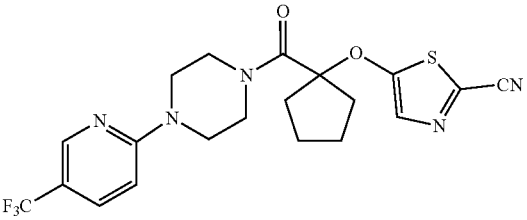 [SMILES: N#Cc1ncc(OC2(C(=O)N3CCN(c4ccc(C(F)(F)F)cn4)CC3)CCCC2)s1]<br>2-((1-(4-(5-(trifluoromethyl)pyridin-2-yl)piperazine-1-carbonyl)cyclopentyl)oxy)thiazole-5-carbonitrile | $^1$HNMR (500 MHz, CDCl$_3$): δ8.52 (s, 1H), 8.03 (m, 2H), 6.63 (d, J = 8.0 Hz, 1H), 3.93-3.84 (m, 2H), 3.79-3.73 (m, 2H), 3.17-3.12 (m, 2H), 2.98-2.92 (m, 2H), 2.59-2.51 (m, 2H), 2.19-2.12 (m, 2H), 1.88-1.78 (m, 4H);<br>ESI-MS: m/z = 452 [M + H]$^+$ |
| Compound 63 | 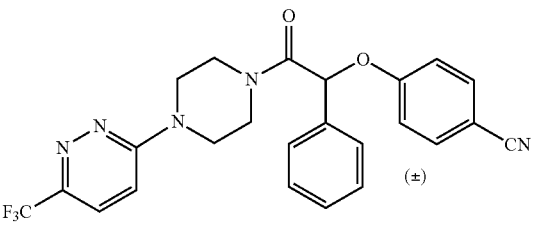 [SMILES: N#Cc1ccc(OC(C(=O)N2CCN(c3ccc(C(F)(F)F)nn3)CC2)c2ccccc2)cc1]<br>4-(1-phenyl-2-(4-6-(trifluoromethyl)pyridazin-3-yl)piperazine-1-yl)ethoxy)benzonitrile | $^1$HNMR (500 MHz, CDCl$_3$): δ7.55 (d, J = 8.7 Hz, 2H), 7.33 (m, 2H), 7.28 (m, 3H), 7.02 (d, J = 8.0 Hz, 1H), 6.92 (d, J = 8.7 Hz, 2H), 6.71 (d, J = 8.0 Hz, 1H), 5.90 (s, 1H), 3.86 (m, 4H), 3.55 (m, 4H);<br>ESI-MS: m/z = 468 [M + H]$^+$ |
| Compound 64 | 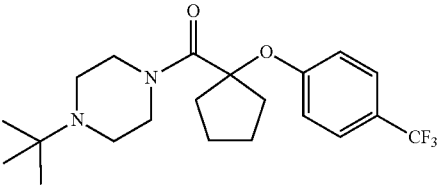 [SMILES: CC(C)(C)N1CCN(C(=O)C2(Oc3ccc(C(F)(F)F)cc3)CCCC2)CC1]<br>4-((1-(4-(tert-butyl)piperazine-1-carbonyl)cyclopentyl)oxy)trifluoromethylbenzene | $^1$HNMR (500 MHz, CDCl$_3$): δ7.42 (d, J = 8.9 Hz, 2H), 6.70 (d, J = 8.9 Hz, 2H), 3.78 (m, 4H), 3.46 (m, 4H); 2.65-2.53 (m, 2H), 2.49-2.13 (m, 2H), 1.83-1.65 (m, 4H), 1.20 (s, 9H);<br>ESI-MS: m/z = 399 [M + H]$^+$ |
| Compound 65 | 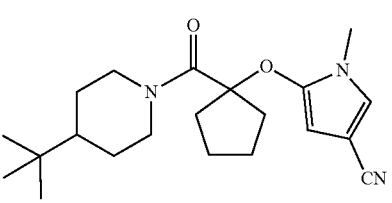 [SMILES: Cn1cc(C#N)cc1OC1(C(=O)N2CCC(C(C)(C)C)CC2)CCCC1]<br>5-((1-(4-(tert-butyl)piperidine-1-carbonyl)cyclopentyl)oxy)-1-methyl-1H-pyrrole-3-carbonitrile | $^1$HNMR (500 MHz, CDCl$_3$): δ7.45(s, 1H), 6.19 (s, 1H), 4.72-4.64 (m, 1H), 4.56-4.49 (m, 1H), 3.59 (s, 3H), 2.96-2.80 (m, 1H), 2.77-2.68 (m, 1H), 2.50-2.22 (m, 2H), 1.93-1.86 (m, 2H), 1.82-1.71 (m, 4H), 1.57-1.41 (m, 2H), 1.21-1.09 (m, 1H), 1.03-0.79 (m, 2H), 0.69 (s, 9H);<br>ESI-MS: m/z = 358 [M + H]+. |
| Compound 66 | 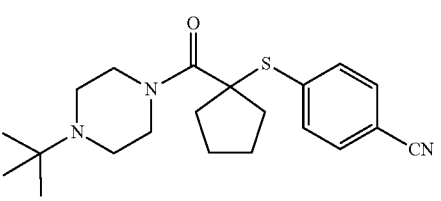<br>4-((1-(4-(tert-butyl)piperazine-1-carbonyl)cyclopentyl)sulfanyl)benzonitrile | $^1$HNMR (500 MHz, CDCl$_3$): δ7.50 (m, 4H), 3.75 (m, 4H), 3.49 (m, 4H), 2.48-2.14 (m, 4H), 1.82-1.66 (m, 4H), 1.21 (s, 9H);<br>ESI-MS: m/z = 372 [M + H]$^+$ |

TABLE 2.4-continued

NMR and mass spectrometry data of Compounds 48~67

| Compound No. of preparation examples | Name of Compound | NMR and mass spectrometry data |
|---|---|---|
| Compound 67 | 5-((1-(4-(tert-butyl)piperidine-1-carbonyl)cyclopentyl)sulfanyl)-1-methyl-1H-indole | $^1$HNMR (500 MHz, CDCl$_3$): δ7.60 (d, J = 8.6 Hz, 1H), 7.11 (m, 2H), 7.02 (d, J = 8.6 Hz, 1H), 6.42 (d, J = 8.6 Hz, 1H),4.72-4.64 (m, 1H), 4.56-4.49 (m, 1H), 3.74 (s, 3H), 2.97-2.81 (m, 1H), 2.77-2.67 (m, 1H), 2.51-2.21 (m, 2H), 1.93-1.85 (m, 2H), 1.83-1.70 (m, 4H), 1.58-1.40 (m, 2H), 1.20-1.08 (m, 1H), 1.02-0.78 (m, 2H), 0.70 (s, 9H); ESI-MS: m/z = 399 [M + H]$^+$. |

Preparation Example 12. Synthesis of 2-(4-(6-(trifluoromethyl)pyridin-2-yl)piperazine-1-carbonyl)-5-cyanoindoline (Compound 68)

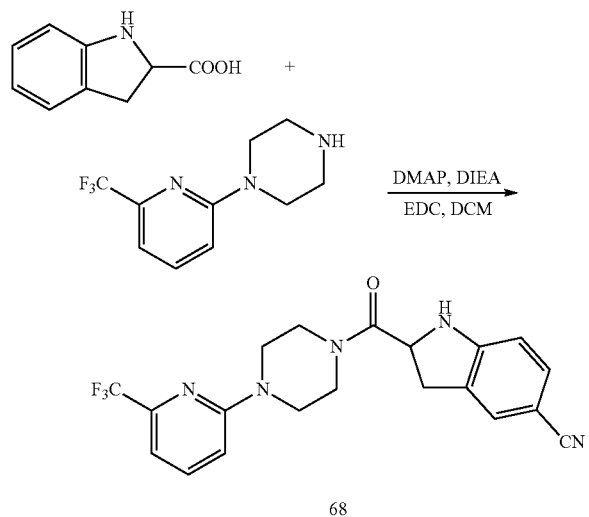

Synthetic steps: 5-cyanoindoline-2-carboxylic acid (0.282 g, 1.5 mmol) was dissolved in 10 mL DCM, and added respectively with DMAP (0.35 g, 2.86 mmol), DIEA (0.4 mL, 2.3 mmol), A-9 (0.51 g, 1.95 mmol) and EDC (0.37 g, 1.93 mmol). The resultant was stirred under room temperature for about 20 hr. The reaction mixture was washed sequentially with 1N citric acid aqueous solution (10 mL), water (10 mL), 1N NaOH aqueous solution (10 mL) and saturated saline solution (10 mL). The organic layer was dried over anhydrous Na$_2$SO$_4$, filtered, and concentrated, and the residue was separated via silica gel column chromatography (EA:PE=1:3, v/v) to obtain Compound 68 with a yield of 62%. $^1$HNMR (500 MHz, CDCl$_3$): δ7.61 (s, 1H), 7.57 (t, 1H), 7.30 (d, J=8.0 Hz, 1H), 6.97 (d, J=9.0 Hz, 1H), 6.79 (d, J=8.0 Hz, 1H), 6.70 (d, J=9.0 Hz, 1H), 4.20 (s, 1H), 3.95 (m, 1H), 3.78 (m, 2H), 3.52 (m, 2H), 3.18 (m, 4H), 3.13 (m, 1H), 2.89 (m, 1H); ESI-MS: m/z=402 [M+H]$^+$.

Compounds 69-80 in Table 2.5 were synthesized using the corresponding 4-substituted piperidine or 4-substituted piperazine and indoline-2-carboxylic acid/indole-2-carboxylic acid benzofuran-2-carboxylic acid 2,3-dihydrobenzofuran-2-carboxylic acid as raw materials according to the same method as for preparation of Compound 68.

TABLE 2.5

NMR and mass spectrometry data of Compounds 69~80

| Compound No. of preparation examples | Name of Compound | NMR and mass spectrometry data |
|---|---|---|
| Compound 69 | 2-(4-(4-(trifluoromethyl)pyrimidin-2-yl)piperazine-1-carbonyl)-5-cyanoindoline | $^1$HNMR (500 MHz,CDCl$_3$): δ8.31 (d, J = 8.7 Hz, 1H), 7.61 (s, 1H), 7.30 (d, J = 8.0 Hz, 1H), 7.02 (d, J = 8.7 Hz, 1H), 6.79 (d, J = 8.0 Hz, 1H), 4.22 (s, 1H), 3.96 (m, 1H), 3.77 (m, 2H), 3.53 (m, 2H), 3.17 (m, 4H), 3.14 (m, 1H), 2.87 (m, 1H); ESI-MS: m/z = 403 [M + H]$^+$ |

TABLE 2.5-continued

NMR and mass spectrometry data of Compounds 69~80

| Compound No. of preparation examples | Name of Compound | NMR and mass spectrometry data |
|---|---|---|
| Compound 70 | 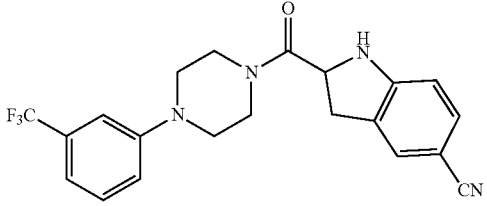 [SMILES: N#Cc1ccc2c(c1)CC(C(=O)N1CCN(c3cccc(C(F)(F)F)c3)CC1)N2]<br>2-(4-(3-(trifluoromethyl)phenyl)piperazine-1-carbonyl)-5-cyanoindoline | $^1$HNMR (500 MHz, CDCl$_3$): δ7.61 (s, 1H), 7.35 (t, 1H), 7.30 (d, J = 8.0 Hz, 1H), 7.12 (d, J = 8.8 Hz, 1H), 7.02 (d, J = 8.8 Hz, 1H), 6.98 (d, J = 8.9 Hz, 1H), 6.79 (d, J = 8.0 Hz, 1H), 4.93 (t, 1H), 4.22 (s, 1H), 3.97 (m, 1H), 3.75 (m, 2H), 3.53 (m, 2H), 3.17 (m, 4H), 3.12 (m, 1H), 2.88 (m, 1H); ESI-MS: m/z = 401 [M + H]$^+$ |
| Compound 71 | 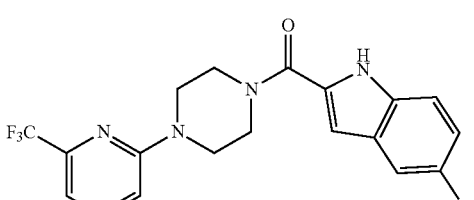<br>2-(4-(6-(trifluoromethyl)pyridin-2-yl)piperazine-1-carbonyl)-1H-5-cyanoindole | 1HNMR (500 MHz, CDCl$_3$): δ11.20 (s, 1H), 7.78 (m, 2H), 7.58 (t, 1H), 7.30 (d, J = 8.0 Hz, 1H), 7.29 (s, 1H), 6.83 (d, J = 8.8 Hz, 1H), 6.68 (d, J = 8.8 Hz, 1H), 3.79 (m, 2H), 3.53 (m, 2H), 3.19 (m, 4H); ESI-MS: m/z = 400 [M + H]$^+$ |
| Compound 72 | 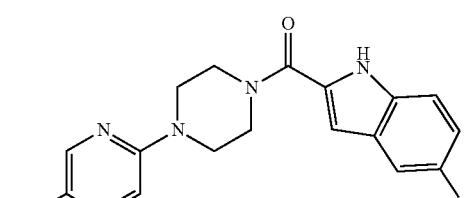<br>2-(4-(5-(trifluoromethyl)pyridin-2-yl)piperazine-1-carbonyl)-1H-5-cyanoindole | $^1$HNMR (500 MHz, CDCl$_3$): δ11.20 (s, 1H), 8.55 (s, 1H), 8.07 (d, J = 8.7 Hz, 1H), 7.78 (m, 2H), 7.31 (d, J = 8.0 Hz, 1H), 7.28 (s, 1H), 6.62 (d, J = 8.7 Hz, 1H), 3.79 (m, 2H), 3.52 (m, 2H), 3.20 (m, 4H); ESI-MS: m/z = 400 [M + H]$^+$ |
| Compound 73 | 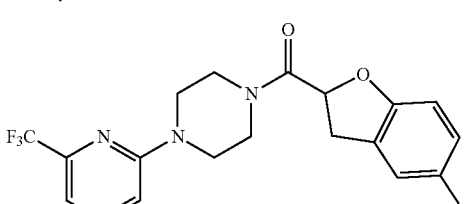<br>2-(4-(6-(trifluoromethyl)pyridin-2-yl)piperazine-1-carbonyl)-2,3-2H-5-cyanobenzofuran | $^1$HNMR (500 MHz, CDCl$_3$): δ7.79 (d, J = 8.0 Hz, 1H), 7.72 (s, 1H), 7.57 (t, 1H), 7.15 (d, J = 8.0 Hz, 1H), 6.83 (d, J = 8.8 Hz, 1H), 6.68 (d, J = 8.8 Hz, 1H), 4.94 (t, 1H), 3.78 (m, 2H), 3.52 (m, 2H), 3.21 (m, 4H), 3.33 (m, 1H), 3.09 (m, 1H); ESI-MS: m/z = 403 [M + H]$^+$ |
| Compound 74 | 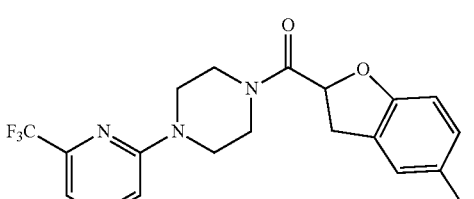<br>2-(4-(6-(trifluoromethyl)pyridin-2-yl)piperazine-1-carbonyl)-2,3-2H-5-chlorobenzofuran | $^1$HNMR (500 MHz, CDCl$_3$): δ7.55 (t, 1H), 7.28 (s, 1H), 7.19 (d, J = 8.0 Hz, 1H), 6.87 (s, d = 8.0 Hz, 1H), 6.84 (d, J = 8.8 Hz, 1H), 6.69 (d, J = 8.8 Hz, 1H), 4.92 (t, 1H), 3.77 (m, 2H), 3.53 (m, 2H), 3.20 (m, 4H), 3.30 (m, 1H), 3.09 (m, 1H); ESI-MS: m/z = 412 [M + H]$^+$ |

TABLE 2.5-continued

NMR and mass spectrometry data of Compounds 69~80

| Compound No. of preparation examples | Name of Compound | NMR and mass spectrometry data |
|---|---|---|
| Compound 75 | 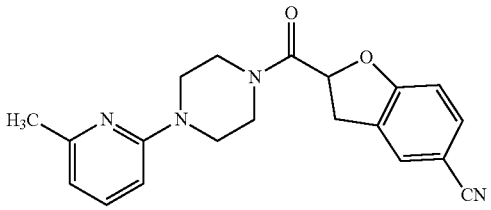 [SMILES: Cc1cccc(N2CCN(C(=O)C3Cc4cc(C#N)ccc4O3)CC2)n1]<br>2-(4-(6-methyl)pyridin-2-yl)piperazine-1-carbonyl)-2,3-2H-5-cyanobenzofuran | $^1$HNMR (500 MHz, CDCl$_3$): δ7.79 (d, J = 8.0 Hz, 1H), 7.72 (s, 1H), 7.15 (d, J = 8.0 Hz, 1H), 7.43 (t, 1H), 6.57 (d, J = 8.6 Hz, 1H), 6.41 (d, J = 8.7 Hz, 1H), 4.93 (t, 1H), 3.79 (m, 2H), 3.50 (m, 2H), 3.23 (m, 4H), 3.31 (m, 1H), 3.09 (m, 1H); 2.49 (s, 3H); ESI-MS: m/z = 349 [M + H]$^+$ |
| Compound 76 | 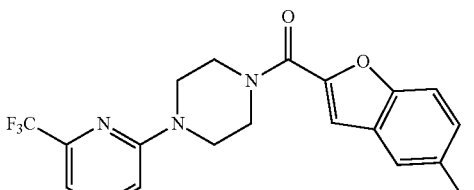<br>2-(4-(5-(trifluoromethyl)pyridin-2-yl)piperazine-1-carbonyl)-5-cyanobenzofuran | $^1$HNMR (500 MHz, CDCl$_3$): δ7.68 (d, J = 8.0 Hz 1H), 7.64 (s, 1H), 7.46 (s, 1H), 7.34 (d, J = 8.0 Hz, 1H), 6.95 (d, J = 8.8 Hz, 1H), 6.71 (d, J = 8.7 Hz, 1H), 3.78 (m, 2H), 3.53 (m, 2H), 3.21 (m, 4H); ESI-MS: m/z = 401 [M + H]+ |
| Compound 77 | 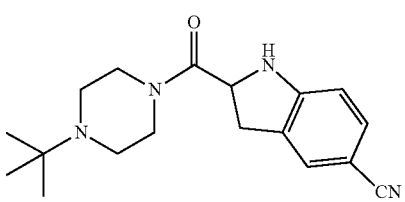 [SMILES: CC(C)(C)N1CCN(C(=O)C2Cc3cc(C#N)ccc3N2)CC1]<br>2-(4-(tert-butyl)piperazine-1-carbonyl)-5-cyanoindoline | $^1$HNMR (500 MHz, CDCl$_3$): δ7.51 (s, 1H), 7.22 (d, J = 8.6 Hz, 1H), 6.75 (d, J = 8.6 Hz, 1H), 4.72 (s, 1H), 3.92 (m, 1H), 3.77 (m, 2H), 3.52 (m, 2H), 3.23 (m, 4H), 3.16 (m, 1H), 2.92 (m, 1H), 1.21 (s, 9H); ESI-MS: m/z = 313 [M + H]$^+$ |
| Compound 78 | 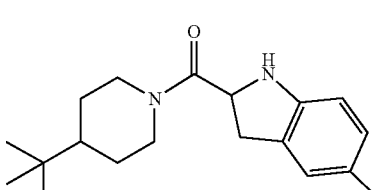<br>2-(4-(tert-butyl)piperidine-1-carbonyl)-5-cyanoindoline | $^1$HNMR (500 MHz, CDCl$_3$): δ7.54 (s, 1H), 7.21 (d, J = 8.6 Hz, 1H), 6.74 (d, J = 8.6 Hz, 1H), 4.74 (s, 1H), 4.71-4.64 (m, 1H), 4.56-4.47 (m, 1H), 3.93 (m, 1H), 3.15 (m, 1H), 2.97-2.81 (m, 2H), 2.77-2.69 (m, 1H), 1.56-1.41 (m, 2H), 1.21-1.09 (m, 1H), 1.03-0.79 (m, 2H), 0.69 (s, 9H); ESI-MS: m/z = 312 [M + H]$^+$. |
| Compound 79 | 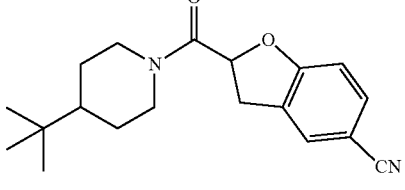<br>2-(4-(tert-butyl)piperidine-1-carbonyl)-2,3-2H-5-cyanobenzofuran | $^1$HNMR (500 MHz, CDCl$_3$): δ7.69 (d, J = 8.2 Hz, 1H), 7.60 (s, 1H), 7.15 (d, J = 8.2 Hz, 1H), 4.93 (t, 1H), 4.70-4.62 (m, 1H), 4.55-4.47 (m, 1H), 3.30 (m, 1H), 3.10 (m, 1H), 2.96-2.82 (m, 2H), 2.76-2.69 (m, 1H), 1.55-1.42 (m, 2H), 1.23-1.09 (m, 1H), 1.02-0.80 (m, 2H), 0.69 (s, 9H); ESI-MS: m/z = 313 [M + H]$^+$. |

TABLE 2.5-continued

NMR and mass spectrometry data of Compounds 69~80

| Compound No. of preparation examples | Name of Compound | NMR and mass spectrometry data |
|---|---|---|
| Compound 80 | 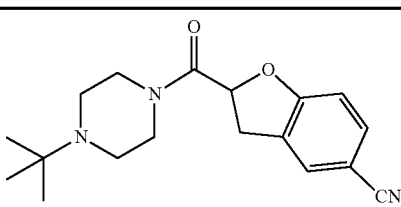<br>2-(4-(tert-butyl)piperazine-1-carbonyl)-2,3-2H-5-cyano-benzofuran | $^1$HNMR (500 MHz, CDCl$_3$): δ7.68 (d, J = 8.2 Hz, 1H), 7.61 (s, 1H), 7.05 (d, J = 8.2 Hz, 1H), 4.92 (t, 1H), 3.77 (m, 2H), 3.52 (m, 2H), 3.23 (m, 4H), 3.23(m, 1H), 2.98 (m, 1H), 1.22 (s, 9H); ESI-MS: m/z = 314 [M + H]$^+$ |

III. Biological Evaluation

1. FLIPR Assay of Inhibitory Activity on Human TRPA1

A calcium ion flux fluorescence method (FLIPR assay) was adopted to measure the inhibitory activity of compounds on human TRPA1 channel. The literature reports of Lee and Chen et al. may be referred to for the method [Lee et al. Br J Pharmacol 2008, 153 (8): 1739-1749] [Chen et al. Pain 2011, 152(5):1165-72].

(1) Cell Culture

A HEK293 recombinant cell strain stably expressing human TRPA1 (Creative Biogene, NY) was cultured in DMEM (Thermo Fisher Scientific, Shanghai) medium (containing 10% calf serum, 5 μg/ml Blasticidin and 400 ug/ml G418). The incubator was under a condition of 37° C. and air humidity with 5% CO$_2$.

(2) Preparation of Cell Analysis Plate

TRPA1 cells were seeded in a 96-well analysis plate at a density of 75,000 cells per well (100 ul/well), and cultured overnight in an incubator at 37° C. and 5% CO$_2$. On the second day, incubation was continued overnight under the same condition to induce the expression of TRPA1 after the culture medium in each well was poured out and a fresh supplement with the same culture medium containing 0.1 μg/ml Tetracycline was added. The further next day, the culture medium was pour out, a DMEM culture solution (also containing 2.5 mM Probenicid) containing 5 μM Fluo-4 AM (Molecular Probes) was added to each well, and incubation was conducted at 37° C. for 1 hour.

(3) Preparation of Compound Analysis Plate

The compound was dissolved in 100% DMSO to prepare a 30 mM stock solution which was stored at −20° C. On the day of use, the compound stock solution was thawed at room temperature. Each compound was subjected to 1:5 serial dilution using DMSO medium at a starting concentration of 30 μM with 9 concentration points on a 96-well plate. Each compound was diluted in duplicate for testing. Ruthenium Red was used as the positive control compound and the same dilution was carried out at a starting concentration of 3 μM.

(4) FLIPR Assay

The cell analysis plate was placed in an FLIPR instrument (Molecular Probes), and the compound in the compound plate was added to the corresponding hole on the cell analysis plate (First addition) via an automatic program, and the calcium ion fluorescence signal was recorded to determine whether the compound had agonistic activity. After 10 minutes, CaCl$_2$ (Second addition) was added a final concentration of 3 mM to each well to stimulate intracellular calcium flux signals. Ca$^{++}$-dependent fluorescence signal was monitored continuously at 538 nm wavelength to analyze the inhibitory activity of the compounds.

(5) Data Analysis

The data was collected and analyzed using a FLIPR program. The fluorescence peak value was used to evaluate the inhibitory (or agonistic) activity of the compounds at each concentration. EXCEL and PRISM programs were used to calculate the IC50 value of the compounds.

TABLE 3.1

Inhibitory activity of compounds on TRPA1 (FLIPR assay)

| Compound No. | TRPA1 (IC$_{50}$, μM) |
|---|---|
| 1 | 0.040 |
| 2 | 0.105 |
| 3 | 1.58 |
| 4 | 0.152 |
| 5 | 0.129 |
| 6 | 0.035 |
| 7 | 0.064 |
| 8 | 0.568 |
| 9 | 5.670 |
| 10 | 0.032 |
| 11 | 0.019 |
| 12 | 6.230 |
| 13 | 0.378 |
| 14 | 0.087 |
| 15 | 0.023 |
| 16 | 8.921 |
| 17 | 0.018 |
| 18 | 0.038 |
| 19 | 0.087 |
| 20 | 0.056 |
| 21 | 0.875 |
| 22 | 0.765 |
| 23 | 0.231 |
| 24 | 0.576 |
| 25 | 0.876 |
| 26 | 2.832 |
| 27 | 0.567 |
| 28 | 0.015 |
| 29 | 0.026 |
| 30 | 0.054 |
| 31 | 0.087 |
| 32 | 0.543 |
| 33 | 0.092 |
| 34 | 0.287 |
| 35 | 0.085 |

TABLE 3.1-continued

Inhibitory activity of compounds on TRPA1 (FLIPR assay)

| Compound No. | TRPA1 ($IC_{50}$, µM) |
|---|---|
| 36 | 1.25 |
| 37 | 5.21 |
| 38 | 10.24 |
| 39 | 1.08 |
| 40 | 0.95 |
| 41 | 3.07 |
| 42 | 4.65 |
| 43 | 0.091 |
| 44 | 0.28 |
| 45 | 0.072 |
| 46 | 0.108 |
| 47 | 0.038 |
| 48 | 0.065 |
| 49 | 0.325 |
| 50 | 0.028 |
| 51 | 0.182 |
| 52 | 0.465 |
| 53 | 0.862 |
| 54 | 0.072 |
| 55 | 0.091 |
| 56 | 0.076 |
| 57 | 0.051 |
| 58 | 0.62 |
| 59 | 0.751 |
| 60 | 0.847 |
| 61 | 2.87 |
| 62 | 6.07 |
| 63 | 0.56 |
| 64 | 0.552 |
| 65 | 1.075 |
| 66 | 0.105 |
| 67 | 3.78 |
| 68 | 0.112 |
| 69 | 0.386 |
| 70 | 0.092 |
| 71 | 0.866 |
| 72 | 0.971 |
| 73 | 0.261 |
| 74 | 0.116 |
| 75 | 0.285 |
| 76 | 4.97 |
| 77 | 0.091 |
| 78 | 0.053 |
| 79 | 0.082 |
| 80 | 0.068 |

2. Inhibitory Activity on Human TRPA1 by Conventional Patch Clamp Assay

In order to compare the influences of different measuring methods on the inhibitory activity of compounds, a conventional patch clamp method was used to further measure the inhibitory activity of compounds 1, 11, 31, 50, and 78 on TRPA1. The principle and procedures of the conventional patch clamp assay could be found in the literature report of Chen et al [Chen et al. Pain 2011, 152(5):1165-72].

(1) Cell Culture

Evaluation of TRPA1 inhibitory activity of compounds was conducted using the HEK293 recombinant cell strain (Creative Biogene, NY) stably expressing human TRPA1. Cells were cultured in a DMEM/F12 (3:1, Thermo Fisher Scientific) medium (containing 5% calf serum, 2 mM glutamine and 20 mM HEPES) in an incubator at 37° C. and air humidity containing 5% $CO_2$.

During the experiment, the adherent cells were placed in a recording room under the inverted microscope. All experiments were performed at room temperature. Each cell itself was used as a control thereof.

(2) Compound Testing

Test compounds at a final concentration were all prepared on the testing day and then dissolved in the extracellular fluid. The extracellular fluid was (mM): NaCl, 137; KCl, 4; $CaCl_2$, 1.8; $MgCl_2$, 1; HEPES, 10; glucose 10; pH 7.4 (NaOH titration). All the solutions of the test compounds and control compounds contained 0.3% DMSO.

The compounds were all perfused with a perfusion system by virtue of their own gravity. At least two cells were tested for each concentration of the compound. After the current became stable, the variation in magnitude of the current before and after the compound was used to calculate the blocking effect of the compound. 100 µM cinnamaldehyde was used as the positive control.

(3) Electrophysiology

The cells were transferred to the perfusion tank and perfused with extracellular fluid. The intracellular fluid was: 130 mM K-aspartate; 5 mM $MgCl_2$; 5 mM EGTA; 10 mM HEPES; pH 7.2 (KOH titration). The intracellular fluid was stored in a small amount in a −80 degree refrigerator in batches, and thawed on the day of the experiment. The electrode was pulled with PC-10 (Narishige, Japan). Whole-cell patch clamp recording was adopted and noise was filtered at one-fifth of the sampling frequency.

(4) Testing Procedures and Result Analysis

The cells were clamped at 20 mV, and then depolarized to 80 mV with a square wave of 500 milliseconds to obtain the TRPA1 current (see FIG. 1).

Figure 2:
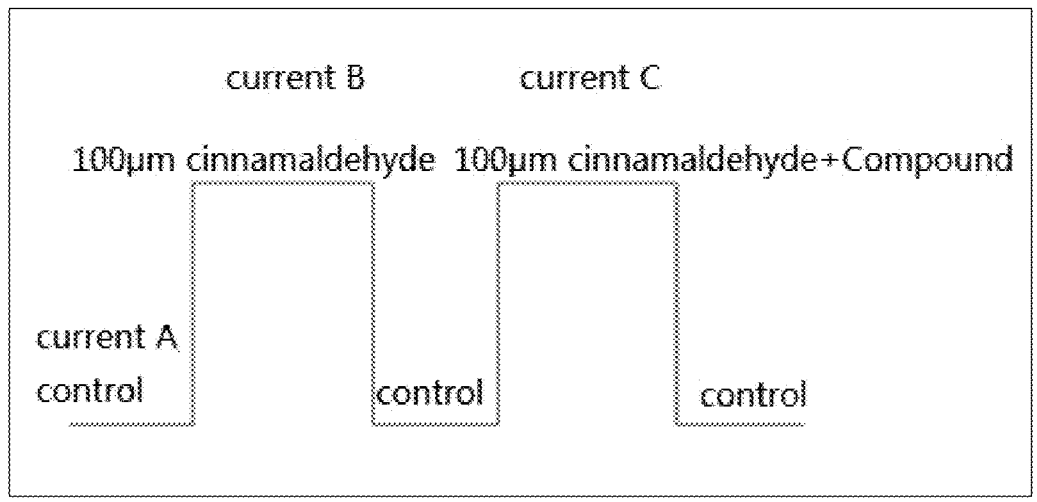
FIG. 2 is a schematic diagram of the TRPA testing process.

This procedure was repeated every 3 seconds. Cells were patched in a normal extracellular fluid, current A was obtained via voltage procedure testing, and then perfusion was conducted with an extracellular fluid added with 100 µM cinnamaldehyde to activate TRPA1 current to obtain current B. After the current stabilized, elution was conducted with normal extracellular fluid and perfusion was conducted with an extracellular fluid added with 100 µM cinnamaldehyde and a compound at various concentrations to obtain current C. Finally, blocking rate of the compound was obtained according to (C-A)/(B-A), see FIG. 2.

Data collection and analysis was conducted using pCLAMP 10 (Molecular Devices, Union City, CA). Current stabilization meant that the variation in the current with time was within a limited range. The magnitude of the current after stabilization was used to reflect the effect of the compound in this process.

TABLE 3.2

Inhibitory activity of some compounds on human TRPA1 (conventional patch clamp method)

| Compound No. | TRPA1 ($IC_{50}$, µM) |
|---|---|
| 1 | 0.056 |
| 11 | 0.035 |
| 31 | 0.098 |
| 50 | 0.065 |
| 78 | 0.083 |

3. Inhibitory Activity on Human TRPC6 by Conventional Patch Clamp Assay

In order to test the selectivity of the compounds in TRPA1 inhibition, a conventional patch clamp method was used to further measure the inhibitory activity of compounds on TRPC6. The principle and procedures of the conventional patch clamp assay could be found in the literature report of Ambrus et al [Ambrus et al. J Cell and Mol Med 2015, 19 (12):2771-9].

(1) Cell Culture

Evaluation of TRPC6 inhibitory activity of compounds was conducted using the HEK293 recombinant cell strain (Creative Biogene, NY) stably expressing human TRPC6. Cells were cultured in a DMEM/F12 (3:1, Thermo Fisher Scientific) medium (containing 5% calf serum, 2 mM glutamine and 20 mM HEPES) in an incubator at 37° C. and air humidity containing 5% $CO_2$.

During the experiment, the adherent cells were placed in a recording room under the inverted microscope. All experiments were performed at room temperature. Each cell itself was used as a control thereof.

(2) Compound Testing

Test compounds at a final concentration were all prepared on the testing day and then dissolved in the extracellular fluid. The extracellular fluid was (mM): NaCl, 137; KCl, 4; $CaCl_2$, 1.8; $MgCl_2$, 1; HEPES, 10; glucose 10; pH 7.4 (NaOH titration). Low-Ca extracellular fluid was (mM): NaCl, 138.3; KCl, 4; $CaCl_2$, 0.5; $MgCl_2$, 1; HEPES, 10; glucose 10; pH 7.4 (NaOH titration). All the solutions of the test compounds and control compounds contained 0.3% DMSO.

The compounds were all perfused with a perfusion system by virtue of their own gravity. At least two cells were tested for each concentration of the compound. After the current became stable, the variation in magnitude of the current before and after the compound was used to calculate the blocking effect of the compound. High concentration lanthanum chloride was used as the positive control.

(3) Electrophysiology

The cells were transferred to the perfusion tank and perfused with extracellular fluid. The intracellular fluid was: 130 mM K-aspartate; 5 mM $MgCl_2$; 5 mM EGTA; 10 mM HEPES; pH 7.2 (KOH titration). The intracellular fluid was stored in a small amount in a −80 degree refrigerator in batches, and thawed on the day of the experiment. The electrode was pulled with PC-10 (Narishige, Japan). Whole-cell patch clamp recording was adopted and noise was filtered at one-fifth of the sampling frequency.

(4) Testing Procedures and Result Analysis

Figure 3:
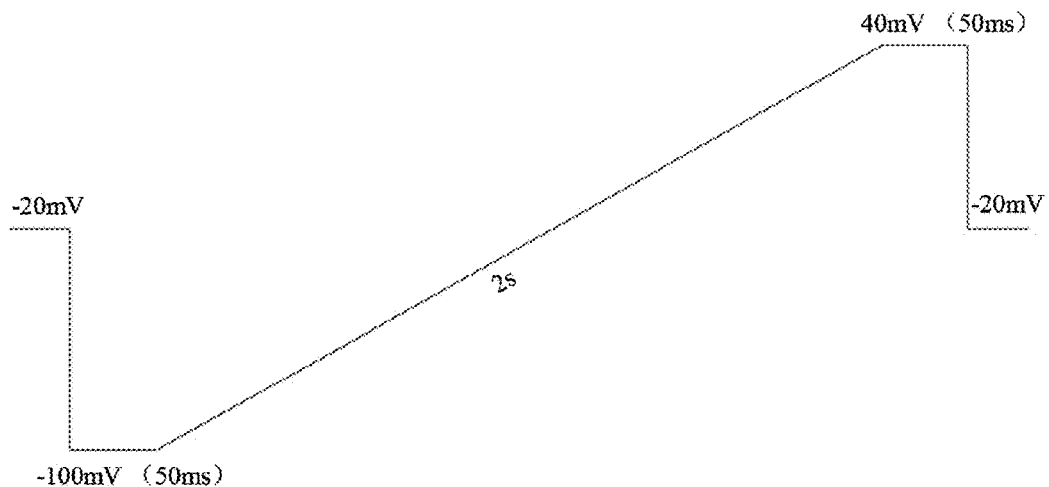
FIG. 3 a diagram of TRPC6 testing voltage procedure.

The cells were clamped at −20 mV, and then hyperpolarized to −100 mV with a square wave of 50 milliseconds, further increased from −100 mV, with a RAMP square wave of 2 seconds, continually to 40 mV which lasted for 50 milliseconds, and finally returned to the clamping voltage of −20 mV, so as to obtain the TRPC6 current (see FIG. 3). This procedure was repeated once every 10 seconds. The maximum current at −100 mV was considered as the TRPC6 current.

Figure 4:
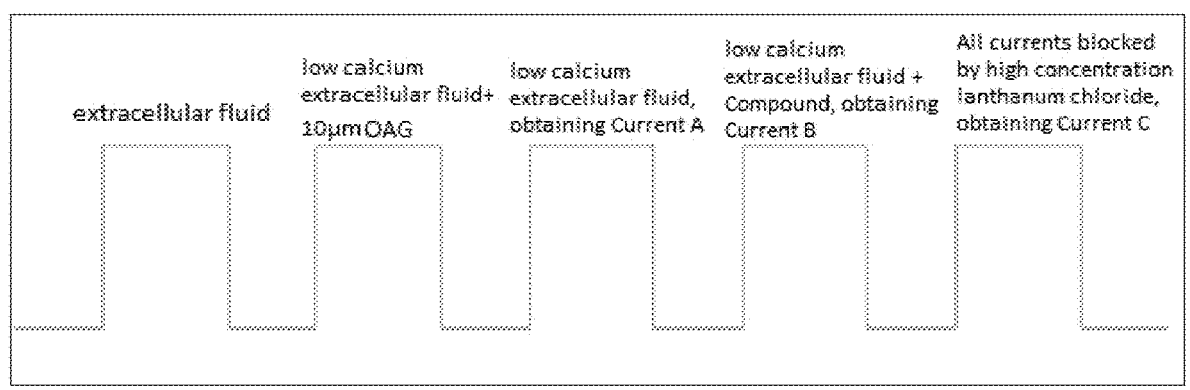
FIG. 4 is a schematic diagram of the TRPC6 testing process.

Cells were patched in a normal extracellular fluid, and current A was obtained via voltage procedure testing according to FIG. 3, and then TRPC6 current was activated by perfusion with a low-Ca extracellular fluid added with 10 µM 2-acetyl-1-oleoyl-SN-glycerol (OAG). Then perfusion was conducted with low-Ca extracellular fluid and the current A was obtained after the current became stabilized. Next, perfusion was conducted with low-Ca extracellular fluid plus a compound at various concentrations to obtain current B, and finally perfusion was conducted with a high concentration-lanthanum chloride extracellular fluid to obtain current C. At last, blocking rate of the compound was obtained according to (B-C)/(A-C) (FIG. 4).

Data collection and analysis was conducted using pCLAMP 10 (Molecular Devices, Union City, CA). Current stabilization meant that the variation in the current with time was within a limited range. The magnitude of the current after stabilization was used to reflect the effect of the compound in this process.

TABLE 3.3

Comparison of inhibitory activities of some compounds on human TRPC6 and on human TRPA1 (conventional patch clamp method)

| Compond No. | TRPC6 Inhibition rate (5 µM) | TRPA1 % Inhibition rate (5 µM) |
|---|---|---|
| 1 | −60% | 99% |
| 31 | 26% | 117% |

4. Effects of Compounds on Ovalbumin-Induced Asthma in Mouse and Rat Models (1) Animals for Experiments SPF-grade SD male rats (purchased from Zhejiang Academy of Medical Sciences, license number SCXK (Zhejiang) 2019-0002) with a body weight of 160-180 g; and SPF-grade female BABL/c mice (purchased from Zhejiang Weitong Lihua Experimental Animals Technology Co., Ltd., license number SCXK (Zhejiang) 2019-0001) with a body weight of 16-18 g were used. The above animals were raised by the Experimental Animal Center of Zhejiang Academy of Traditional Chinese Medicine.

(2) Drugs and Reagents

Ovalbumin OVA (Solarbio, 326A0516); egg white albumin OVA (Yuanye Bio, C18J9X53021); OVA (Sigma, SLBQ9036V); dexamethasone sodium phosphate injection, 5 mg/ml/injection (Shiyao Yinhu Pharmaceutical Co., Ltd., 10812201); aluminum hydroxide (Shanghai Zhanyun Chemical Co., Ltd., 101201).

Formulation of compound solution: compound was vortexed in a solvent system, dissolved by ultrasound, and prepared into a solution at a corresponding concentration, which was prepared just before use (the solvent system was composed of 5% Solutol HS 15, 5% DMSO and 90% physiological saline).

(3) Experimental Apparatus

Medical ultrasonic nebulizer (Beijing Yadu Pharmaceutical Technology Co., Ltd.); nebulizer (PARI, Germany); Sartorius water purifier (Sartorius, Germany); reverse osmosis water purifier (Hangzhou Yongjieda Purification Technology Co., Ltd.); electronic analytical balance (Mettler-Toledo Instruments (Shanghai) Co., Ltd.).

(4) Experimental Methods

A. Animal Grouping:

BABL/c mice or SD rats were randomly divided into: normal control group, model control group, dexamethasone group (0.72 mg/kg), and the respective test compound groups (one group for each dose), 10 mice in each group; 6 rats in each group.

B. Modeling and Administrating:

Sensitization of mice: on the mornings of Day 0, Day 7, and Day 14, mice in the model control group and the respective drug administration groups were intraperitoneally injected with 0.2 ml of 10% OVA sensitizing solution (Yuanye Bio), and the normal control group was intraperitoneally injected with an equal volume of normal saline. In the afternoons of Day 7 and Day 14, mice in the model control group and the respective drug administration groups were intraperitoneally injected with 0.2 ml of 10% OVA (Sigma), and the normal control group was intraperitoneally injected with an equal volume of normal saline.

Sensitization of rats: On Day 1 and Day 8, the model control group and the respective drug administration groups were intraperitoneally injected with 1 ml of 10% OVA sensitizing solution, and the normal group was intraperitoneally injected with an equal volume of normal saline.

C. Pharmacological Intervention:

Mice: from Day 21, the normal control group and the model control group were not treated; the dexamethasone group and the respective test compound groups were intraperitoneally injected, 20 minutes before each challenge, with the corresponding drugs, injection volume: 0.1 ml/10 g, administered for 7 consecutive days; mice in the test compound-oral group were given the corresponding drugs by intragastric administration 30 minutes before the challenge; the test compound-atomization group or the dexamethasone-atomization group was given the corresponding drugs at different concentrations before challenge, 8 ml for each group, atomization for 30 minutes; the normal control group and the model control group were given no treatment. Administration was conducted for 7 consecutive days.

Rat: from Day 15, the dexamethasone group and the respective test compound groups were intraperitoneally injected, 20 minutes before challenge, with the corresponding drugs with an injection volume of 0.3 ml/100 g; the model control group was intraperitoneally injected, 20 minutes before challenge, with an equal volume of solvent system; and the normal control group was not treated. Administration was conducted for 7 consecutive days.

D. Challenging:

Mice: from Day 21, the mice in the model control group and the respective administration groups were placed in airtight containers in turn, and the challenging solution was atomized with an ultrasonic nebulizer (approximately 6-8 ml each time), twice a day, OVA challenging solution from Yuanye Shanghai was atomized in the morning, and OVA challenging solution from Sigma was atomized in the afternoon. Mice were challenged for 30 minutes per atomization, for 7 consecutive days. The normal control group was not treated. Mice in the model control group developing cyanosis of lips, accelerated breathing, unsteadiness during standing, nodding breathing, abdominal muscle cramps, etc. was deemed as a sign of success of the animal model.

Rat: from Day 15, the model control group and the respective administration groups were respectively placed in self-made airtight glass containers after they were administered at the corresponding time, and 1.5% OVA challenging solution was atomized with an ultrasonic nebulizer, the diameter of the atomized particles being 3-6 μm, once per day, 30 minutes each time, 7 consecutive days. For the normal control group normal saline was atomized for the same time length.

E. Mouse Bronchoalveolar Lavage Fluid (BALF) Collection:

24 hours after completion of the last challenge, the trachea of the mouse was exposed in front of the neck, a horizontal incision was made in the trachea with an ophthalmic scissor, and a 5 ml syringe-modified tracheal intubation needle was inserted, the left main bronchus was ligated, and the right main bronchus was intubated and tightened with surgical suture. Bronchoalveolar lavage was conducted 3 times with 0.3 ml normal saline, pumpback twice each time. The BALF was combined and collected in a 1.5 ml test tube, which was placed on ice or in a refrigerator at 4 degrees.

F. Classification and Counting of Cells in Mouse Bronchoalveolar Lavage Fluid (BALF):

50 μl of the above BALF was taken, and 100 μl white blood cell counting diluent (2% iced acetic acid solution) was added thereto and mixed evenly therewith. The total number of white blood cells was counted under a microscope with a hemocytometer. The remainder was centrifuged at 4000 r/min for 10 min, and the supernatant was aliquoted and stored at −80° C. An appropriate amount of resuspension solution was added to and mixed evenly with the cell pellet, and 60 μl was taken for preparation of cytospin. Paraffin was used to draw lines on both sides of the area where cells were located on a slide to line out the staining area. After drying, it was stained with Swiss-Giemsa. After the action of 100 μl of staining solution A for 2 min and the action of 300 μl of destaining solution B for 10 minutes, it was rinsed with clean water for about 15 s. After it was dried, the cells were classified and counted under a microscope. 100 white blood cells were counted for each specimen, and the numbers of the Eosinophils, Neutrophils, Lymphocytes and Macrophages were counted respectively to obtain the percentages of the respective types of cells, thereby calculating the absolute values. The cell counting was conducted using a single-blind method, all completed by the same experimenter.

G. HE Staining to Observe Lung Tissue Inflammation Area and Airway Inflammation Evaluation in Rats:

The rat was anesthetized with 10% urethane at 1.3 ml/100 g volume, and the left lung tissue was taken and fixed in 4% neutral formaldehyde, paraffin-embedded according to routine operation, sectioned for HE staining. Pathological changes of lung tissue were observed under a microscope (40×). NIS-Elements D 3.2 software was used to manually integrate and measure the total area of lung tissue sections and the inflammation area under all fields of view, the total areas under each field of view were accumulated, and the percentage of the cumulative area of inflammation in the total area was calculated, wherein the percentage of inflammation area=cumulative area of inflammation/total area× 100%. The evaluation criterion for airway inflammation was shown in Table 4 below:

TABLE 4

| Airway inflammation scoring index | Score |
| --- | --- |
| No inflammatory cell infiltration around the airway | 0 |
| small amount of inflammatory cell infiltration around the airway | 1 |
| 1 layer of inflammatory cell infiltration around most of the airway | 2 |
| 2-4 layers of inflammatory cell infiltration around most of the airway | 3 |
| more than 4 layers of infiltrating cells around most of the airway | 4 |
| multiple layers of inflammatory cell infiltration around almost the entire airway | 5 |

H. Statistical Methods

All data were expressed as mean±standard deviation (x̄±s), and the data were processed by SPSS 20.0 statistical software. One-way ANOVA was adopted for comparison of the multiple-sample means, and $P<0.05$ was considered statistically significant.

(5) Experimental Results

Experimental results were shown in FIG. 5 to FIG. 9.

Figure 5:
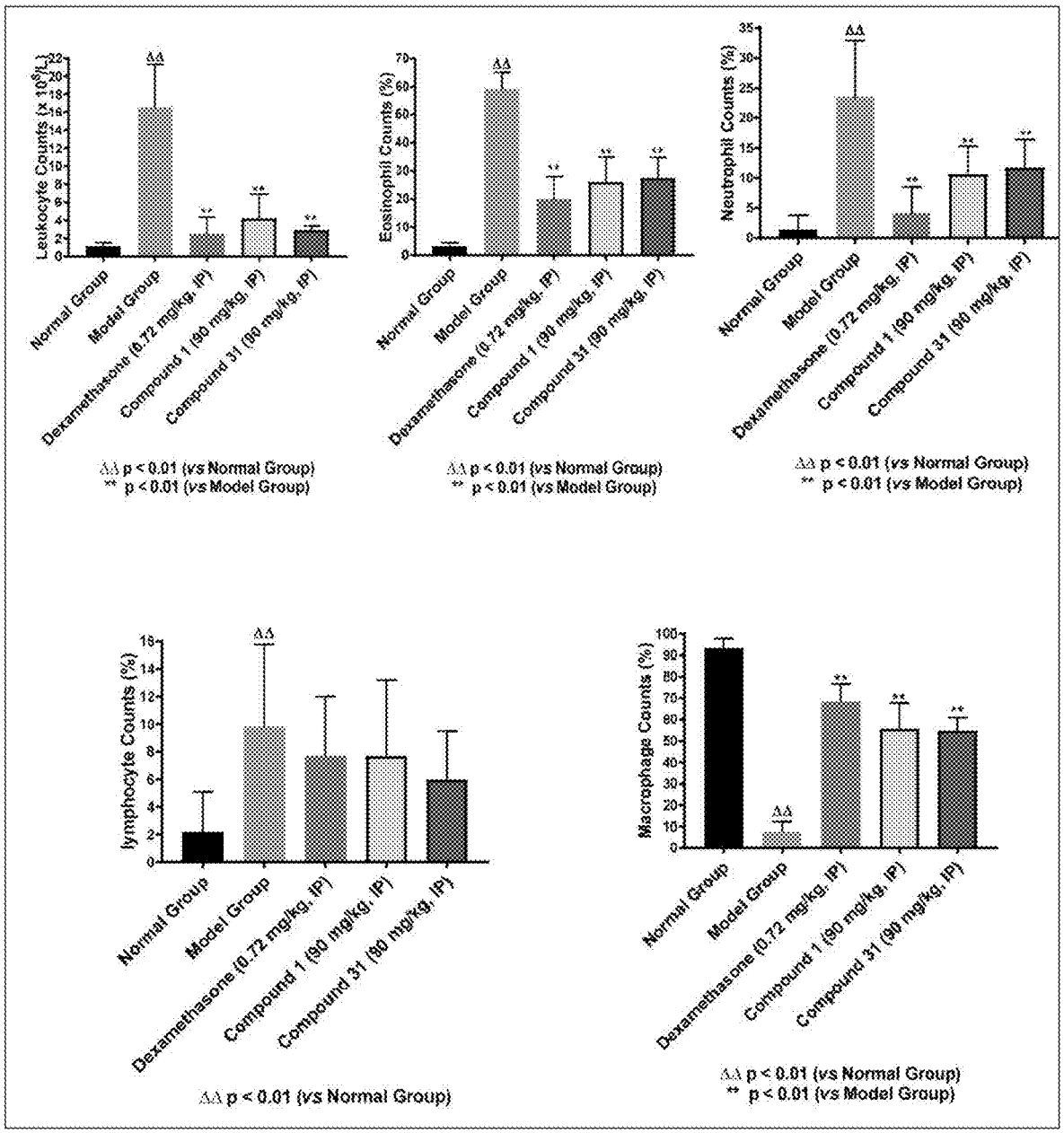
FIG. 5 a graph showing the effects of Compound 1 and Compound 31 on the classification and counting of leukocytes in asthmatic mice BALF.

FIG. 5 showed the effects of Compound 1 and Compound 31 on the classification and counting of leukocytes in asthmatic mice BALF. As shown in FIG. 5, as compared with the normal control group (Normal control), the total number of leukocytes and the percentages of eosinophils, neutrophils, and lymphocytes in the model control group (Model control) BALF increased significantly ($P<0.01$), and the percentage of macrophages significantly decreased ($P<0.01$); as compared with the model control group, Compound 1 and Compound 31 administered by intraperitoneal injection both decreased the total number of leukocytes and the percentages of eosinophils, neutrophils in BALF ($P<0.01$), and increased the percentage of macrophages ($P<0.01$), and the results were consistent with the effect of Dexamethasone.

Figure 6:
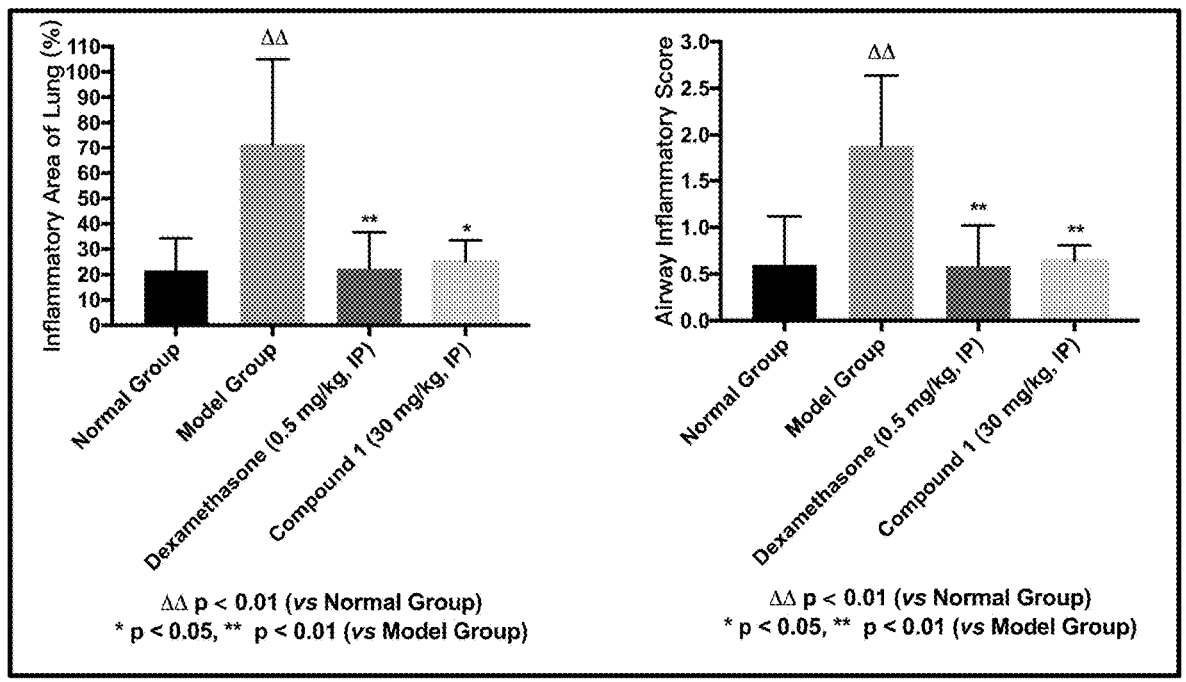
FIG. 6 is a graph showing the effect of Compound 1 on lung tissue inflammation area and airway inflammation in asthmatic rats.

FIG. 6 showed the effect of Compound 1 on the lung tissue inflammation area and airway inflammation in asthmatic rats. As shown in FIG. 6, as compared with the normal control group (Normal control), the lung tissue inflammation area and airway inflammation score in the model control group increased significantly ($P<0.01$); as compared with the model group, Compound 1 administered by intraperitoneal injection significantly decreased lung tissue inflammation area and airway inflammation score in asthmatic rats ($P<0.05, 0.01$), and the results were consistent with the effect of dexamethasone.

Figure 7:
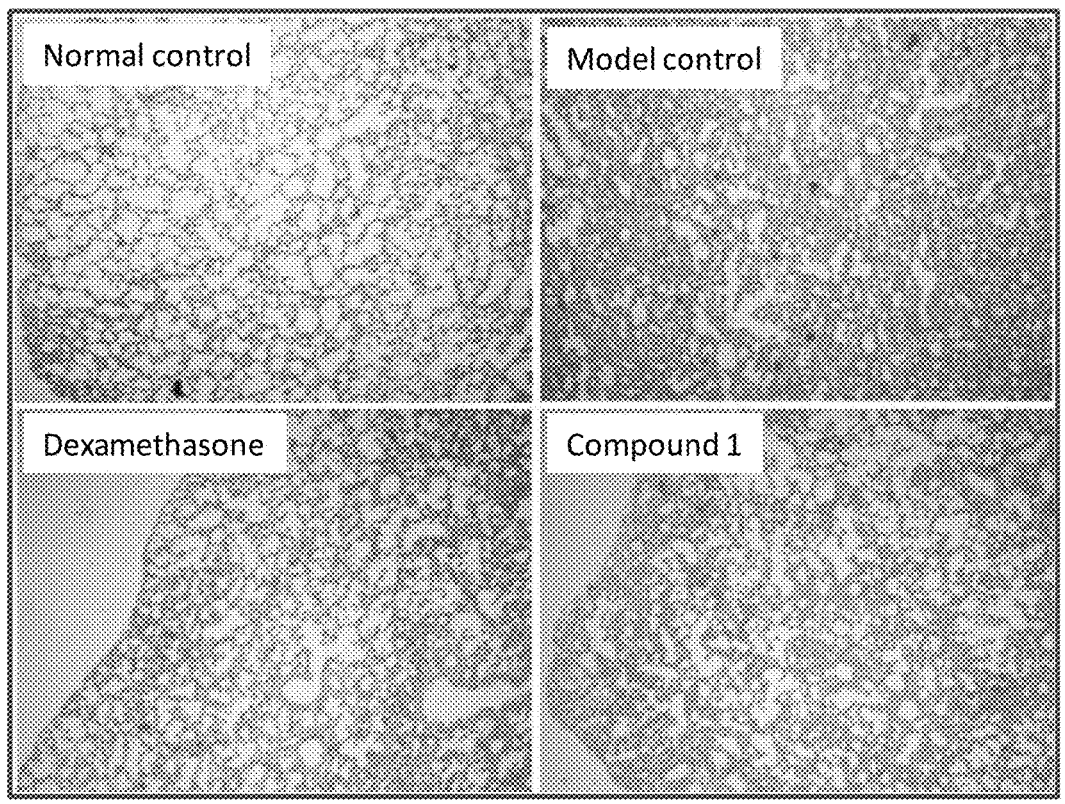
FIG. 7 is a graph showing the effect of Compound 1 on lung tissue inflammation area and airway inflammation in asthmatic rats.

FIG. 7 showed the effect of Compound 1 on the lung tissue inflammation area and airway inflammation in asthmatic rats (HEx40). As shown in FIG. 7, slight inflammation occurred in very few part of the lung tissue in the normal control group, and inflammatory cell infiltration was rarely seen around the airway; there was a large area of inflammation in the lung tissue in the model control group, and inflammatory cell infiltration could be seen around most of the airway; significant improvement was seen in the groups of dexamethasone and Compound 1 as compared with the model group.

Figure 8:
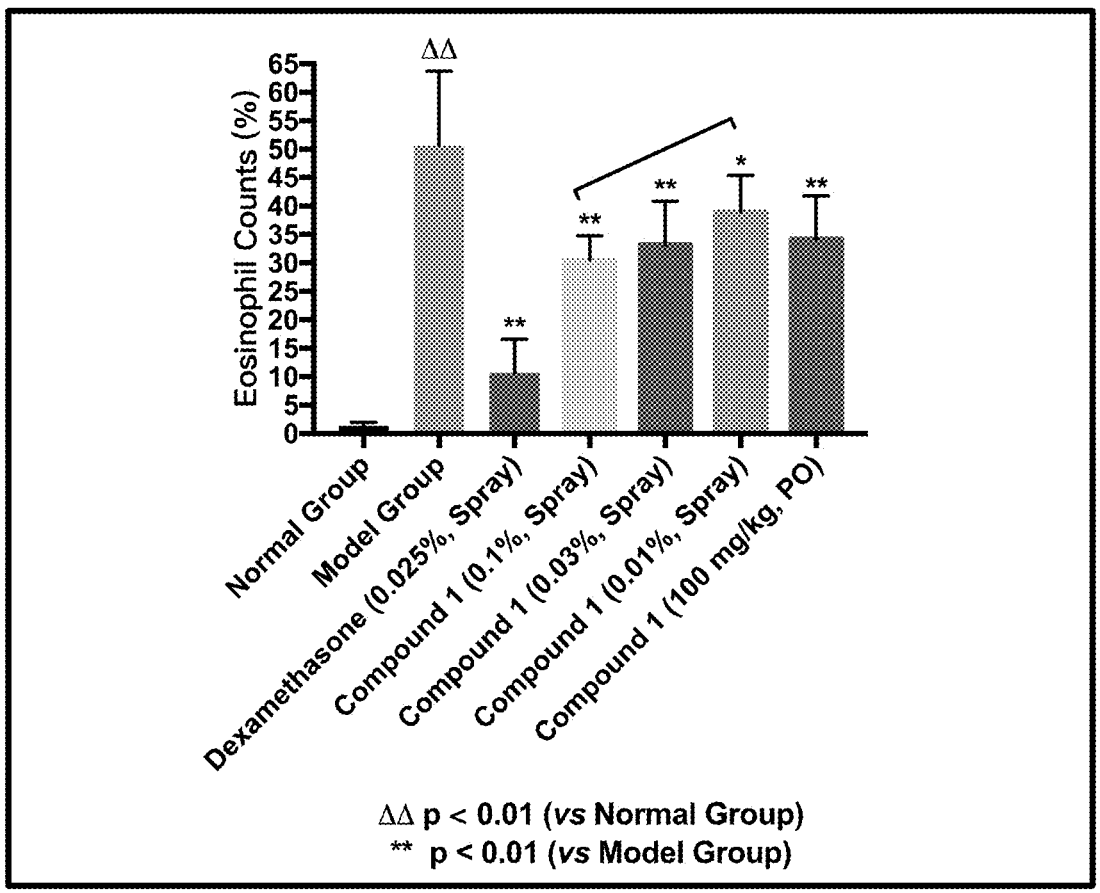
FIG. 8 is a graph showing the dose-dependent effect of Compound 1 on the counting of eosinophils in asthmatic mice BALF.

FIG. 8 showed that Compound 1 exhibited a dose-dependent effect on the eosinophil count in BALF of asthmatic mice. As shown in FIG. 8, as compared with the normal control group, the percentage of eosinophils in BALF in the model control group was significantly increased ($P<0.01$); as compared with the model control group, with Compound 1 administered by spray inhalation, the respective dose groups showed a dose-dependent decrease of eosinophils in BALF ($P<0.05, 0.01$); at the same time, oral administration of Compound 1 also significantly reduced eosinophils in BALF ($P<0.01$).

Figure 9:
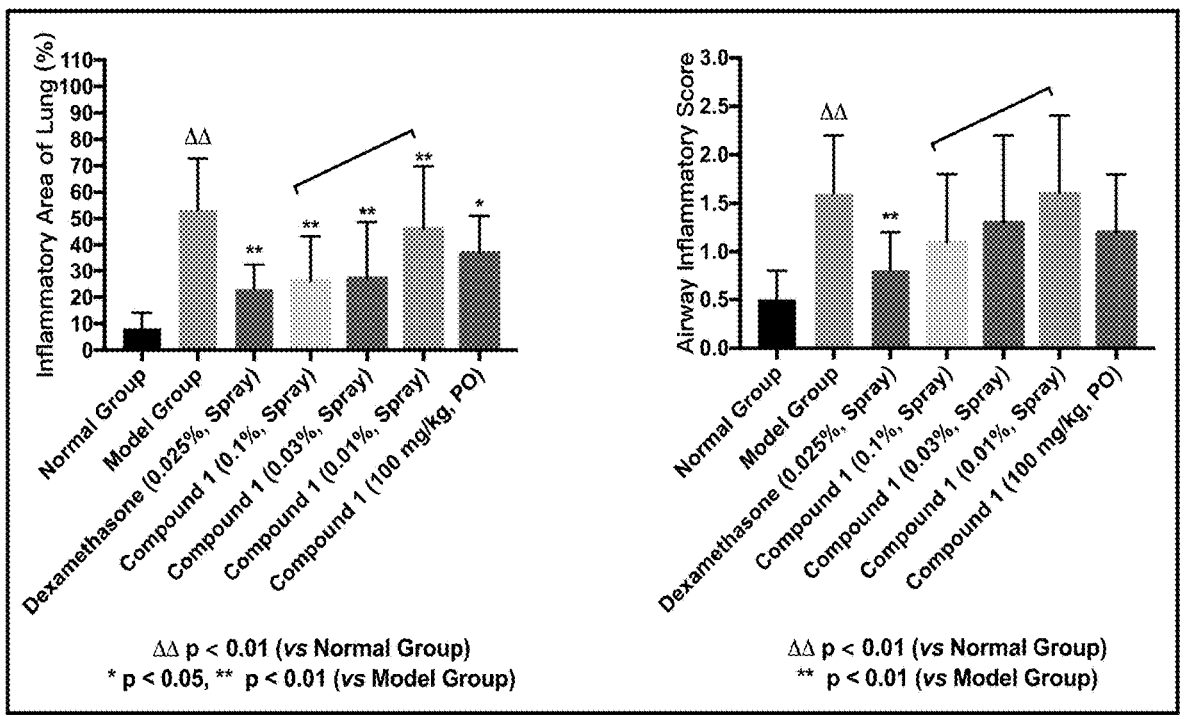
FIG. 9 is a graph showing a dose-dependent effect of Compound 1 on lung tissue inflammation area and airway inflammation in asthmatic mice.

FIG. 9 showed that Compound 1 exhibited a dose-dependent effect on the lung tissue inflammation area and airway inflammation in asthmatic mice. As shown in FIG. 9, as compared with the normal control group, the lung tissue inflammation area and airway inflammation score of the model control group significantly increased ($P<0.01$); as compared with the model control group, with Compound 1 administered by spray inhalation, the respective dose groups were showed to reduce the lung tissue inflammation area of asthmatic mice in a dose-dependent manner ($P<0.01, 0.05$), and the airway inflammation score also exhibited a decreasing trend, but not reaching a statistical significance ($P>0.05$); at the same time, oral administration of Compound 1 also significantly reduced the lung tissue inflammation area of asthmatic mice ($P<0.05$).

The invention claimed is:

1. A heteroaromatic acetamide derivative, characterized in that the derivative is a compound selected from the following compounds:
   4-((1-(4-(4-(trifluoromethyl)phenyl)piperazine-1-carbonyl)cyclopentyl)amino)benzonitrile;
   4-((1-(4-(3-(trifluoromethyl)phenyl)piperazine-1-carbonyl)cyclopentyl)amino)benzonitrile;
   4-((1-(4-(2-(trifluoromethyl)phenyl)piperazine-1-carbonyl)cyclopentyl)amino)benzonitrile;
   4-((1-(4-(2-(trifluoromethoxy)phenyl)piperazine-1-carbonyl)cyclopentyl)amino)benzonitrile;
   4-((1-(4-(4-(trifluoromethoxy)phenyl)piperazine-1-carbonyl)cyclopentyl)amino)benzonitrile;
   4-((1-(4-(4-chloro-2-methoxyphenyl)piperazine-1-carbonyl)cyclopentyl)amino)benzonitrile;
   4-((1-(4-(3-methyl)phenyl)piperazine-1-carbonyl)cyclopentyl)amino)benzonitrile;
   4-((1-(4-(5-(trifluoromethyl)pyridin-2-yl)piperazine-1-carbonyl)cyclopentyl)amino)benzonitrile;
   4-((1-(4-(6-(trifluoromethyl)pyridin-2-yl)piperazine-1-carbonyl)cyclopentyl)amino)benzonitrile;
   4-((1-(4-(6-(trifluoromethyl)pyridin-2-yl)piperazine-1-carbonyl)cyclopropyl)amino)benzonitrile;
   4-((1-(4-(6-(trifluoromethyl)pyridin-2-yl)piperazine-1-carbonyl)cyclobutyl)amino)benzonitrile;
   4-((3,3-dimethyl-1-oxo-1-(4-(6-trifluoromethyl)pyridin-2-yl)piperazine-1-yl)butan-2-yl)amino)benzonitrile;
   4-((1-(4-(6-methylpyridin-2-yl)piperazine-1-carbonyl)cyclopentyl)amino)benzonitrile;
   6-(4-(1-((4-cyanophenyl)amino)cyclopentane-1-carbonyl)piperazine-1-yl)N,N-dimethylnicotinamide;
   4-((1-(4-(5-(trifluoromethyl)pyrimidin-2-yl)piperazine-1-carbonyl)cyclopentyl)amino)benzonitrile;
   4-((1-(4-(4-(trifluoromethyl)pyrimidin-2-yl)piperazine-1-carbonyl)cyclopentyl)amino)benzonitrile;
   4-((1-(4-(6-(trifluoromethyl)pyridazin-3-yl)piperazine-1-carbonyl)cyclopentyl)amino)benzonitrile;
   4-((1-(4-(6-(trifluoromethyl)pyridazin-3-yl)piperazine-1-carbonyl)cyclopentyl)amino)chlorobenzene;
   4-((1-(4-(6-(trifluoromethyl)pyridazin-3-yl)piperazine-1-carbonyl)cyclopentyl)amino)nitrobenzene;
   2-chloro-4-((1-(4-(6-(trifluoromethyl)pyridazin-3-yl)piperazine-1-carbonyl)cyclopentyl)amino)benzonitrile;
   2-chloro-4-((1-(4-(6-(trifluoromethyl)pyridazin-3-yl)piperazine-1-carbonyl)phenyl)amino)benzonitrile;
   4-((1-(4-(5-(trifluoromethyl)thien-2-yl)piperazine-1-carbonyl)cyclopentyl)amino)benzonitrile;
   4-((1-(4-(5-(trifluoromethyl)thiazol-2-yl)piperazine-1-carbonyl)cyclopentyl)amino)benzonitrile;
   4-((1-(4-(1-methyl-1H-pyrazol-3-yl)piperazine-1-carbonyl)cyclopentyl)amino)benzonitrile;
   4-((1-(4-(6-(trifluoromethyl)pyridin-2-yl)piperazine-1-carbonyl)cyclopentyl)amino)phenylacetylene;
   4-((1-(4-(cyclopentanemethyl)piperazine-1-carbonyl)cyclopentyl)amino)benzonitrile;
   4-((1-(4-(tert-butyl)piperidine-1-carbonyl)cyclopentyl)amino)benzonitrile;
   4-((1-(4-(isobutyl)piperidine-1-carbonyl)cyclopentyl)amino)benzonitrile;
   4-((1-(4-(cyclopentyl)piperidine-1-carbonyl)cyclopentyl)amino)benzonitrile;
   4-((1-(8-aza-spiro [4.5]decane-8-carbonyl)cyclopentyl)amino)benzonitrile;
   4-((1-(4-(cyclohexyl)piperidine-1-carbonyl)cyclopentyl)amino)benzonitrile;
   4-((1-(4-(tert-butyl)piperidine-1-carbonyl)cyclopentyl)amino)phenylacetylene;

4-((1-(4-(tert-butyl)piperidine-1-carbonyl)cyclobutyl)amino)benzonitrile;
4-((1-(4-(tert-butyl)piperidine-1-carbonyl)cyclopropyl)amino)benzonitrile;
2-((1-(4-(tert-butyl)piperidine-1-carbonyl)cyclopentyl)amino) thiazole-4-carbonitrile;
2-((1-(4-(tert-butyl)piperidine-1-carbonyl)cyclopentyl)amino) thiazole-5-carbonitrile;
2-((1-(4-(tert-butyl)piperidine-1-carbonyl)cyclopentyl)amino) oxazole-4-carbonitrile;
4-((1-(4-(tert-butyl)piperidine-1-carbonyl)cyclopentyl)amino)-1-methyl-1H-imidazole-2-carbonitrile;
4-((1-(4-(tert-butyl)piperidine-1-carbonyl)tert-butyl)amino)benzonitrile;
4-((1-(4-(tert-butyl)piperidine-1-carbonyl)cyclopentyl)methylamino)benzonitrile;
4-((1-(4-(tert-butyl)piperidine-1-carbonyl)cyclopentyl)methylamino)trifluoromethylbenzene;
4-((1-(4-(tert-butyl)piperidine-1-carbonyl)cyclopentyl)amino)chlorobenzene;
4-((1-(4-(6-(trifluoromethyl)pyridin-2-yl)piperazine-1-carbonyl)cyclopentyl)oxy)benzonitrile;
4-((1-(4-(m-methylphenyl)piperazine-1-carbonyl)cyclopentyl)oxy)benzonitrile;
4-((1-(4-(trifluoromethyl)phenyl)piperazine-1-carbonyl)cyclopentyl)oxy)benzonitrile;
4-((1-(4-(4-(trifluoromethyl)pyrimidin-2-yl)piperazine-1-carbonyl)cyclopentyl)oxy)benzonitrile;
4-((1-(4-(4-(trifluoromethyl)pyrimidin-2-yl)piperazine-1-carbonyl)tert-butyl)oxy)benzonitrile;
4-((1-(4-(6-(trifluoromethyl)pyridazin-3-yl)piperazine-1-carbonyl)cyclopentyl)oxy)benzonitrile;
4-((1-(4-(6-(trifluoromethyl)pyridazin-3-yl)piperazine-1-carbonyl)cyclopentyl)oxy)nitrobenzene;
4-((1-(4-(tert-butyl)piperidine-1-carbonyl)cyclopentyl)oxy)benzonitrile;
4-((1-(4-(tert-butyl)piperazine-1-carbonyl)cyclopentyl)oxy)benzonitrile;
4-((1-(4-(6-(trifluoromethyl)pyridin-2-yl)piperazine-1-carbonyl)cyclobutyl)oxy)benzonitrile;
4-((1-(4-(4-(trifluoromethyl)pyrimidin-2-yl)piperazine-1-carbonyl)cyclopentyl)oxy)oxazole-4-carbonitrile;
2-chloro-4-((1-(4-(6-(trifluoromethyl)pyridazin-3-yl)piperazine-1-carbonyl)cyclopentyl)oxy)benzonitrile;
1-methyl-4-((1-(4-(5-(trifluoromethyl)pyridin-2-yl)piperazine-1-carbonyl)cyclopentyl)oxy)-1H-imidazole-2-carbonitrile;
2-((1-(4-(5-(trifluoromethyl)pyridin-2-yl)piperazine-1-carbonyl)cyclopentyl)oxy)thiazole-5-carbonitrile;
4-(1-phenyl-2-(4-6-(trifluoromethyl)pyridazin-3-yl)piperazine-1-yl)ethoxy)benzonitrile;
4-((1-(4-(tert-butyl)piperazine-1-carbonyl)cyclopentyl)oxy)trifluoromethylbenzene;
5-((1-(4-(tert-butyl)piperidine-1-carbonyl)cyclopentyl)oxy)-1-methyl-1H-pyrrole-3-carbonitrile;
4-((1-(4-(tert-butyl)piperazine-1-carbonyl)cyclopentyl)sulfanyl)benzonitrile;
5-((1-(4-(tert-butyl)piperidine-1-carbonyl)cyclopentyl)sulfanyl)-1-methyl-1H-indole;
4-((1-(8-(6-(trifluoromethyl)pyridin-2-yl)-3,8-diazabicyclo [3.2.1] octane-3-carbonyl)cyclopentyl)amino)benzonitrile;
4-((1-(5-(6-(trifluoromethyl)pyridin-2-yl)-2,5-diazabicyclo [2.2.2] octane-2-carbonyl)cyclopentyl)amino)benzonitrile;
4-((1-(8-(6-(trifluoromethyl)pyridin-2-yl)-3,8-diazabicyclo [3.2.1] octane-3-carbonyl)cyclopentyl)amino)benzonitrile; and
4-((1-(5-(6-(trifluoromethyl)pyridin-2-yl)-2,5-diazabicyclo [2.2.2] octane-2-carbonyl)cyclopentyl)oxy)benzonitrile or a pharmaceutically acceptable salt thereof.

2. A medicament for inhibiting TRPA1, characterized in that the medicament comprises the heteroaromatic acetamide derivative of claim 1 as active component and one or more pharmaceutically acceptable carriers or excipients.

3. The medicament of claim 2, characterized in that the medicament inhibits TRPA1 to treat a respiratory disease.

4. The medicament of claim 2, characterized in that the salts are pharmaceutically acceptable inorganic salts or organic salts.

5. The medicament of claim 4, characterized in that the carriers or excipients are selected from diluent, filler, binder, wetting agent, disintegrating agent, absorption promoter, surfactant, adsorption carrier, lubricant, flavoring agent, sweetener in pharmaceutical field.

6. The medicament of claim 2, characterized in that the medicament is in a dosage form of inhalant, tablet, capsule, suspension, gel, powder, oral liquid or injection.

* * * * *